United States Patent
Angrish et al.

(10) Patent No.: US 10,683,539 B2
(45) Date of Patent: Jun. 16, 2020

(54) COMPOUNDS FOR USE IN PCR SYSTEMS AND APPLICATIONS THEREOF

(71) Applicant: LIFE TECHNOLOGIES CORPORATION, Carlsbad, CA (US)

(72) Inventors: Parul Angrish, San Diego, CA (US); Zhiwei Yang, San Diego, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 237 days.

(21) Appl. No.: 15/882,789

(22) Filed: Jan. 29, 2018

(65) Prior Publication Data

US 2018/0223334 A1  Aug. 9, 2018

Related U.S. Application Data

(62) Division of application No. 14/523,410, filed on Oct. 24, 2014, now Pat. No. 9,914,964.

(60) Provisional application No. 61/895,876, filed on Oct. 25, 2013.

(51) Int. Cl.
| | |
|---|---|
| *C12Q 1/68* | (2018.01) |
| *C12Q 1/686* | (2018.01) |
| *C07D 207/16* | (2006.01) |
| *C07C 41/22* | (2006.01) |
| *C07C 211/63* | (2006.01) |
| *C07C 303/28* | (2006.01) |
| *C07D 211/60* | (2006.01) |
| *C11D 1/88* | (2006.01) |
| *C12N 9/12* | (2006.01) |
| *C12N 9/96* | (2006.01) |

(52) U.S. Cl.
CPC .............. *C12Q 1/686* (2013.01); *C07C 41/22* (2013.01); *C07C 211/63* (2013.01); *C07C 303/28* (2013.01); *C07D 207/16* (2013.01); *C07D 211/60* (2013.01); *C11D 1/88* (2013.01); *C12N 9/1252* (2013.01); *C12N 9/96* (2013.01)

(58) Field of Classification Search
CPC ....................................................... C12Q 1/686
USPC ....................................................... 435/6.12
See application file for complete search history.

(56) References Cited

U.S. PATENT DOCUMENTS

| | | |
|---|---|---|
| 5,210,036 A | 5/1993 | Comb et al. |
| 5,726,021 A | 3/1998 | Britschgi et al. |
| 5,730,990 A | 3/1998 | Greenwald et al. |
| 5,766,890 A | 6/1998 | Kacian et al. |
| 5,814,502 A | 9/1998 | Hoeltke et al. |

(Continued)

FOREIGN PATENT DOCUMENTS

| | | |
|---|---|---|
| CN | 101617045 A | 12/2009 |
| EP | 0455744 B1 | 8/1993 |

(Continued)

OTHER PUBLICATIONS

Extended European Search Report for Application No. 18185275.7, dated Mar. 1, 2019, 8 pages.

(Continued)

*Primary Examiner* — Jezia Riley
(74) *Attorney, Agent, or Firm* — Life Technologies Corporation; Jinhee Chang

(57) ABSTRACT

This disclosure relates to novel compounds for use in various compositions, kits and methods, including, for example, use in polymerase storage buffers and in nucleic acid synthesis or amplification reactions such as a polymerase chain reaction (PCR). Methods for preparing the novel compounds are also described.

12 Claims, 29 Drawing Sheets

(56) References Cited

U.S. PATENT DOCUMENTS

| | | |
|---|---|---|
| 5,846,701 A | 12/1998 | Kacian et al. |
| 5,871,975 A | 2/1999 | Kacian et al. |
| 5,876,992 A | 3/1999 | De Rosier et al. |
| 6,127,155 A | 10/2000 | Gelfand et al. |
| 6,150,094 A | 11/2000 | Maier et al. |
| 6,242,235 B1 | 6/2001 | Shultz et al. |
| 6,617,136 B2 | 9/2003 | Parthasarathy et al. |
| 6,740,510 B2 | 5/2004 | Kautzer et al. |
| 6,767,723 B2 | 7/2004 | Tonoike |
| 7,094,539 B2 | 8/2006 | Gu et al. |
| 7,422,882 B2 | 9/2008 | Kuroita et al. |
| 7,425,423 B1 | 9/2008 | Ankenbauer et al. |
| 7,638,276 B2 | 12/2009 | Griffiths et al. |
| 7,803,929 B2 | 9/2010 | Melkonyan et al. |
| 7,846,703 B2 | 12/2010 | Kobayashi et al. |
| 7,972,828 B2 | 7/2011 | Ward et al. |
| 7,973,154 B2 | 7/2011 | Melkonyan et al. |
| 8,012,685 B2 | 9/2011 | Shannon et al. |
| 8,173,401 B2 | 5/2012 | Chang et al. |
| 8,192,960 B2 | 6/2012 | Peters et al. |
| 8,202,972 B2 | 6/2012 | Nelson et al. |
| 8,404,464 B2 | 3/2013 | Ward et al. |
| 8,460,934 B2 | 6/2013 | Chang et al. |
| 8,980,333 B2 | 3/2015 | Angrish et al. |
| 9,493,414 B2 | 11/2016 | Angrish et al. |
| 9,567,628 B2 | 2/2017 | Wang et al. |
| 2002/0127587 A1 | 9/2002 | Simms et al. |
| 2002/0168658 A1 | 11/2002 | Weissman et al. |
| 2003/0017567 A1 | 1/2003 | Parthasarathy et al. |
| 2003/0022231 A1 | 1/2003 | Wangh et al. |
| 2003/0108919 A1 | 6/2003 | Kautzer et al. |
| 2005/0037392 A1 | 2/2005 | Griffiths et al. |
| 2005/0277121 A1 | 12/2005 | Pasloske et al. |
| 2006/0068390 A1 | 3/2006 | Tillett et al. |
| 2006/0160122 A1 | 7/2006 | Harrold et al. |
| 2006/0234228 A1 | 10/2006 | Oshima et al. |
| 2006/0292578 A1 | 12/2006 | Zheng et al. |
| 2008/0003574 A1 | 1/2008 | Michalik et al. |
| 2008/0003575 A1 | 1/2008 | Michalik et al. |
| 2008/0064071 A1 | 3/2008 | Hogrefe et al. |
| 2008/0145910 A1 | 6/2008 | Ward et al. |
| 2008/0166772 A1 | 7/2008 | Hollinger et al. |
| 2008/0199857 A1 | 8/2008 | Lee |
| 2009/0111149 A1 | 4/2009 | Cao |
| 2009/0155777 A1 | 6/2009 | Yang et al. |
| 2009/0325236 A1 | 12/2009 | Griffiths et al. |
| 2010/0035238 A1 | 2/2010 | Westberry et al. |
| 2010/0099150 A1 | 4/2010 | Fang et al. |
| 2010/0159528 A1 | 6/2010 | Liu et al. |
| 2011/0015379 A1 | 1/2011 | Mori et al. |
| 2011/0046205 A1 | 2/2011 | Kosak et al. |
| 2011/0171717 A1 | 7/2011 | Kobayashi et al. |
| 2011/0236891 A1 | 9/2011 | Li et al. |
| 2011/0287436 A1 | 11/2011 | Shannon et al. |
| 2012/0202700 A1 | 8/2012 | Pierson et al. |
| 2012/0302449 A1 | 11/2012 | Dong et al. |
| 2012/0322066 A1 | 12/2012 | Angrish et al. |
| 2013/0066062 A1 | 3/2013 | Sano et al. |
| 2013/0084574 A1 | 4/2013 | Dong et al. |
| 2015/0184145 A1 | 7/2015 | Angrish et al. |

FOREIGN PATENT DOCUMENTS

| | | |
|---|---|---|
| EP | 0258017 B1 | 6/1997 |
| EP | 0455430 B1 | 7/1998 |
| EP | 0506825 B1 | 8/1998 |
| EP | 0550687 B1 | 6/1999 |
| EP | 0550696 B1 | 11/2000 |
| EP | 0624641 B1 | 12/2000 |
| EP | 0632134 B1 | 9/2001 |
| EP | 0671473 B1 | 10/2001 |
| EP | 0544789 B1 | 3/2003 |
| EP | 0892058 B1 | 5/2006 |
| EP | 0931151 B1 | 11/2006 |
| EP | 1390545 B1 | 11/2006 |
| EP | 1507002 B1 | 12/2006 |
| EP | 1050587 B1 | 4/2007 |
| EP | 1088060 B1 | 5/2007 |
| EP | 1522582 B1 | 7/2007 |
| EP | 1458744 B1 | 8/2007 |
| EP | 1482036 B1 | 10/2007 |
| EP | 0776970 B1 | 4/2008 |
| EP | 1505151 B1 | 5/2008 |
| EP | 1718743 B1 | 8/2009 |
| EP | 1154017 B1 | 1/2010 |
| EP | 1772523 B1 | 1/2010 |
| EP | 2175020 A1 | 4/2010 |
| EP | 1904518 B1 | 10/2010 |
| EP | 1842922 B1 | 5/2011 |
| EP | 2333102 A1 | 6/2011 |
| EP | 1540009 B1 | 9/2011 |
| EP | 1905828 B1 | 8/2012 |
| EP | 0894860 B1 | 12/2012 |
| EP | 1908832 B1 | 12/2012 |
| EP | 2314596 B1 | 6/2013 |
| EP | 2115131 B1 | 7/2013 |
| GB | 1087415 | 10/1967 |
| JP | 60-089458 A | 5/1985 |
| JP | H05178731 A | 7/1993 |
| JP | H061712 A | 1/1994 |
| JP | H061715 A | 1/1994 |
| RO | 83776 | 3/1984 |
| WO | 1998044161 A1 | 10/1998 |
| WO | 2008/013885 A2 | 1/2008 |
| WO | 2008/033936 A2 | 3/2008 |
| WO | 2008144556 A1 | 11/2008 |
| WO | 2010002938 A2 | 1/2010 |
| WO | WO-2011046972 A2 | 4/2011 |
| WO | 2011163120 A1 | 12/2011 |
| WO | 2012146980 A2 | 11/2012 |
| WO | 2012170907 A2 | 12/2012 |
| WO | 2012170908 A1 | 12/2012 |
| WO | 2013050881 A2 | 4/2013 |

OTHER PUBLICATIONS

Extended European Search Report for Application No. 19158407.7, dated Jun. 27, 2019, 5 pages.

Al-Soud, et al., "Effects of amplification facilitators on diagnostic PCR in the presence of blood, feces, and meat", Journal of Clinical Microbiology, Dec. 2000, 4463-4470.

Fu, X., et al., "Waste recombinant DNA: Effectiveness of thermo-treatment to manage potential gene pollution", Environmental Pollution, Aug. 1, 2009, 2536-2541.

Goswami, Lalit, et al., "Efficient synthesis of diverse heterobifunctional-ized clickable oligo(ethylene glycol) linkers: potential applications in bioconjugation and targeted drug delivery", Organic & Biomolecular Chemistry, 2013, 1116-1126.

Hunter, S., et al., "The QPCR assay for analysis of mitochondrial DNA damage, repair, and relative copy number", Methods: A Companion to Methods in Enzymology, Aug. 1, 2010, 444-451.

Kreader, Carol A., et al., "Relief of Amplification Inhibition in PCR with Bovine Serum Albumin or T4 Gene 32 Protein", Applied and Environmental Microbiology, Mar. 1996, 1102-1106.

Moppett, J., et al., "Inhibition affecting RQ-PCR-based assessment of minimal residual disease in acute lymphoblastic leukemia: reversal by addition of bovine serum albumin", Leukemia, Jan. 1, 2003, 268-270.

Nagai, et al., "Additive Effects of Bovine Serum Albumin, Dithiothreitol, and Glycerol on PCR", Biochemistry and Molecular Biology International, Jan. 1, 1998, 157-163.

Nakamura, et al., "English Abstract JP6001712", Chemical Abstracts Service, Jan. 11, 1994, 3 pages.

Nakamura, et al., "English Abstract JP6001715", Chemical Abstracts Service, Jan. 11, 1994, 2 pages.

Nakamura, et al., "English Abstract JP60089458", Chemical Abstract Service, May 20, 1985, 4 pages.

Nakamura, et al., "English Abstract JP6049440", Chemical Abstracts Service, Feb. 22, 1994, 1 pages.

(56) References Cited

OTHER PUBLICATIONS

PCT/US2012/041687, International Search Report and Written Opinion dated Jan. 11, 2013, 25 pages.
PCT/US2012/041688, Notification of Transmittal of the International Search Report and the Written Opinion of the International Searching Authority, or the Declaration, dated Oct. 19, 2012, 14 pages.
PCT/US2014/062222, International Search Report and Written Opinion dated Dec. 22, 2014, 9 pages.
Provencher-Mandeville, Josee, et al., "Synthesis of 17β-estradiol-platinum(II) hybrid molecules showing cytotoxic activity on breast cancer cell lines", Bioorganic & Medicinal Chemistry Letters, vol. 18, 2008, 2282-2287.
Schomaker, Jennifer, et al. , "Diastereomerically and Enantiomerically Pure 2,3-Disubstituted Pyrrolidines from 2,3-Aziridin-1-ols Using a Sulfoxonium Ylide: A One-Carbon Homologative Relay Ring Expansion", Journal of the American Chemical Society, vol. 129, S14, 2007, 1996-2003.
STN Abstract: Nakamura, et al., JP Pat. No. 4060102 B issued, Sep. 25, 1992.
Wang, Mei-Yun, et al., "Improving PCR and qPCR detection of hydrogenase A (hydA) associated with Clostridia in purge cultures and environmental sludges using bovine serum albumin", Applied Microbiology and Biotechnology, Oct. 2, 2007, 645-656.
Wang, Xiangcheng, et al., "An Improved Method of Synthesis of 5-Deoxy-D-ribose", Chemical World, vol. 4, 2008, 226-228.

Titration of Dt1 and Dt2 using Rhodopsin gene primer (~4Kb product)

Detergent Derivative Dt4 Compared to Tween20

Detergent Derivative Dt4 Compared to Tween20 – log scale

Detergent Derivative Dt4 Compared to Tween20

COMPOUNDS FOR USE IN PCR SYSTEMS AND APPLICATIONS THEREOF

CROSS-REFERENCE TO RELATED APPLICATIONS

This application is a divisional of U.S. application Ser. No. 14/523,410, filed Oct. 24, 2014, which claims the benefit under 35 U.S.C. § 119(e) of U.S. Provisional Application No. 61/895,876, filed Oct. 24, 2013. The entire contents of the aforementioned applications are incorporated by reference herein.

FIELD

This disclosure relates to novel compounds for use in various compositions, kits and methods including, for example, compositions and methods relating to nucleic acid synthesis such in polymerase storage buffers or in reactions such as the polymerase chain reaction (PCR). Methods for preparing the modified compounds are also described.

BACKGROUND

Many widely known recombinant DNA techniques involve replicating or polymerizing and/or amplifying DNA. One such example is the polymerase chain reaction (PCR). During PCR, the reaction cycles repeatedly between two temperatures, a low and a high temperature (e.g., 55° C. and 95° C.) in the presence of a thermostable DNA polymerase enzyme. The total period of time spent at the high temperature over the course of the reaction depends upon the total number of cycles, the duration of the high temperature step of each cycle, and the ramp speed (i.e., the rate at which the thermocycler changes from one temperature to another). Although the DNA polymerases used in PCR are highly thermostable, they tend to become inactive at high temperatures over time. Furthermore, these polymerases may also become inactive by being introduced into reaction mixture environments with sub-optimal concentration of cofactors, or that have sub-optimal pH levels, or that include the presence of chemical or biological inhibitors.

One way of stabilizing an enzyme under such conditions is to add a stabilizing agent, such as a surfactant. Surfactants, such as detergents, are surface-active compounds that stabilize the interface between the active form of an enzyme and its liquid environment. For example, the activity of Taq DNA polymerase has been stabilized by the addition of nonionic detergents, such as NP-40 or Tween® 20 (Bachmann, et al. *Nuc. Acids Res.* 18(5): 1309 (1990)). In some applications, however, Tween® 20-stabilized DNA polymerases have low efficiencies of amplification or lead to the amplification of non-specific products. In addition, some detergents are required a high concentrations. Moreover, some detergents (e.g., NP-40) are also known to have toxic properties. There is a need, therefore, for compounds that improve the stability of thermostable DNA polymerases in solution, and particularly compounds that improve enzyme stability without imparting any of the disadvantages of currently used detergents.

BRIEF DESCRIPTION OF THE DRAWINGS

All amplification plots shown herein graphically represent target nucleic acid amplification as ΔRn (y-axis) as a function of cycle number (x-axis).

SUMMARY

Figure 1:
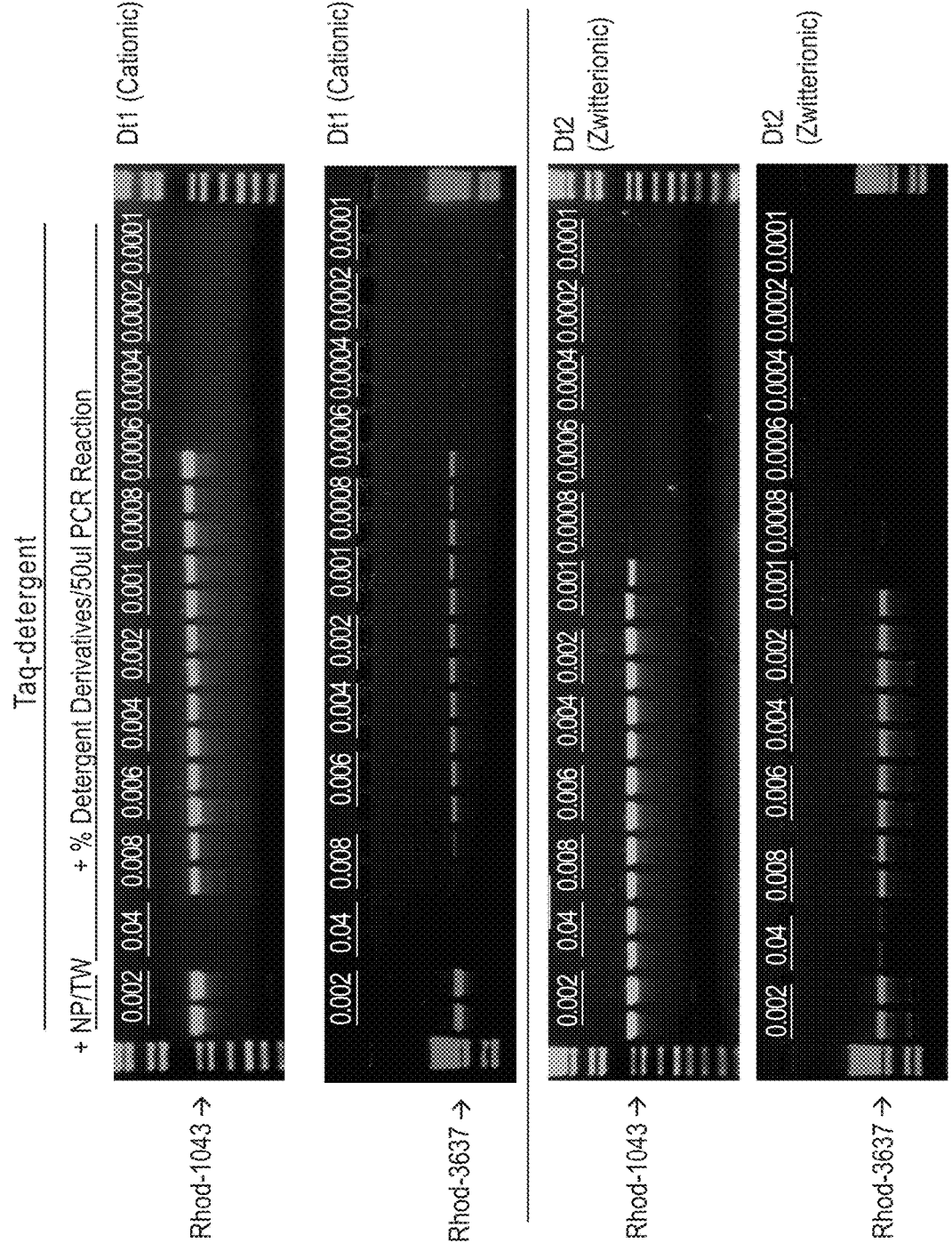
FIG. 1. Titration of novel compounds Dt1 and Dt2 at different concentrations using 1 Kb and 3 Kb PCR products amplified according to certain exemplary embodiments of the methods and compositions disclosed herein.

Provided herein are novel compounds for a variety of compositions, kits and methods. Such uses may include, but are not limited to use in storage buffers and nucleic acid synthesis or amplification reactions. In some embodiments, ionic and zwitterionic detergent compounds synthesized by chemically modifying relevant starting materials are provided.

In some embodiments, such novel compounds are in composition with a thermostable polymerase. In some embodiments, such compositions are stabilized thermostable enzyme compositions. In one embodiment the enzyme is DNA polymerase purified from *Thermus aquaticus* (Taq polymerase). In some embodiments the enzyme is a DNA polymerase produced by recombinant means. In another embodiment, the enzyme is a DNA polymerase combined with an antibody (or antibodies) and/or an oligonucleotide that can reversibly inhibit said polymerase.

The novel compounds provided herein may be used for a variety of uses and may be included in various compositions, such as, for example, nucleic acid amplification reactions such as a polymerase chain reaction (PCR).

In certain embodiments, the modified compounds have the following structural formula:

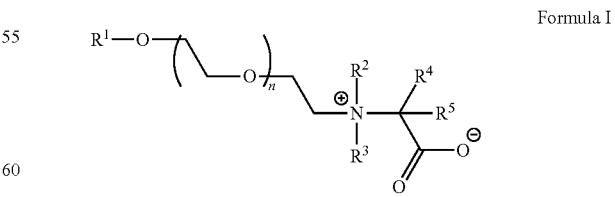

Formula I wherein:
R$^1$ is H, (C$_1$-C$_{30}$) alkyl, (C$_1$-C$_{30}$) substituted alkyl, (C$_1$-C$_{30}$) heteroalkyl, (C$_1$-C$_{30}$) substituted heteroalkyl, aryl, substituted aryl, heteroaryl, substituted heteroaryl, phenyl, substituted phenyl, where the substituted aryl or substituted phenyl is substituted by at least one ($C_1$-$C_{30}$) alkyl, ($C_1$-$C_{30}$) substituted alkyl, ($C_1$-$C_{30}$) heteroalkyl, or ($C_1$-$C_{30}$) substituted heteroalkyl;

$R^2$ and/or $R^3$ are each independently H, $CH_3$, $CH(CH_3)_2$, $CH_2(C_6H_5)$, or $C(CH_3)_3$;

$R^4$ and/or $R^5$ are each independently H, $CH_3$, $CH(CH_3)_2$, $C_6H_5$, $CH_2(C_6H_5)$, $C(CH_3)_3$, $CH_2CH(CH_3)_2$, $CHCH_2CH(CH_3)_2$, $CH_2C_6H_5OH$, $CH_2C$≡$CH$ $NH(C_6H_5)$, $CH_2C$≡$CHN$≡$CHNH$, $CH_2COOH$, $CH_2CONH_2$, $(CH_2)_2CONH_2$, $(CH_2)_2COOH$, $CH_2SH$, $(CH_2)_nNH$, $(CH_2)_nN$, $CH_2OH$, $CH(OH)CH_3$, $(CH_2)_2SCH_3$, $(CH_2)_3NHC(NH_2)$=$NH$, or, alternatively, $R^3$ is taken together with $R^5$ to form a 5- or 6-membered ring which is optionally substituted with at least one ($C_1$-$C_{30}$) alkyl, ($C_1$-$C_{30}$) substituted alkyl, ($C_1$-$C_{30}$) heteroalkyl, ($C_1$-$C_{30}$) substituted heteroalkyl; and, each n is independently any positive integer, including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

In certain embodiments, $R^1$ is a $C_8$ alkyl. In certain embodiments, $R^1$ is a $C_{12}$ alkyl. In other embodiments, $R^1$ is a $C_{16}$ alkyl. In certain embodiments, $R^2$ and/or $R^3$ are each independently selected from H and $CH_3$. In certain embodiments, $R^4$ and/or $R^5$ are each independently selected from H, $(CH_2)_nNH$, $(CH_2)_nN$, or alternatively, $R^3$ is taken together with $R^5$ to form a 5- or 6-membered ring.

In certain embodiments, a novel compound of Formula 1 is provided. In some embodiments, the novel compound BrijL-23-Proline having the following structural formula:

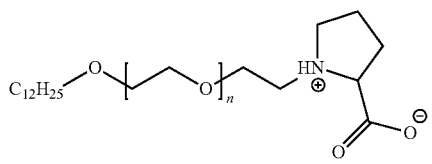

BrijL-23-Proline and/or derivatives thereof are provided.

Also provided are the methods for polymerizing and/or amplifying a nucleic acid comprising mixing a target nucleic acid with at least one polymerase, a primer, dNTPs, and at least one novel compound of Formula I, and polymerizing and/or amplifying the target nucleic acid. In some embodiments of such methods, at least one primer is utilized. In certain embodiments, a nucleic acid amplification reaction mixture comprising at least one polymerase, dNTPs, at least one primer, and at least one novel compound of Formula I is provided. In some embodiments, the reaction mixture may further comprise a detectable label. In certain embodiments, the methods further include one or more steps for detecting the detectable label to quantitate the amplified nucleic acid. In certain embodiments, methods for inhibiting inactivation of a polymerase during a thermal cycling process by including therein a novel detergent of Formula I are provided. In certain embodiments, methods for providing an enzyme having polymerase activity and at least one novel detergent of Formula I and combining the same to form a mixture under conditions such that the polymerase activity of the enzyme is stabilized are provided. In certain embodiments, the polymerase is thermostable. In certain embodiments, the methods described herein provide amplification reactions with amplification efficiency similar to (e.g., approximately the same), or increased amplification efficiency when in the presence of a conventional (e.g., known) detergent such as, for example, NP-40 and/or Tween® 20. In some embodiments, the novel compounds described herein may substitute for NP-40 and/or Tween® 20, for example, in a storage buffer or an amplification reaction (e.g., as provided as part of a master mix or premixed composition).

In certain embodiments, the effective concentration of the at least one novel compound described herein in a composition or reaction mixture is equal to or less than that required of conventional detergents such as NP-40 and/or Tween® 20. In some such embodiments, the effective concentration of the at least one novel compound(s) in a reaction mixture may be up to, about, or at least one, two, three, four, five, six, seven, eight, nine, or ten times less than that required of conventional detergent(s) such as NP-40 and/or Tween® 20. In some embodiments, the effective concentration of the at least one novel compound, such as BrijL-23-Proline is from 0.0001% to 10%. For example, in some embodiments, the concentration of BrijL-23-Proline in a composition or reaction mixture is 0.0001%, 0.001%, 0.01%, 0.1%, 1%, or 10%. In some preferred embodiments, the concentration of BrijL-23-Proline in said composition or reaction mixture is 0.01% to 5%, such as 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, and 5%.

Methods for producing the novel compounds are also provided.

In certain embodiments, compositions comprising at least one of the novel compounds of Formula I, such as BrijL-23-Proline, are provided herein. In certain embodiments, compositions comprising at least one polymerase and at least one of the novel compounds of Formula I, such as BrijL-23-Proline, are provided. In some embodiments, the polymerase is thermostable. Kits comprising reagents including such compounds and the like necessary to carry out such methods or prepare such mixtures are also provided.

DETAILED DESCRIPTION

Provided herein are novel compounds for a variety of uses, including but not limited to use in compositions used for stable enzyme storage and/or nucleic acid polymerization and/or amplification reactions. Thus, in some embodiments, compositions, methods, and kits for storage of polymerases and for amplifying target nucleic acids are provided. In some embodiments, ionic and zwitterionic detergents are synthesized chemically utilizing starting compounds (e.g., simpler compounds) are provided. In some embodiments, the novel compounds such as Dt1, Dt2, Dt3, Dt4, Dt5, Dt6, Dt7, Dt8, Dt9, Dt10, Dt11 and Dt12 (described below) are provided. In some embodiments, the novel compound BrijL-23-Proline is provided. These novel compounds may be used in a variety of procedures including, for example, nucleic acid polymerization and/or amplification reactions such as the polymerase chain reaction (PCR). In some embodiments, the presence of one or more of the novel compounds of Formula I, such as BrijL-23-Proline, may stabilize the polymerase within a composition or a reaction mixture, decrease inhibition of the polymerase within a composition or reaction mixture, and/or increase the polymerization and/or amplification efficiency of the polymerase within a reaction mixture. As such, compositions and reaction mixtures comprising at least one polymerase and at least one of the novel compounds of Formula I, such as BrijL-23-Proline, are provided. Such compositions or reaction mixtures may further comprise one or more dNTPs and at least one nucleic acid amplification primer (e.g., PCR primer). In some embodiments, such compositions may also include one or more components, such as Tris, EDTA, glycerol, DTT, KCl, $Mg^{2+}$, gelatin (e.g., fish gelatin), Kathon, or bovine serum albumin (BSA).

In certain embodiments, compositions comprising at least one of the novel compounds of Formula I are provided herein. In certain embodiments, compositions comprising at least one polymerase and at least one of the novel compounds of Formula I are provided. In some embodiments, the polymerase is thermostable. Kits comprising the components of such reaction mixtures and optionally also other reagents necessary for carrying out such methods or for preparing such mixtures are also provided (either individually or as a pre-mixed formulation).

Novel compounds and methods of preparing and using the same are described herein. The term "novel compounds" typically refers to a compound of Formula I. In certain embodiments, the term "detergent" may refer to one or more novel compounds, optionally including one or more "conventional detergents." As used herein, the term "conventional detergent" may refer to a know compound and/or any compounds other than those described herein under Formula I. In some embodiments, the term "novel compound" may refer to a novel compound only, or a combination of one or more novel compounds with one or more conventional additives, such as detergents. Similarly, the use of the term "at least one novel compound" may refer to one or more novel compounds alone, with another novel compound, and/or with one or more conventional additives, such as detergents. Thus, in some embodiments, the compositions and/or reaction mixtures described herein may further comprise one or more conventional detergents such as, for example and without limitation, a nonionic detergent, Brij-58, CHAPS, n-Dodecyl-b-D-maltoside, NP-40, sodium dodecyl sulphate (SDS), TRITON® X-15, TRITON® X-35, TRITON® X-45, TRITON® X-100, TRITON® X-102, TRITON® X-114, TRITON® X-165, TRITON® X-305, TRITON® X-405, TRITON® X-705, Tween® 20 and/or ZWITTERGENT®. Other detergents may also be suitable, as may be determined by one of skill in the art (see, e.g., U.S. Patent Application Publication No. 2008/0145910; U.S. Patent Application Publication No. 2008/0064071; U.S. Pat. Nos. 6,242,235; 5,871,975; and 6,127,155 for exemplary detergents; all of which are hereby incorporated herein by reference in their entirety.) Additional detergents may also be suitable, as would be determined by the skilled artisan.

In certain embodiments, the novel compounds have the following structural formula:

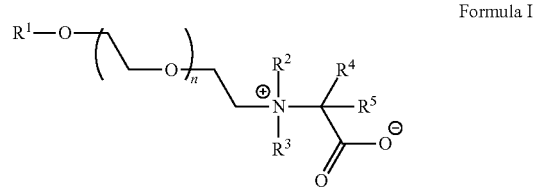

Formula I wherein:
R¹ is H, $(C_1-C_{30})$ alkyl, $(C_1-C_{30})$ substituted alkyl, $(C_1-C_{30})$ heteroalkyl, $(C_1-C_{30})$ substituted heteroalkyl, aryl, substituted aryl, heteroaryl, substituted heteroaryl, phenyl, substituted phenyl, where the substituted aryl or substituted phenyl is substituted by at least one $(C_1-C_{30})$ alkyl, $(C_1-C_{30})$ substituted alkyl, $(C_1-C_{30})$ heteroalkyl, or $(C_1-C_{30})$ substituted heteroalkyl;

R² and/or R³ are each independently H, $CH_3$, $CH(CH_3)_2$, $CH_2(C_6H_5)$, or $C(CH_3)_3$;

R⁴ and/or R⁵ are each independently H, $CH_3$, $CH(CH_3)_2$, $C_6H_5$, $CH_2(C_6H_5)$, $C(CH_3)_3$, $CH_2CH(CH_3)_2$, $CHCH_2CH(CH_3)_2$, $CH_2C_6H_5OH$, $CH_2C=CH$ $NH(C_6H_5)$, $CH_2C=CHN=CHNH$, $CH_2COOH$, $CH_2CONH_2$, $(CH_2)_2CONH_2$, $(CH_2)_2COOH$, $CH_2SH$, $(CH_2)_nNH$, $(CH_2)_nN$, $CH_2OH$, $CH(OH)CH_3$, $(CH_2)_2SCH_3$, $(CH_2)_3NHC(NH_2)=NH$, or, alternatively, R³ is taken together with R⁵ to form a 5- or 6-membered ring which is optionally substituted with at least one $(C_1-C_{30})$ alkyl, $(C_1-C_{30})$ substituted alkyl, $(C_1-C_{30})$ heteroalkyl, $(C_1-C_{30})$ substituted heteroalkyl; and, each n is independently any positive integer, including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

In certain embodiments, R¹ is a $C_8$ alkyl. In certain embodiments, R¹ is a $C_{12}$ alkyl. In other embodiments, R¹ is a $C_{16}$ alkyl. In certain embodiments, R² and/or R³ are each independently selected from H and $CH_3$. In certain embodiments, R⁴ and/or R⁵ are each independently selected from H, $(CH_2)_nNH$, $(CH_2)_nN$, or alternatively, R³ is taken together with R⁵ to form a 5- or 6-membered ring.

In certain embodiments, R¹ is a $C_{12}$ alkyl. In certain embodiments, R² and R⁴ are H. In certain embodiments, R³ is taken together with R⁵ to form a 5-membered ring, and each n is independently any positive integer, including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

In certain embodiments, the novel compound is BrijL-23-Proline and/or derivatives thereof. In certain embodiments, the novel compound has the following structural formula:

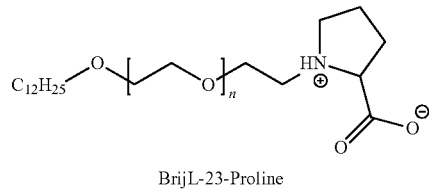

BrijL-23-Proline

The compounds of Formula I may be prepared by utilizing simpler starting compound material to provide new and/or improved compounds (e.g., surfactants or detergents) and its properties thereto. In some embodiments, the intermediates can be analyzed using LC-MS analysis and used without purification to perform the next synthesis step.

In some embodiments, a stable enzyme composition comprising the novel compounds described herein and an enzyme are provided. In some embodiments, the enzyme is a DNA or RNA polymerase. In some embodiments, the enzyme is thermostable. In some embodiments, the enzyme is purified. In some embodiments, the enzyme is native. In some embodiments, the enzyme is recombinant. In some embodiments the DNA polymerase is a thermostable DNA polymerase. In some embodiments, the DNA polymerase is isolated from *Thermus aquaticus*. In some embodiments, the enzyme may be a fusion protein, such as a fusion polymerase. In some embodiments, the novel compounds described herein and the enzyme are provided in a buffer. In some embodiments the buffer comprises one or more components such as nucleotide triphosphates (dNTPs), MgCl2+, DTT, EDTA, Tris, glycerol, KCl, gelatin, and Kathon. In some preferred embodiments, the concentration of said nucleotide triphosphates is M about 0.15 mM to 2 mM (e.g., 0.4 mM) each. In some preferred embodiments, the concentration of said MgCl2+ is about 1 to 15 mM (e.g, 3 mM). In some preferred embodiments, the concentration of said DTT is about 0.5 to 5 mM (e.g, 1 mM). In some preferred embodiments, the concentration of said EDTA is about 0.05 to 1 mM (e.g, 0.1 mM or 0.15 mM). In some preferred embodiments, the concentration of said Tris is about 5 mM to 500 mM (e.g, 20 mM, 30 mM, 40 mM, 200 mM or 300 mM). In some preferred embodiments, the pH of said Tris is about 7.5 to 8.5. In some preferred embodiments, the concentration of said glycerol is about 10% to 60% (e.g, 30%, 35%, 40%, 45% or 50%). In some preferred embodiments, the concentration of said KCl is about 50 mM to 1000 mM (e.g, 100 mM or 500 mM). In some preferred embodiments, the concentration of said gelatin is about 0.02% to 1% (e.g, 0.05% or 0.5%). In some preferred embodiments, the concentration of said Kathon is about 0.015% to 0.05% (e.g, 0.016% or 0.04%). In some embodiments, an enzyme inhibitor is further provided, such as those described herein.

In some embodiments, an enzyme, such as a thermostable DNA polymerase, is stored in compositions comprising the novel compounds described herein (e.g., BrijL-23-Proline). In some embodiments, the enzyme is stable for extended periods of time. For example, in some embodiments, the enzyme is stored in compositions comprising the novel compounds described herein for at least one, two, three, four, five, ten, 16, 24, 30 or 36 months. In some embodiments, the enzyme is stored in compositions comprising the novel compounds described herein at temperatures from about −70° C. to about ambient temperature (e.g., 25° C.). In some embodiments, the enzyme is stored in compositions comprising the novel compounds described herein at about 4° C., −4° C. or −20° C.

In some embodiments, methods for preparing the novel compounds described herein are provided. In some embodiments, such methods can include sequentially combining Compound A (as shown in Process 1) (e.g., 1 eq), methyltriphenoxyphosphonium iodide (e.g., 4 eq.), and N,N-dimtheyl formamide (DMF) (e.g., 6 mL) to an aluminum foil covered round bottom flask (e.g., 50 mL). The reaction is then stirred for a sufficient period of time (e.g., 3 days) under an appropriate atmosphere (e.g., argon) at an appropriate temperature (e.g., room temperature). After the sufficient period of time (e.g., 3 days), progress of the reaction may be monitored (e.g., using analytical liquid chromatography/mass spectrometry (LC-MS). The appearance of an intermediate product pattern may confirm formation of the modified detergent. This expected intermediate product (Intermediate B) may or may not (typical) be isolated. To this intermediate product, amino acid ester hydrochloride salt (e.g., 2 eq.) and Et₃N (e.g., 2 eq.) may be added. The reaction mixture may be heated for an appropriate period of time (e.g., 3-4 days) at an appropriate temperature (e.g., 65° C.). The progress of the reaction may be monitored using analytical LC-MS. The reaction mixture is then typically cooled to an appropriate temperature (e.g., room temperature) and concentrated (e.g., on a rotovapor) to appropriate volume (e.g., approximately 2 mL). The concentrated crude mixture may then be purified by preparative HPLC. The desired fractions may then be pooled and concentrated (e.g., on the rotovapor) to afford the desired product (e.g., as in Process 1 to produce the compounds Dt1, Dt3, Dt5, Dt7, Dt9, Dt11, and Dt12). This product may then be subjected to a hydrolysis reaction (e.g., using 2N NaOH). The reaction mixture may then be stirred (e.g., at room temperature) until all the starting material is consumed as determined by analytical LC-MS. This may be followed by neutralization (e.g., with Amberlite) to produce the final cationic products (e.g., Dt1, Dt3, Dt5, Dt7, Dt9, Dt11, and Dt12), zwitterionic products (e.g., Dt2, Dt4, Dt6, Dt10) or anionic product (Dt8).

Thus, an exemplary method for the development of the novel compounds of Formula I is shown below:

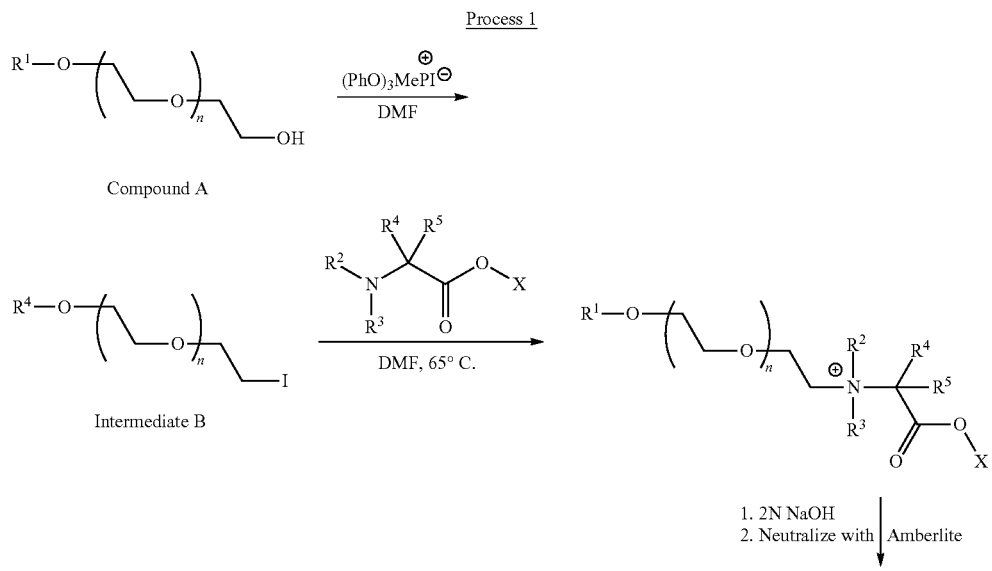

-continued

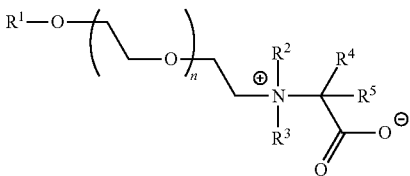

Zwitterionic where $R^1$, $R^2$, $R^3$, $R^4$, $R^5$ and n are as described hereinabove, and X is selected from the group consisting of H, $CH_3$, $CH_2CH_3$, $CH_2(C_6H_5)$, and $C(CH_3)_3$. The novel compounds of Formula I may be, for example, ionic (e.g., cationic, anioinic, zwitterionic). Exemplary novel compounds made using Process 1 are shown below:

Dt1
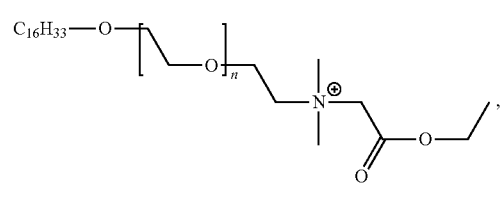

Dt2
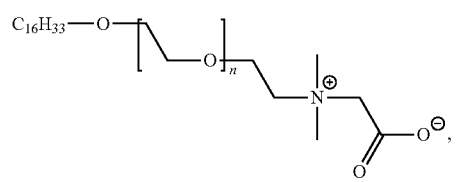

Dt3
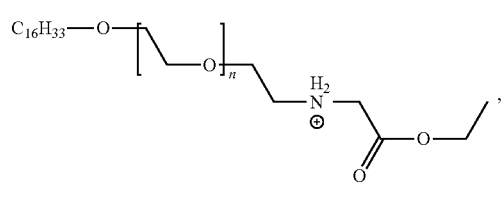

Dt4
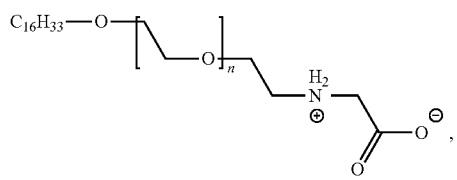

Dt5
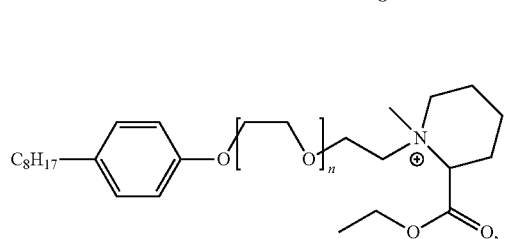

Dt6
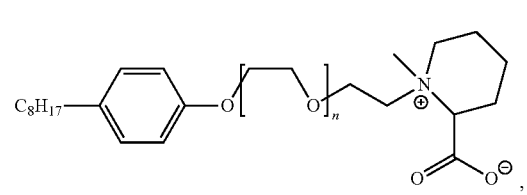

-continued

Dt7
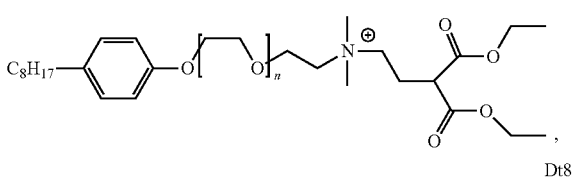

Dt8
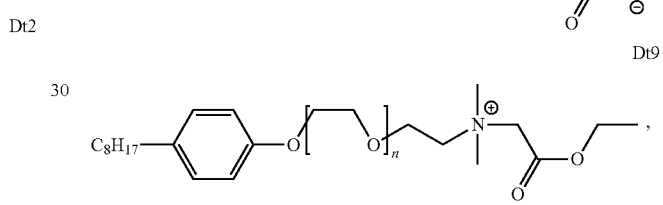

Dt9
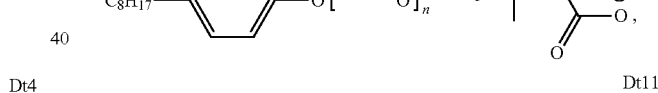

Dt10
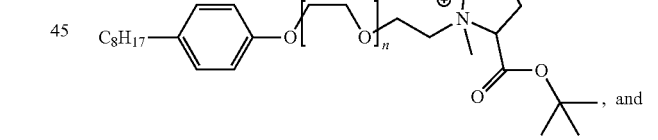

Dt11, and Dt12
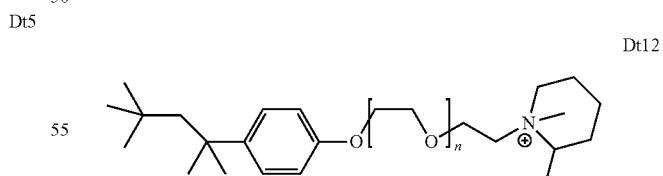

where n is as described hereinabove. In certain embodiments, each n is independently 5, 6, 7, 8, 9, 10, 15, 20, 25 or 30.

An exemplary method for the development of novel compounds, using Process 2 is shown below.

Process 2

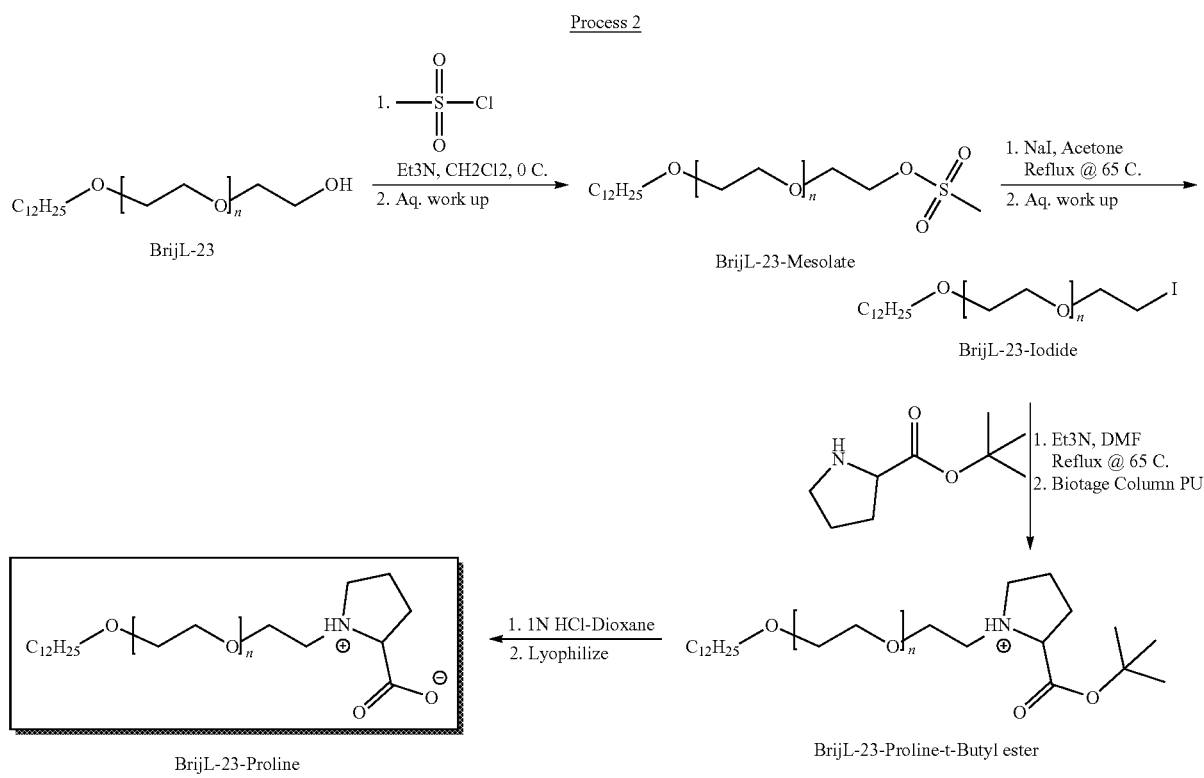

An exemplary novel compound of Formula I, BrijL-23-Proline, made using Process 2 is shown above as a final product (see compound in box).

Additional information regarding the reactants and intermediates of Process 2, and the novel compound prepared thereby, is shown in Table 1:

of Formula I, such as BrijL-23-Proline, is provided. In certain embodiments, the compositions and/or reaction mixtures may further comprise a detectable label. In certain embodiments, the methods include one or more steps for detecting and/or quantitating the detectable label to detect and/or quantitating the amplified nucleic acid.

TABLE 1

| Common Name | Chemical Name |
| --- | --- |
| BrijL-23 | Polyoxyethylene(23) lauryl ether or 3,6,9,12,15,18,21,24,27,30,33,36,39,42,45,48,51,54,57,60,63,66,69-Tricosaoxahenoctacontan-1-ol |
| BrijL-23-Mesolate | Poly(oxy-1,2-thanediyl)α-dodecyl-ω-hydroxy-methanesulfonate or 3,6,9,12,15,18,21,24,27,30,33,36,39,42,45,48,51,54,57,60,63,66,69-tricosaoxahenoctacontyl methanesulfonate |
| BrijL-23-Iodide | Poly(oxy-1,2-thanediyl)α-dodecyl-ω-hydroxy-iodide or 1-iodo-3,6,9,12,15,18,21,24,27,30,33,36,39,42,45,48,51,54,57,60,63,66,69-tricosaoxahenoctacontane |
| BrijL-23-Proline-t-butyl ester | Poly(oxy-1,2-ethanediyl)α-dodecyl-ω-hydroxy-L-Proline-t-butyl ester or tert-butyl-1-(3,6,9,12,15,18,21,24,27,30,33,36,39,42,45,48,51,54,57,60,63,66,69-tricosaoxahenoctacontyl) pyrrolidine-2-carboxylate |
| BrijL-23-Proline | Poly(oxy-1,2-ethanediyl)α-dodecyl-ω-hydroxy-L-proline or 1-(3,6,9,12,15,18,21,24,27,30,33,36,39,42,45,48,51,54,57,60,63,66,69-tricosaoxahenoctacontyl)pyrrolidine-2-carboxylic acid |

In certain embodiments methods for polymerizing and/or amplifying a nucleic acid comprising mixing a target nucleic acid with at least one polymerase, a primer, dNTPs, and at least one novel compound of Formula I, and polymerizing and/or amplifying the target nucleic acid are provided. In certain embodiments, the methods may include at least one primer. In certain embodiments, a nucleic acid amplification reaction mixture comprising at least one polymerase, dNTPs, at least one primer, and at least one novel compound In certain embodiments methods for inhibiting inactivation of a polymerase during storage and/or a thermal cycling process by including therein a novel compound of Formula I are provided. In certain embodiments, methods for providing an enzyme having polymerase activity and at least one novel compound of Formula I and combining the same to form a mixture under conditions such that the polymerase activity of the enzyme is stabilized are provided. In certain embodiments, the polymerase is thermostable. In certain embodiments, the methods described herein provide compositions with enzyme stability similar to (e.g., approximately the same), or increased enzyme stability when in the presence of a conventional (e.g., known) detergent such as, for example, NP-40 and/or Tween® 20. In certain embodiments, the methods described herein provide amplification reactions with amplification efficiency similar to (e.g., approximately the same), or increased amplification efficiency when in the presence of a conventional (e.g., known) detergent such as, for example, NP-40 and/or Tween® 20. In some embodiments, the novel compounds described herein may substitute for NP-40 and/or Tween® 20 in storage buffer, master mix and/or amplification reaction.

In certain embodiments, the "effective concentration" (e.g., the amount that will support an amplification reaction such as PCR) of the at least one novel compound of Formula I (e.g., Dt1, Dt2, Dt3, Dt4, Dt5, Dt6, Dt7, Dt8, Dt9, Dt10, Dt11, Dt12 and/or BrijL-23-Proline) in a reaction mixture may be higher, the same, or lower than that required of conventional detergents (e.g., NP-40 and/or Tween® 20). In some such embodiments, the effective concentration of the at least one novel compound(s) (e.g., Dt4 and/or BrijL-23-Proline) in a reaction mixture may be up to about or at least one, two, three, four, five, six, seven, eight, nine, or ten times less than that required of conventional detergent(s) such as NP-40 and/or Tween® 20. For example, NP-40 or Tween® 20 are typically included in a reaction at about 0.01% or less (e.g., as determined by dilution from a stock solution into a reaction mixture). The novel compounds described herein may, in certain embodiments, be used at a lower concentration (e.g., as a percentage (i.e., w/v or v/v)) than conventional detergents (e.g., 0.002% for Dt4 as compared to 0.01% Tween® 20; See, for example, FIGS. 11A and 11B, FIGS. 12A and 12B, FIGS. 13A and 13B, FIGS. 14A and 14B, FIGS. 15A and 15B, FIG. 16, FIG. 17, and FIG. 18).

In certain embodiments, methods for polymerizing and/or amplifying a nucleic acid comprising mixing a nucleic acid of interest (e.g., a target nucleic acid) with at least one polymerase, a primer, dNTPs, and at least one novel compound of Formula I, and polymerizing and/or amplifying the target nucleic acid are provided. In certain embodiments, the methods include at least one primer. In certain embodiments, a nucleic acid amplification reaction mixture(s) comprising at least one polymerase, dNTPs, at least one primer, and at least one modified compound of Formula I is provided. In other embodiments, methods for using such mixture(s) are provided. Target nucleic acids may be amplified using any of a variety of reactions and systems.

As used herein, the terms "amplification," "nucleic acid amplification," or "amplifying" refer to the production of multiple copies of a nucleic acid template, or the production of multiple nucleic acid sequence copies that are complementary to the nucleic acid template. The terms (including the term "polymerizing") may also refer to extending a nucleic acid template (e.g., by polymerization). The amplification reaction may be a polymerase-mediated extension reaction such as, for example, a polymerase chain reaction (PCR). However, any of the known amplification reactions may be suitable for use as described herein. The term "amplifying" that typically refers to an "exponential" increase in target nucleic acid may be used herein to describe both linear and exponential increases in the numbers of a select target sequence of nucleic acid.

The term "amplification reaction mixture" and/or "master mix" may refer to an aqueous solution comprising the various (some or all) reagents used to amplify a target nucleic acid. Such reactions may also be performed using solid supports (e.g., an array). The reactions may also be performed in single or multiplex format as desired by the user. These reactions typically include enzymes, aqueous buffers, salts, amplification primers, target nucleic acid, and nucleoside triphosphates. Depending upon the context, the mixture can be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR, including quantitative PCR (qPCR) and end point PCR (epPCR), as the nucleic acid amplification reaction, it is expected that the modified detergents describe herein should be effective in other types of nucleic acid amplification reactions, including both polymerase-mediated amplification reactions (such as helicase-dependent amplification (HDA), recombinase-polymerase amplification (RPA), and rolling chain amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470). For example, the modified compounds may be used in, for example, various ligation-mediated reactions, where for example ligation probes are employed as opposed to PCR primers. Additional exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., PCT Publication No. WO 2006/081222), strand displacement (see, e.g., U.S. Pat. No. RE39007E), partial destruction of primer molecules (see, e.g., PCT Publication No. WO 2006/087574)), ligase chain reaction (LCR) (see, e.g., Wu, et al., *Genomics* 4: 560-569 (1990)), and/or Barany, et al. *Proc. Natl. Acad. Sci. USA* 88:189-193 (1991)), Q3 RNA replicase systems (see, e.g., PCT Publication No. WO 1994/016108), RNA transcription-based systems (e.g., TAS, 3SR), rolling circle amplification (RCA) (see, e.g., U.S. Pat. No. 5,854,033; U.S. Patent Application Publication No. 2004/265897; Lizardi et al. *Nat. Genet.* 19: 225-232 (1998); and/or Banér et al. *Nucleic Acid Res.*, 26: 5073-5078 (1998)), and strand displacement amplification (SDA) (Little, et al. *Clin. Chem.* 45:777-784 (1999)), among others. These systems, along with the many other systems available to the skilled artisan, may be suitable for use in polymerizing and/or amplifying target nucleic acids for use as described herein.

"Amplification efficiency" may refer to any product that may be quantified to determine copy number (e.g., the term may refer to a PCR amplicon, an LCR ligation product, and/or similar product). Whether a particular compound functions as desired in a particular amplification reaction may be determined by carrying out at least two separate amplification reactions, each reaction being carried out in the absence and presence, respectively, of a compound quantifying amplification that occurs in each reaction. Various concentrations or combinations of compounds may also be tested in separate reaction mixtures to determine the effect on amplification efficiency. The amplification and/or polymerization efficiency may be determined by various methods known in the art, including, but not limited to, determination of calibration dilution curves and slope calculation, determination using qBase software as described in Hellemans et al., *Genome Biology* 8:R19 (2007), determination using the delta delta Cq ($\Delta\Delta Cq$) calculation as described by Livak and Schmittgen, *Methods* 25:402 (2001), or by the method as described by Pfaffl, *Nucl. Acids Res.* 29:e45 (2001), all of which are herein incorporated by reference in their entirety.

Exemplary methods for polymerizing and/or amplifying nucleic acids include, for example, polymerase-mediated extension reactions. For instance, the polymerase-mediated extension reaction can be the polymerase chain reaction (PCR). In other embodiments, the nucleic acid amplification reaction is a multiplex reaction. For instance, exemplary methods for polymerizing and/or amplifying and detecting nucleic acids suitable for use as described herein are commercially available as TaqMan® (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety). TaqMan® assays are typically carried out by performing nucleic acid amplification on a target polynucleotide using a nucleic acid polymerase having 5'-to-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

Another exemplary system suitable for use as described herein utilizes double-stranded probes in displacement hybridization methods (see, e.g., Morrison et al. *Anal. Biochem.*, 18:231-244 (1989); and/or Li, et al. *Nucleic Acids Res.*, 30(2,e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for polymerizing and/or amplifying and detecting target nucleic acids suitable for use as described herein involve "molecular beacons," which are single-stranded hairpin shaped oligonucleotide probes. In the presence of the target sequence, the probe unfolds, binds and emits a signal (e.g., fluoresces). A molecular beacon typically includes at least four components: 1) the "loop," an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher moiety that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA®), a single step isothermal process for polymerizing and/or amplifying RNA to double stranded DNA without temperature cycling. A NASBA reaction typically requires avian myeloblastosis virus (AMV), reverse transcriptase (RT), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpions™ system is another exemplary assay format that may be used in the methods described herein. Scorpions™ primers are bi-functional molecules in which a primer is covalently linked to the probe, along with a detectable label (e.g., a fluorophore) and a non-detectable quencher moiety that quenches the fluorescence of the detectable label. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., a hexaethylene glycol (HEG) monomer (Whitcombe, et al. *Nat. Biotech.* 17: 804-807 (1999)) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpions™ system may be used to examine and identify point mutations using multiple probes that may be differently tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for such labeled probes are known in the art and would be suitable for use in the methods described herein.

The novel compounds provided herein may also be used in compositions and/or reaction mixtures that inhibit or substantially inhibit polymerase activity of a nucleic acid polymerase under a certain set of conditions (e.g., at a certain temperature or pH). Inhibition of polymerase activity can be used to decrease the formation of undesired secondary amplification products such as in "hot start" techniques. In some hot start techniques, a component critical to DNA polymerase activity (e.g., divalent ions and/or the DNA polymerase itself) may not be added to the reaction mixture until the temperature of the mixture is high enough to prevent non-specific primer annealing. Exemplary hot start techniques may include, for instance, oligonucleotide-based systems, antibody-based systems, chemical-based systems, and/or a combination of any of these (e.g., dual, triple, quadruple, etc. hot start systems). For instance, the magnesium or the DNA polymerase can be sequestered in a wax bead, which melts as the reaction temperature increases, releasing the sequestered component only at the elevated temperature. According to other techniques, the DNA polymerase is reversibly inactivated or modified, for example by a reversible chemical modification of the DNA polymerase, the binding of an antibody or antibodies to the DNA polymerase, or an oligonucleotide molecules that bind to the DNA polymerase. In some embodiments, the chemical modification is reversed, or the antibody molecule(s) or oligonucleotide molecule(s) are denatured at an elevated reaction temperature, releasing a functional DNA polymerase. Dual hot start reaction systems typically comprise at least two different hot start mechanisms that inhibit or substantially inhibit the polymerase activity of a nucleic acid polymerase under a certain set of conditions (e.g., at a certain temperature or pH). Such temperature-dependent hot start mechanisms may include, but are not limited to, antibodies or combinations of antibodies that block DNA polymerase activity at lower temperatures, oligonucleotides that block DNA polymerase activity at lower temperatures, reversible chemical modifications of the DNA polymerase that dissociate at elevated temperatures, amino acid modifications of the DNA polymerase that provide reduced activity at lower temperatures, fusion proteins that include hyperstable DNA binding domains and topoisomerase, temperature dependent ligands that inhibit the DNA polymerase, single stranded binding proteins that sequester primers at lower temperatures, reversibily-modified primers and/or modified dNTPs that change conformation at a particular temperature. Methods such as these are described in detail in various references including, for example, Chou et al., Nucl. Acids Res. 20:1717-1723 (1992); Dang et al., *J. Mol. Biol.* 264:268 (1996); D'Aquila et al., Nucl. Acids Res. 19:3749 (1991); U.S. Pat. Nos. 5,338,671; 5,587,287; 5,677,152; 5,773,258; 8,470,531; and/or US Pat. Pub. 2010-0317062 A1; all of which are hereby incorporated into this disclosure in their entirety. Other hot start techniques are also known in the art and may be suitable for use with the novel compounds described herein, as would be understood by those of ordinary skill in the art.

The nucleic acid polymerases that may be employed in the disclosed nucleic acid amplification reactions may be any that function to carry out the desired reaction including, for example, a prokaryotic, fungal, viral, bacteriophage, plant, and/or eukaryotic nucleic acid polymerase. As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'-to-3' direction. Since DNA polymerase can only add a nucleotide onto a pre-existing 3'-OH group, to begin a DNA synthesis reaction, the DNA polymerase needs a primer to which it can add the first nucleotide. Suitable primers may comprise oligonucleotides of RNA or DNA, or chimeras thereof (e.g., RNA/DNA chimerical primers). The DNA polymerases may be a naturally occurring DNA polymerases or a variant of natural enzyme having the above-mentioned activity. For example, it may include a DNA polymerase having a strand displacement activity, a DNA polymerase lacking 5'-to-3' exonuclease activity, a DNA polymerase having a reverse transcriptase activity, or a DNA polymerase having an endonuclease activity.

Suitable nucleic acid polymerases may also comprise holoenzymes, functional portions of the holoenzymes, chimeric polymerase, or any modified polymerase that can effectuate the synthesis of a nucleic acid molecule. Within this disclosure, a DNA polymerase may also include a polymerase, terminal transferase, reverse transcriptase, telomerase, and/or polynucleotide phosphorylase. Non-limiting examples of polymerases may include, for example, T7 DNA polymerase, eukaryotic mitochondrial DNA Polymerase γ, prokaryotic DNA polymerase I, II, III, IV, and/or V; eukaryotic polymerase α, β, γ, δ, ε, ζ, ι, and/or κ; *E. coli* DNA polymerase I; *E. coli* DNA polymerase III alpha and/or epsilon subunits; *E. coli* polymerase IV, *E. coli* polymerase V; *T. aquaticus* DNA polymerase I; *B. stearothermophilus* DNA polymerase I; *Euryarchaeota* polymerases; terminal deoxynucleotidyl transferase (TdT); *S. cerevisiae* polymerase 4; translesion synthesis polymerases; reverse transcriptase; and/or telomerase. Non-limiting examples of suitable thermostable DNA polymerases that may be used include Taq, Tfl, Tfi, Pfu, and Vent™ DNA polymerases, any genetically engineered DNA polymerases, any having reduced or insignificant 3'-to-5' exonuclease activity (e.g., SuperScript™ DNA polymerase), and/or genetically engineered DNA polymerases (e.g., those having the active site mutation F667Y or the equivalent of F667Y (e.g., in Tth), AmpliTaq®FS, ThermoSequenase™), AmpliTaq® Gold, Therminator I, Therminator II, Therminator III, Therminator Gamma (all available from New England Biolabs, Beverly, Mass.), and/or any derivatives and fragments thereof. Other nucleic acid polymerases may also be suitable as would be understood by one of skill in the art.

In another aspect, the present disclosure provides reaction mixtures for polymerizing and/or amplifying a nucleic acid sequence of interest (e.g., a target sequence). In some embodiments, the reaction mixture may further comprise a detectable label. The methods may also include one or more steps for detecting the detectable label to quantitate the amplified nucleic acid. As used herein, the term "detectable label" refers to any of a variety of signaling molecules indicative of amplification. For example, SYBR® Green and other DNA-binding dyes are detectable labels. Such detectable labels may comprise or may be, for example, nucleic acid intercalating agents or non-intercalating agents. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent may produce a detectable signal directly or indirectly. The signal may be detectable directly using, for example, fluorescence and/or absorbance, or indirectly using, for example, any moiety or ligand that is detectably affected by proximity to double-stranded nucleic acid is suitable such as a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (see, e.g., U.S. Pat. Nos. 5,994,056; 6,171,785; and/or 6,814,934). Similarly, actinomycin D fluoresces in the red portion of the UV/VIS spectrum when bound to single-stranded nucleic acids, and fluoresces in the green portion of the UV/VIS spectrum when bound to double-stranded nucleic acids. And in another example, the photoreactive psoralen 4-aminomethyl-4-5',8-trimethylpsoralen (AMT) has been reported to exhibit decreased absorption at long wavelengths and fluorescence upon intercalation into double-stranded DNA (Johnson et al. *Photochem. & Photobiol.*, 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binders as described herein such as Hoechst 33258, distamycin, netropsin) may also be suitable for use. For example, Hoechst 33258 (Searle, et al. *Nucl. Acids Res.* 18(13):3753-3762 (1990)) exhibits altered fluorescence with an increasing amount of target. Minor groove binders are described in more detail elsewhere herein.

Other DNA binding dyes are available to one of skill in the art and may be used alone or in combination with other agents and/or components of an assay system. Exemplary DNA binding dyes may include, for example, acridines (e.g., acridine orange, acriflavine), actinomycin D (Jain, et al. *J. Mol. Biol.* 68:21 (1972)), anthramycin, BOBO™-1, BOBO™-3, BO-PRO™-1, cbromomycin, DAPI (Kapuseinski, et al. *Nucl. Acids Res.* 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Cambrex Bio Science Rockland Inc., Rockland, Me.), Hoechst 33258 (Searle and Embrey, *Nucl. Acids Res.* 18:3753-3762 (1990)), Hoechst 33342, homidium, JO-PRO™-1, LIZ dyes, LO-PRO™-1, mepacrine, mithramycin, NED dyes, netropsin, 4',6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX® blue, SYTOX® green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Aldrich Chemical Co., Milwaukee, Wis.), TOTO™-3, YO-PRO®-1, and YOYO®-3 (Molecular Probes, Inc., Eugene, Oreg.), among others. SYBR® Green I (see, e.g., U.S. Pat. Nos. 5,436,134; 5,658,751; and/or 6,569,927), for example, has been used to monitor a PCR reactions. Other DNA binding dyes may also be suitable as would be understood by one of skill in the art.

For use as described herein, one or more detectable labels and/or quenching agents may be attached to one or more primers and/or probes (e.g., detectable label). The detectable label may emit a signal when free or when bound to one of the target nucleic acids. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorphore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM); 5-Hydroxy Tryptamine (5-HAT); 6-JOE; 6-carboxyfluorescein (6-FAM); FITC; 6-carboxy-1,4-dichloro-2',7'-dichlorofluorescein (TET); 6-carboxy-1,4-dichloro-2',4',5',7'-tetrachlorofluorescein (HEX); 6-carboxy-4',5'-dichloro-2',7'-dimethoxyfluorescein (JOE); Alexa Fluor® fluorophores (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (Fi-CRhR), fluorescent proteins (e.g., green fluorescent protein (e.g., GFP, EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker® and LysoSensor™ (e.g., LysoTracker® Blue DND-22, LysoTracker® Blue-White DPX, LysoTracker® Yellow HCK-123, LysoTracker® Green DND-26, LysoTracker® Red DND-99, LysoSensor™ Blue DND-167, LysoSensor™ Green DND-189, LysoSensor™ Green DND-153, LysoSensor™ Yellow/Blue DND-160, LysoSensor™ Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethylrhodamine), Tetramethylrhodamine (TRITC), WT), Texas Red, Texas Red-X, VIC and other labels described in, e.g., U.S. Patent Application Publication No. 2009/0197254 (incorporated herein by reference in its entirety), among others as would be known to those of skill in the art. Other detectable labels may also be used (see, e.g., U.S. Patent Application Publication No. 2009/0197254 (incorporated herein by reference in its entirety)), as would be known to those of skill in the art. Any of these systems and detectable labels, as well as many others, may be used to detect amplified target nucleic acids.

Some detectable labels may be sequence-based (also referred to herein as "locus-specific detectable label"), for example 5'-nuclease probes. Such probes may comprise one or more detectable labels. Various detectable labels are known in the art, for example (TaqMan® probes described herein (See also U.S. Pat. No. 5,538,848 (incorporated herein by reference in its entirety)) various stem-loop molecular beacons (See, e.g., U.S. Pat. Nos. 6,103,476 and 5,925,517 and Tyagi and Kramer, *Nature Biotechnology* 14:303-308 (1996)), stemless or linear beacons (See, e.g., PCT Publication No. WO 99/21881; U.S. Pat. No. 6,485,901), PNA Molecular Beacons™ (See, e.g., U.S. Pat. Nos. 6,355,421 and 6,593,091), linear PNA beacons (See, e.g., Kubista et al., SPIE 4264:53-58 (2001)), non-FRET probes (See, e.g., U.S. Pat. No. 6,150,097), Sunrise®/Amplifluor® probes (U.S. Pat. No. 6,548,250), stem-loop and duplex Scorpions™ probes (Solinas et al., *Nucleic Acids Research* 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes (Svanvik, et al. *Anal Biochem* 281:26-35 (2001)), self-assembled nanoparticle probes, ferrocene-modified probes described, for example, in U.S. Pat. No. 6,485,901; Mhlanga et al., *Methods* 25:463-471 (2001); Whitcombe et al., *Nature Biotechnology.* 17:804-807 (1999); Isacsson et al., *Molecular Cell Probes.* 14:321-328 (2000); Svanvik et al., *Anal Biochem.* 281:26-35 (2000); Wolffs et al., *Biotechniques* 766:769-771 (2001); Tsourkas et al., *Nucleic Acids Research.* 30:4208-4215 (2002); Riccelli et al., *Nucleic Acids Research* 30:4088-4093 (2002); Zhang et al., *Acta Biochimica et Biophysica Sinica (Shanghai).* 34:329-332 (2002); Maxwell et al., *J. Am. Chem. Soc.* 124:9606-9612 (2002); Broude et al., *Trends Biotechnol.* 20:249-56 (2002); Huang et al., *Chem Res. Toxicol.* 15:118-126 (2002); and Yu et al., *J. Am. Chem. Soc.* 14:11155-11161 (2001); QuantiProbes® (www.qiagen.com), HyBeacons® (French, et al. *Mol. Cell. Probes* 15:363-374 (2001)), displacement probes (Li, et al. *Nucl. Acids Res.* 30:e5 (2002)), HybProbes (Cardullo, et al. *Proc. Natl. Acad. Sci. USA* 85:8790-8794 (1988)), MGB Alert (www.nanogen.com), Q-PNA (Fiandaca, et al. *Genome Res.* 11:609-611 (2001)), Plexor® (www.Promega.com), LUX™ primers (Nazarenko, et al. *Nucleic Acids Res.* 30:e37 (2002)), DzyNA primers (Todd, et al. *Clin. Chem.* 46:625-630 (2000)). Detectable labels may also comprise non-detectable quencher moieties that quench the fluorescence of the detectable label, including, for example, black hole quenchers (Biosearch), Iowa Black® quenchers (IDT), QSY quencher (Molecular Probes), and Dabsyl and Dabcyl sulfonate/carboxylate Quenchers (Epoch). Detectable labels may also comprise two probes, wherein for example a fluorophore is on one probe, and a quencher is on the other, wherein hybridization of the two probes together on a target quenches the signal, or wherein hybridization on a target alters the signal signature via a change in fluorescence. Exemplary systems may also include FRET, salicylate/DTPA ligand systems (see, e.g., Oser et al. *Angew. Chem. Int. Engl.* 29(10):1167 (1990)), displacement hybridization, homologous probes, and/or assays described in European Patent No. EP 070685 and/or U.S. Pat. No. 6,238,927. Detectable labels can also comprise sulfonate derivatives of fluorescein dyes with $SO_3$ instead of the carboxylate group, phosphoramidite forms of fluorescein, phosphoramidite forms of Cy5 (available for example from Amersham). All references cited above are hereby incorporated herein by reference in their entirety.

Other embodiments provide methods for inhibiting inactivation of a polymerase during a thermal cycling process by including therein a novel compound of Formula I. Also provided are methods for providing an enzyme having polymerase activity and at least one novel compound of Formula I and combining the same to form a mixture under conditions such that the polymerase activity of the enzyme is stabilized. The polymerase may be any available to the skilled artisan, including but not limited to those described herein. In certain embodiments, the polymerase is thermostable.

The novel compounds and methods described herein may be useful for detecting and/or quantifying a variety of target nucleic acids from a test sample. A target nucleic acid is any nucleic acid for which an assay system is designed to identify or detect as present (or not), and/or quantify in a test sample. Such nucleic acids may include, for example, those of infectious agents (e.g., virus, bacteria, parasite, and the like), a disease process such as cancer, diabetes, or the like, or to measure an immune response. Exemplary "test samples" include various types of samples, such as biological samples. Exemplary biological samples include, for instance, a bodily fluid (e.g., blood, saliva, spinal fluid), a tissue sample, a food (e.g., meat) or beverage (e.g., milk) product, or the like. Expressed nucleic acids may include, for example, genes for which expression (or lack thereof) is associated with medical conditions such as infectious disease (e.g., bacterial, viral, fungal, protozoal infections) or cancer. The methods described herein may also be used to detect contaminants (e.g., bacteria, virus, fungus, and/or protozoan) in pharmaceutical, food, or beverage products. The methods described herein may be also be used to detect rare alleles in the presence of wild type alleles (e.g., one mutant allele in the presence of $10^6$-$10^9$ wild type alleles). The methods are useful to, for example, detect minimal residual disease (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine).

Kits for performing the methods described herein are also provided. As used herein, the term "kit" refers to a packaged set of related components, typically one or more compounds or compositions. The kit may comprise a pair of oligonucleotides for polymerizing and/or amplifying at least one target nucleic acid from a sample, one or more novel compounds (e.g., and/or conventional detergents, or a mixture comprising any of the same), a biocatalyst (e.g., DNA polymerase) and/or corresponding one or more probes labeled with a detectable label. The kit may also include samples containing pre-defined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. In one embodiment, the kit may include one or more of, for example, a buffer (e.g., Tris), one or more salts (e.g., KCl), glycerol, dNTPs (dA, dT, dG, dC, dU), recombinant BSA (bovine serum albumin), a dye (e.g., ROX passive reference dye), one or more detergents (e.g., Dt4), one or more hot start PCR mechanisms, polyethylene glycol (PEG), polyvinyl pyrrolidone (PVP), and/or gelatin (e.g., fish or bovine source). Other embodiments of particular systems and kits are also contemplated which would be understood by one of skill in the art.

This disclosure further relates to the novel compound BrijL-23-Proline (of Formula 1):

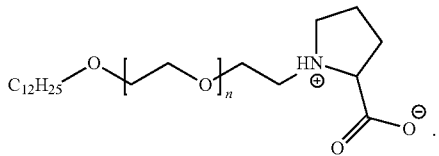

Compositions comprising a polymerase, such as a thermostable polymerase, and BrijL-23-Proline is also provided. In some embodiments a storage buffer comprising this compound is provided. For example, a storage buffer for an enzyme, such as a thermostable polymerase or reverse transcriptase can comprise this compound. In some embodiments, a kit comprising a storage or reaction composition comprising a polymerase, such as a thermostable polymerase, and BrijL-23-Proline is also provided. In some embodiments, a method for increasing the efficiency of a polymerase, such as a thermostable polymerase, said method comprising the steps of mixing a target nucleic acid with at least one polymerase, at least one primer, dNTPs, and BrijL-23-Proline; and, amplifying said target nucleic acid. In some embodiments, the increased efficiency of nucleic acid synthesis is the same as or greater than the nucleic acidy synthesis efficiency when the polymerase is in the presence of NP-40 and/or Tween® 20 instead of said compound. In certain embodiments, the effective concentration of said compound is at least about one to about ten times less than that required by conventional detergents (e.g., NP-40 or Tween® 20). In some embodiments, BrijL-23-Proline is stable in a buffer (e.g., 5× buffer) for at least about one month to about three years as measured using standard stability testing protocols (e.g., as in Example 2 below). Methods for detecting a target nucleic acid in a sample by forming a reaction mixture (e.g., comprising at least one polymerase, at least one primer, dNTPs, BrijL-23-Proline, and a detectable label), amplifying the target nucleic acid, and detecting a signal generated from the detectable label indicative of the presence and/or amount of said target nucleic acid in the sample are also provided. Methods for inhibiting inactivation of a polymerase in a thermal cycling process by contacting said polymerase with BrijL-23-Proline during the thermal cycling process are also provided. In some embodiments, the inhibition of polymerase inactivation is the same as or greater than the inhibition of polymerase inactivation when the polymerase is in the presence of NP-40 and/or Tween® 20 instead of BrijL-23-Proline. In some embodiments, methods for providing stabilized activity of a polymerase by combining an enzyme having polymerase activity and BrijL-23-Proline to form a mixture under conditions such that said polymerase activity of said enzyme (e.g., a thermostably polymerase) is stabilized. In certain embodiments, a composition comprising a stable enzyme, such as a thermostable polymerase, and BrijL-23-Proline are provided. In some embodiments a storage buffer comprising a stable enzyme, such as a thermostable polymerase, and BrijL-23-Proline are provided. In certain embodiments, the degree of stabilization is the same as or greater than the stabilization of polymerase activity when the polymerase is in the presence of NP-40 and/or Tween® 20 instead of BrijL-23-Proline. Nucleic acid amplification reaction mixtures comprising at least one polymerase (e.g., a thermostable polymerase), dNTPs, and BrijL-23-Proline are also provided. Methods for polymerizing a target nucleic acid by combining the target nucleic acid with at least one polymerase (e.g., a thermostable polymerase) and BrijL-23-Proline in a reaction mixture; and, polymerising the target nucleic acid are also provided. In some embodiments, methods for amplifying a target nucleic acid by combining the target nucleic acid with at least one polymerase and BrijL-23-Proline as part of a reaction mixture (e.g., further comprising dNTPs and/or other reagents); and, polymerizing the target nucleic acid may also be provided. In certain embodiments, polymerization or amplification of the target nucleic acid may be detected (e.g., using a detectable label that may, for instance, be part of a primer or a probe). Such polymerization and/or amplification of the target nucleic acid may also be quantitated. Exemplary thermostable polymerases that may be used as described herein may include, but are not limited to, T7 DNA polymerase, eukaryotic mitochondrial DNA Polymerase γ, prokaryotic DNA polymerase I, prokaryotic DNA polymerase II, prokaryotic DNA polymerase III, prokaryotic DNA polymerase IV, prokaryotic DNA polymerase V, eukaryotic polymerase α, eukaryotic polymerase β, eukaryotic polymerase γ, eukaryotic polymerase δ, eukaryotic polymerase ε, eukaryotic polymerase η, eukaryotic polymerase ζ, eukaryotic polymerase ι, eukaryotic polymerase κ, E. coli DNA polymerase I, E. coli DNA polymerase III alpha subunit, E. coli DNA polymerase III epsilon subunits, E. coli polymerase IV, E. coli polymerase V, T. aquaticus DNA polymerase I, B. stearothermophilus DNA polymerase I, a Euryarchaeota polymerase, terminal deoxynucleotidyl transferase (TdT), S. cerevisiae polymerase 4, a translesion synthesis polymerase, reverse transcriptase, a thermostable polymerase, telomerase, Taq DNA polymerase, Tfi DNA polymerase, Tfl DNA polymerase, Pfu DNA polymerase, and Vent™ DNA polymerase, a polymerase having reduced 3'-to-5' exonuclease activity, SuperScript™ DNA polymerase, a genetically engineered DNA polymerase, a polymerase having the active site mutation F667Y, a polymerase having the equivalent of active site F667Y, Tth polymerase, AmpliTaq®FS, ThermoSequenase™, Therminator I, Therminator II, Therminator III, and/or Therminator Gamma, and/or a derivative thereof, and/or a fragment or derivative thereof. Other methods provided herein include, for instance, methods for detecting a target nucleic acid in a sample by forming a reaction mixture comprising at least one polymerase, at least one primer, dNTPs, BrijL-23-Proline, and a detectable label; amplifying said target nucleic acid; and, detecting a signal generated from said detectable label indicative of the presence of said target nucleic acid said sample. Certain methods may utilize one or more hot start techniques such as, for instance, an oligonucleotide-based system, antibody-based system, chemical-based system, and/or a combination of any two or more of these hot start mechanisms (e.g., antibody-based and oligonucleotide-based hot start together). Methods for preparing BrijL-23-Proline are also provided, such as by activating BrijL-23 to produce BrijL-23-Mesolate; preparing BrijL-23-Iodide from BrijL-23-Mesolate; preparing BrijL-23-Proline-t-Butyl ester from BrijL-23-Iodide; hydrolyzing BrijL-23-Proline-t-Butyl ester to produce BrijL-23-Proline; and, optionally, neutralizing BrijL-23-Proline (using, e.g., Amberlite®). Other embodiments described herein are also contemplated herein, as would be clear to those of ordinary skill in the art.

In some embodiments compositions comprising BrijL-23-Proline are provided. In certain embodiments, such compositions comprise BrijL-23-Proline at a concentration of 0.000001%, 0.00001%, 0.0001%, 0.001%, 0.01%, 0.1%, 1%, 10%, 15%, 20%, or 30%. In some preferable embodiments, BrijL-23-Proline is present in such compositions at a concentration of 0.001% to 10%. In some more preferable embodiments, BrijL-23-Proline is present in such compositions at a concentration of 0.01 to 1%.

To more clearly and concisely describe and point out the subject matter of the present disclosure, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Where necessary, ranges have been supplied, and those ranges are inclusive of all sub-ranges there between.

In this disclosure, the use of the singular can include the plural unless specifically stated otherwise or unless, as will be understood by one of skill in the art in light of the present disclosure, the singular is the only functional embodiment. Thus, for example, "a" may mean more than one, and "one embodiment" may mean that the description applies to multiple embodiments. The phrase "and/or" denotes a shorthand way of indicating that the specific combination is contemplated in combination and, separately, in the alternative.

It will be appreciated that there is an implied "about" prior to the temperatures, concentrations, times, etc. discussed in the present teachings, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

As used herein the terms "nucleotide" or "nucleotide base" refer to a nucleoside phosphate. It includes, but is not limited to, a natural nucleotide, a synthetic nucleotide, a modified nucleotide, or a surrogate replacement moiety or universal nucleotide (e.g., inosine). The nucleoside phosphate may be a nucleoside monophosphate, a nucleoside diphosphate or a nucleoside triphosphate. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleoside triphosphate (dNTP) or a ribonucleoside triphosphate (NTP). The nucleotides may be represented using alphabetical letters (letter designation). For example, A denotes adenosine (i.e., a nucleotide containing the nucleobase, adenine), C denotes cytosine, G denotes guanosine, T denotes thymidine, U denotes uracil, and I denotes inosine. N represents any nucleotide (e.g., N may be any of A, C, G, T/U, or I). Naturally occurring and synthetic analogs may also be used, including for example hypoxanthine, 2-aminoadenine, 2-thiouracil, 2-thiothymine, 5-methylcytosine, N4-methylcytosine, 5,N4-ethencytosine, 4-aminopyrrazolo[3,4-d]pyrimidine and 6-amino-4-hydroxy [3,4-d]pyrimidine, among others. The nucleotide units of the oligonucleotides may also have a cross-linking function (e.g. an alkylating agent).

As used herein, the term "oligonucleotide" or "polynucleotide" refers to an oligomer of nucleotide or derivatives thereof. The oligomers may be DNA, RNA, or analogues thereof (e.g., phosphorothioate analogue). The oligomers may also include modified bases, and/or backbones (e.g., modified phosphate linkage or modified sugar moiety). Non-limiting examples of synthetic backbones that confer stability and/or other advantages to the oligomers may include phosphorothioate linkages, peptide nucleic acid, locked nucleic acid (Singh, et al. *Chem. Commun.* 4:455-456 (1998)), xylose nucleic acid, and/or analogues thereof. Oligonucleotides may be any length "n." For example, n may be any of 1, 2, 4, 6, 8, 12, 16, 20, 22, 24, 26, 28, 30, 32, 34, 36, 38, 40 etc. number of nucleotides. The polynucleotide structure $(N)_n$ represents an oligonucleotide consisting of n number of nucleotides N (e.g., $(I)_8$ is representative of an oligonucleotide having the sequence IIIIIIII; or $(A)_{12}$ is representative of an oligonucleotide having the sequence AAAAAAAAAAAA). Other types of oligonucleotides or polynucleotides may also be suitable for use as would be understood to one of skill in the art from this disclosure.

As used herein, the term "nucleic acid" refers to polymers of nucleotides or derivatives thereof. As used herein, the term "target nucleic acid" refers to a nucleic acid that is desired to be amplified in a nucleic acid amplification reaction. For example, the target nucleic acid comprises a nucleic acid template.

As used herein, the term "sequence" refers to a nucleotide sequence of an oligonucleotide or a nucleic acid. Throughout the specification, whenever an oligonucleotide/nucleic acid is represented by a sequence of letters, the nucleotides are in 5' to 3' order from left to right. For example, an oligonucleotide represented by a sequence $(I)_n(A)_n$ wherein n=1, 2, 3, 4 and so on, represents an oligonucleotide where the 5' terminal nucleotide(s) is inosine and the 3' terminal nucleotide(s) is adenosine.

As used herein the term "reaction mixture" refers to the combination of reagents or reagent solutions, which are used to carry out a chemical analysis or a biological assay. In some embodiments, the reaction mixture comprises all necessary components to carry out a nucleic acid (DNA) synthesis/amplification reaction. As described above, such reaction mixtures may include at least one amplification primer pair suitable for polymerizing and/or amplifying a nucleic acid sequence of interest and at least one detergent. As described above, a suitable reaction mixture may also include a "master mix" containing the components (e.g., typically not including the primer pair) needed to perform an amplification reaction. The master mix may be combined with one or more detergents to form a reaction mixture. Other embodiments of reaction mixtures are also contemplated herein as would be understood by one of skill in the art.

As used herein, the terms "reagent solution" or "solution suitable for performing a DNA synthesis reaction" refer to any or all solutions, which are typically used to perform an amplification reaction or DNA synthesis. They include, but are not limited to, solutions used in DNA amplification methods, solutions used in PCR amplification reactions, or the like. The solution suitable for DNA synthesis reaction may comprise buffer, salts, and/or nucleotides. It may further comprise primers and/or DNA templates to be amplified. One or more reagent solutions are typically included in the reactions mixtures or master mixes described herein.

As used herein, the term "primer" or "primer sequence" refers to a short linear oligonucleotide that hybridizes to a target nucleic acid sequence (e.g., a DNA template to be amplified) to prime a nucleic acid synthesis reaction. The primer may be a RNA oligonucleotide, a DNA oligonucleotide, or a chimeric sequence (e.g., comprising RNA and DNA). The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about any of, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, (and so on) nucleotides long.

As used herein, "alkyl" refers to a hydrocarbon that is optionally linear or branched, and may be fully saturated, mono- or polyunsaturated. In addition, the term "alkyl," as used herein, further includes one or more substitutions at one or more carbon atoms of the hydrocarbon chain fragment.

As used herein, "aryl" refers to an aromatic moiety having a single ring or multiple condensed rings each of which is optionally and independently substituted with H, halogen, cyano, azido, sulfonic acid, alkali or ammonium salt of sulfonic acid, carboxylic acid, biologically compatible salt of carboxylic acid, nitro, alkyl, perfluoroalkyl, alkoxy, alkylthio, amino, monoalkylamino, dialkylamino or alkylamido.

As used herein, "substituted" refers to a molecule wherein one or more hydrogen atoms are replaced with one or more non-hydrogen atoms, functional groups or moieties. For example, an unsubstituted nitrogen is —$NH_2$, while a substituted nitrogen is —$NHCH_3$. Exemplary substituents include, but are not limited to, halo, e.g., fluorine and chlorine, alkyl, alkene, alkyne, sulfate, sulfone, sulfonate, amino, ammonium, amido, nitrile, alkoxy, phenoxy, aromatic, phenyl, polycyclic aromatic, and heterocycle.

Certain embodiments are further described in the following examples. These embodiments are provided as examples only and are not intended to limit the scope of the claims in any way.

EXAMPLES

Example 1

Development of Novel Compounds

The novel compounds Dt1, Dt2, Dt3, Dt4, Dt5, Dt6, Dt7, Dt8, Dt9, D10, Dt11, and Dt12 were developed using Process 1 described below:

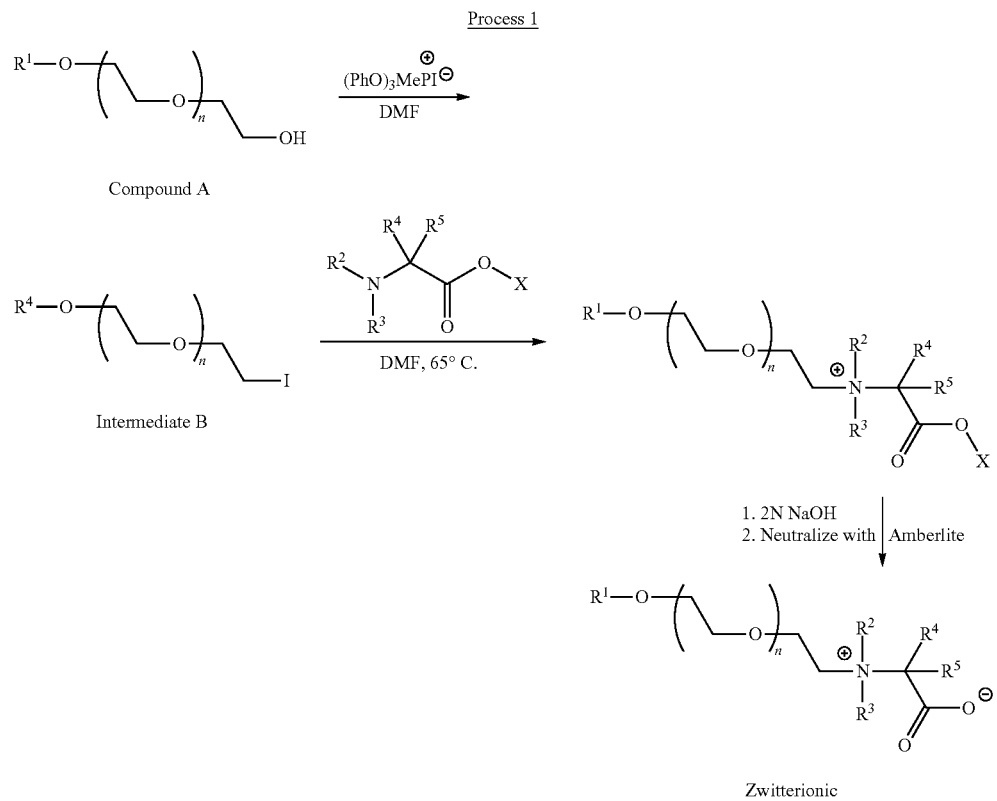

where $R^1$, $R^2$, $R^3$, $R^4$, $R^5$, and n are as described hereinabove, and X is selected from the group consisting of H, $CH_3$, $CH_2CH_3$, $CH_2(C_6H_5)$, and $C(CH_3)_3$. The novel compounds of Formula I may be, for example, ionic (e.g., cationic, anionic, zwitterionic).

As shown in Process 1, Compound A (1 eq.), methyltriphenoxyphosphonium iodide (4 eq.), and N,N-dimethyl formamide (6 mL) were added sequentially to a 50 mL aluminum foil covered round bottom flask. The reaction was then allowed to stir for 3 days under argon atmosphere at room temperature. After 3 days, the progress of the reaction was monitored using analytical LC-MS. The appearance of the intermediate product pattern will confirm its formation. This expected intermediate product (Intermediate B) was not isolated. To this intermediate product obtained from the previous step, added amino acid ester hydrochloride salt (2 eq.) and $Et_3N$ (2 eq.). The reaction mixture was heated for 3-4 days at 65° C. The progress of the reaction was monitored using analytical LC-MS. The reaction mixture was cooled down to room temperature and was then concentrated down on the rotovapor to approximately 2 mL. The concentrated crude mixture was the purified by preparative HPLC. All the desired fractions were pooled and concentrated down on the rotovapor to afford the desired product (the ionic compounds Dt1, Dt3, Dt5, Dt7, Dt9, Dt11, Dt12). This product was then subjected to hydrolysis reaction using 2N NaOH. The reaction mixture was allowed to stir at room temperature until all the starting material was consumed as observed on analytical LC-MS, followed by neutralization with Amberlite® to afford the final cationic compounds (e.g., Dt1, Dt3, Dt5, Dt7, Dt9, Dt11, and Dt12), zwitterionic compounds (e.g., Dt2, Dt4, Dt6, Dt10) or anionic compounds (Dt8) as shown below:

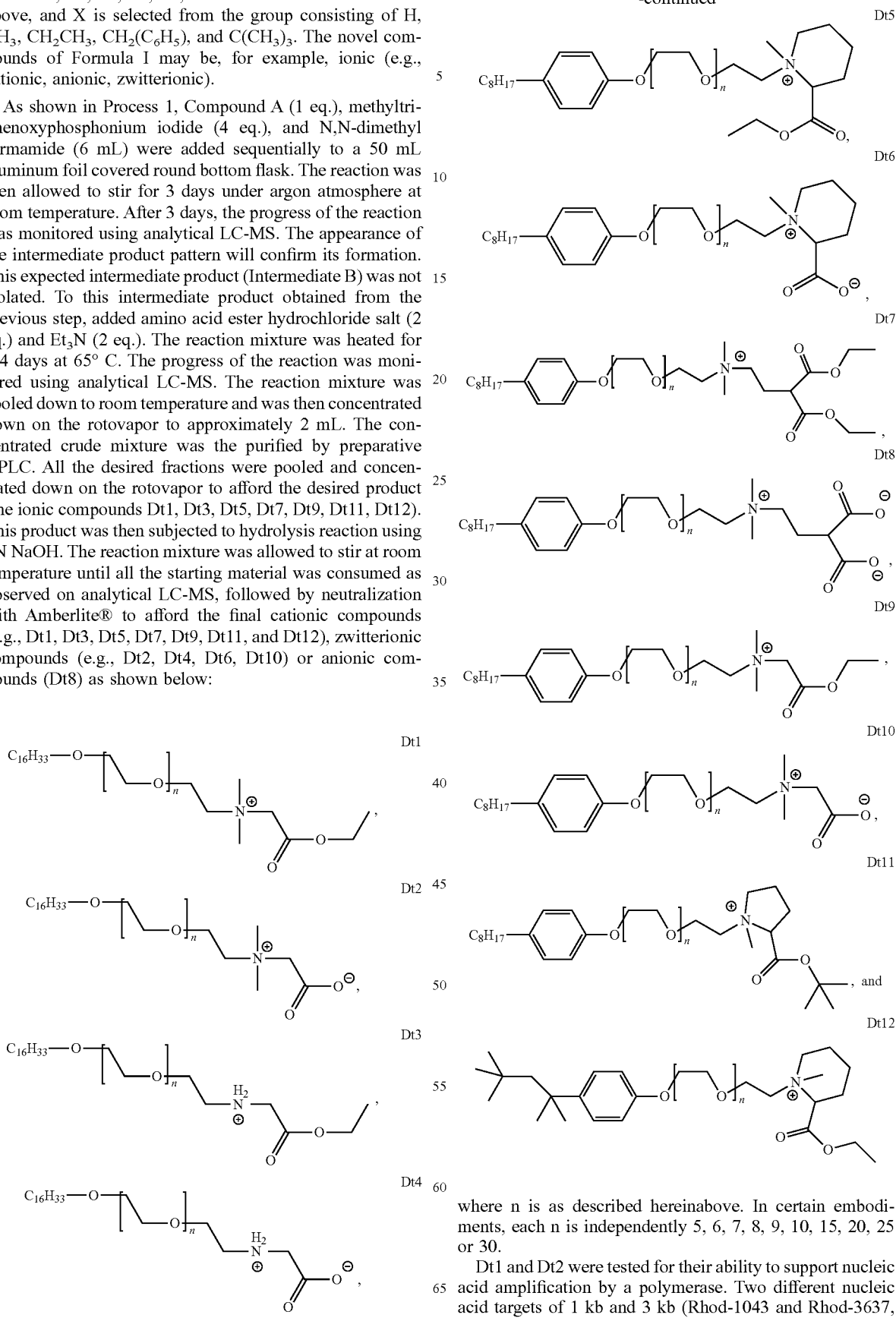

where n is as described hereinabove. In certain embodiments, each n is independently 5, 6, 7, 8, 9, 10, 15, 20, 25 or 30.

Dt1 and Dt2 were tested for their ability to support nucleic acid amplification by a polymerase. Two different nucleic acid targets of 1 kb and 3 kb (Rhod-1043 and Rhod-3637, respectively) were amplified by PCR using Taq polymerase in the presence of 0.1% NP-40 and 0.1% Tween® 20 (control reactions), Dt1 or Dt2. As shown in FIG. 1, both Dt1 and Dt2 supported the amplification reactions in a comparable manner to NP-40/Tween® 20. Dt1 supported amplification of the 1 kb amplicon (Rhod-1043) and the 3 Kb amplicon (Rhod-3637) when included in the 50 µl reaction at a concentration of between 0.008% and 0.0006%. Dt2 supported amplification of the 1 Kb amplicon (Rhod-1043) and the 3 kb amplicon (Rhod-3637) when included in the 50 µl reaction at a concentration of between 0.04% and 0.0001% (some amplification was observed at 0.0008%).

Figure 2:
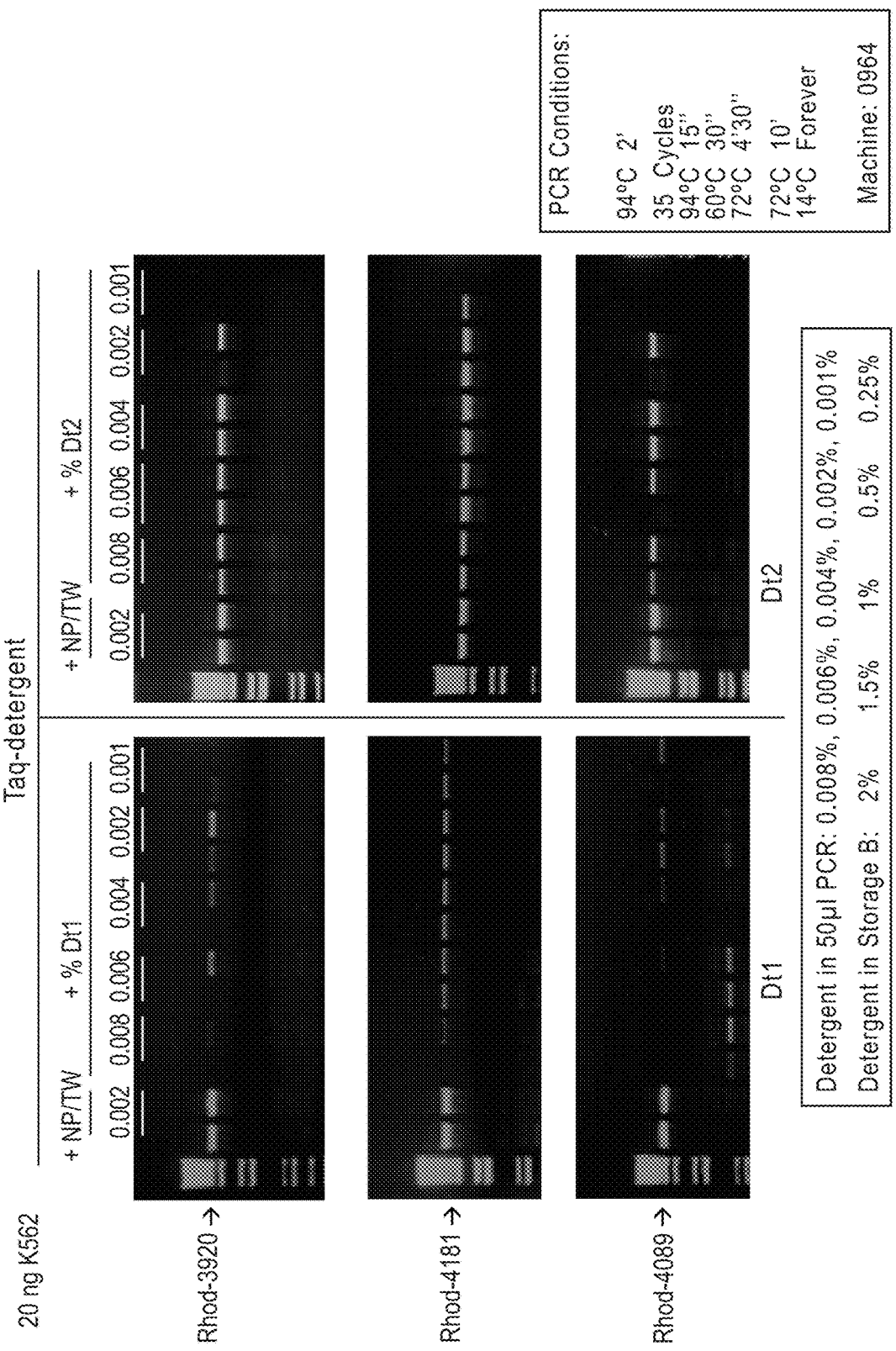
FIG. 2. Amplification of the rhodopsin gene in the presence of novel compounds Dt1 and Dt2 according to certain exemplary embodiments of the methods and compositions disclosed herein.

Dt1 was also tested using Rhodopsin gene primers to amplify approximately 4 Kb amplicons (Rhod-3920, Rhod-4181, and Rhod-4089) (FIG. 2; "Storage B": 20 mM Tris-HCl (pH 8.0), 0.1 mM EDTA, 50% glycerol, 1 mM DTT, distilled water). PCR conditions were 94° C. for two minutes; 35 cycles of 15 seconds at 94° C., 30 seconds at 60° C., four minutes 30 seconds at 72° C.; and extension for ten minutes at 72° C. Dt1 supported amplification of Rhod-3920 and Rhod-4181 when included in the 50 µl reaction at a concentration of between 0.008% and 0.001%. Dt1 supported amplification of Rhod-4089 when included in the 50 µl reaction at a concentration of between 0.008% and 0.001%.

Figure 3:
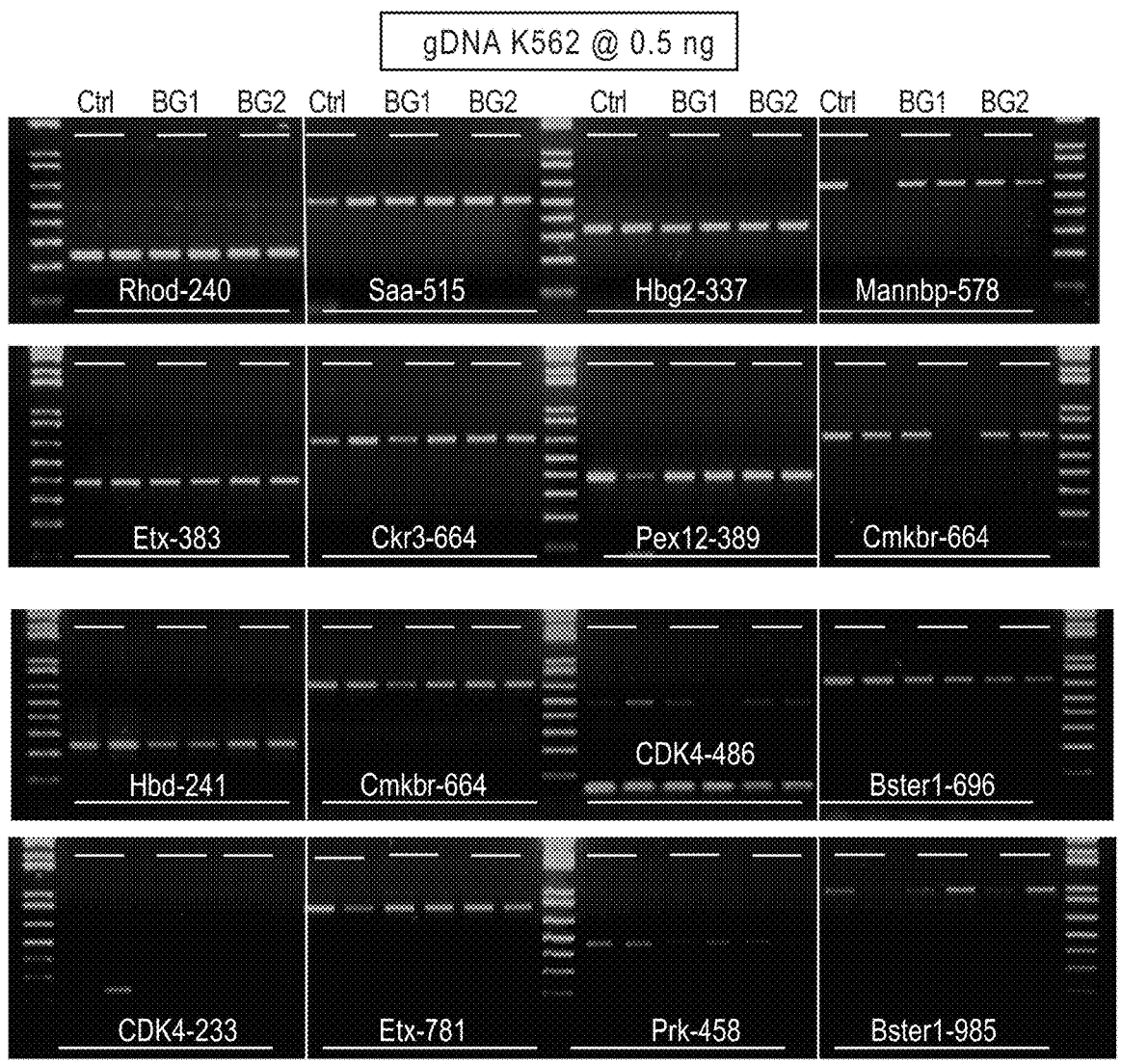
FIG. 3. Comparison of novel compound Dt2 at 0.004% and 0.0002% compared to NP-40/Tween® 20 for 0.1-1 Kb PCR products amplified according to certain exemplary embodiments of the methods and compositions disclosed herein.
Figure 4:
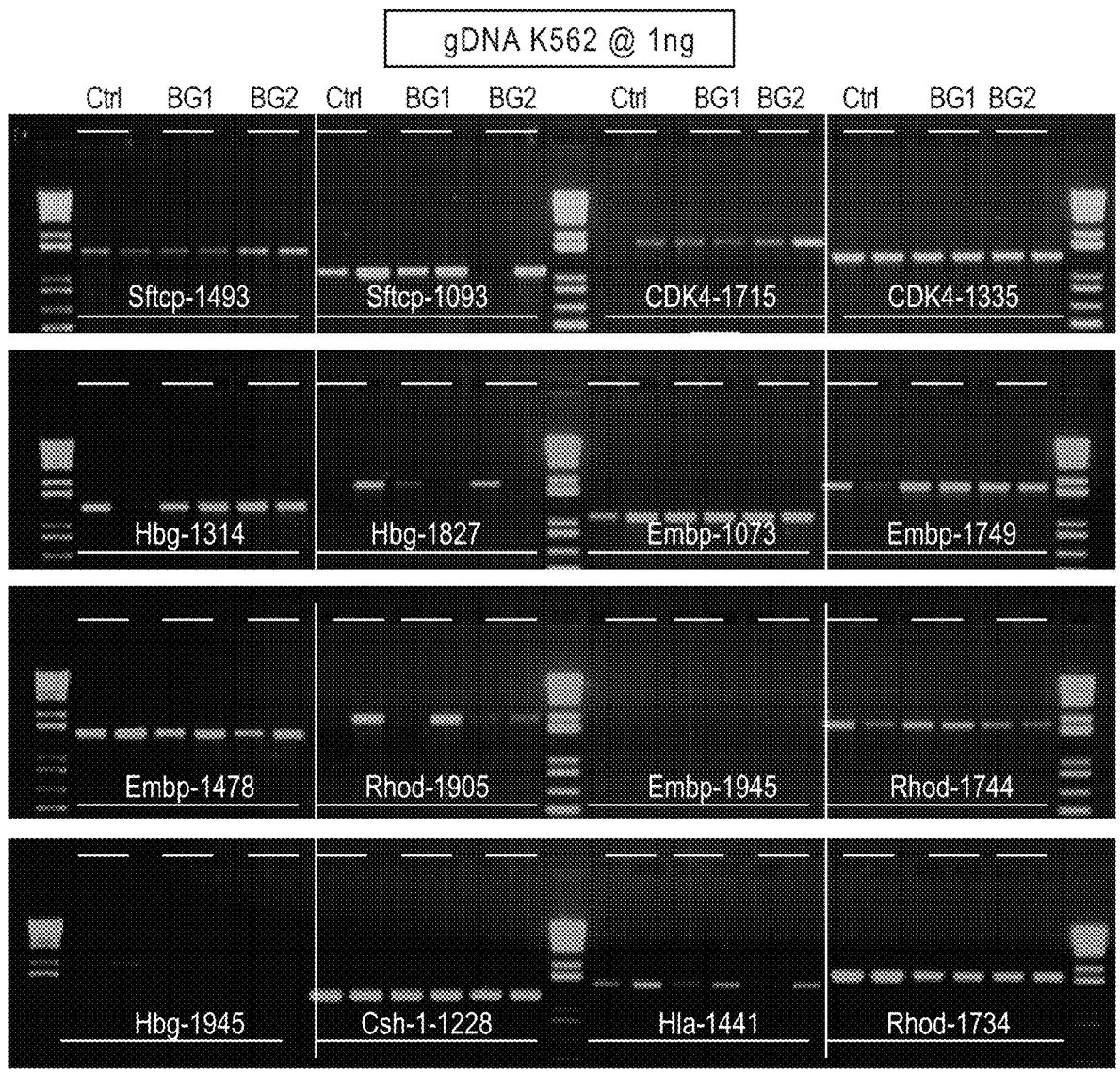
FIG. 4. Comparison of novel compounds Dt2 at 0.004% and 0.002% to NP-40/Tween® 20 for 1-2 Kb PCR products amplified according to certain exemplary embodiments of the methods and compositions disclosed herein.

FIG. 3 shows that 0.004% and 0.002% Dt1 is comparable to 0.004% NP-40/Tween® 20 in amplifying 0.1 to 1 Kb amplicons. FIG. 4 shows that 0.004% and 0.002% Dt1 is comparable to 0.004% NP-40/Tween® 20 in amplifying 1-2 kb amplicons.

Figure 5:
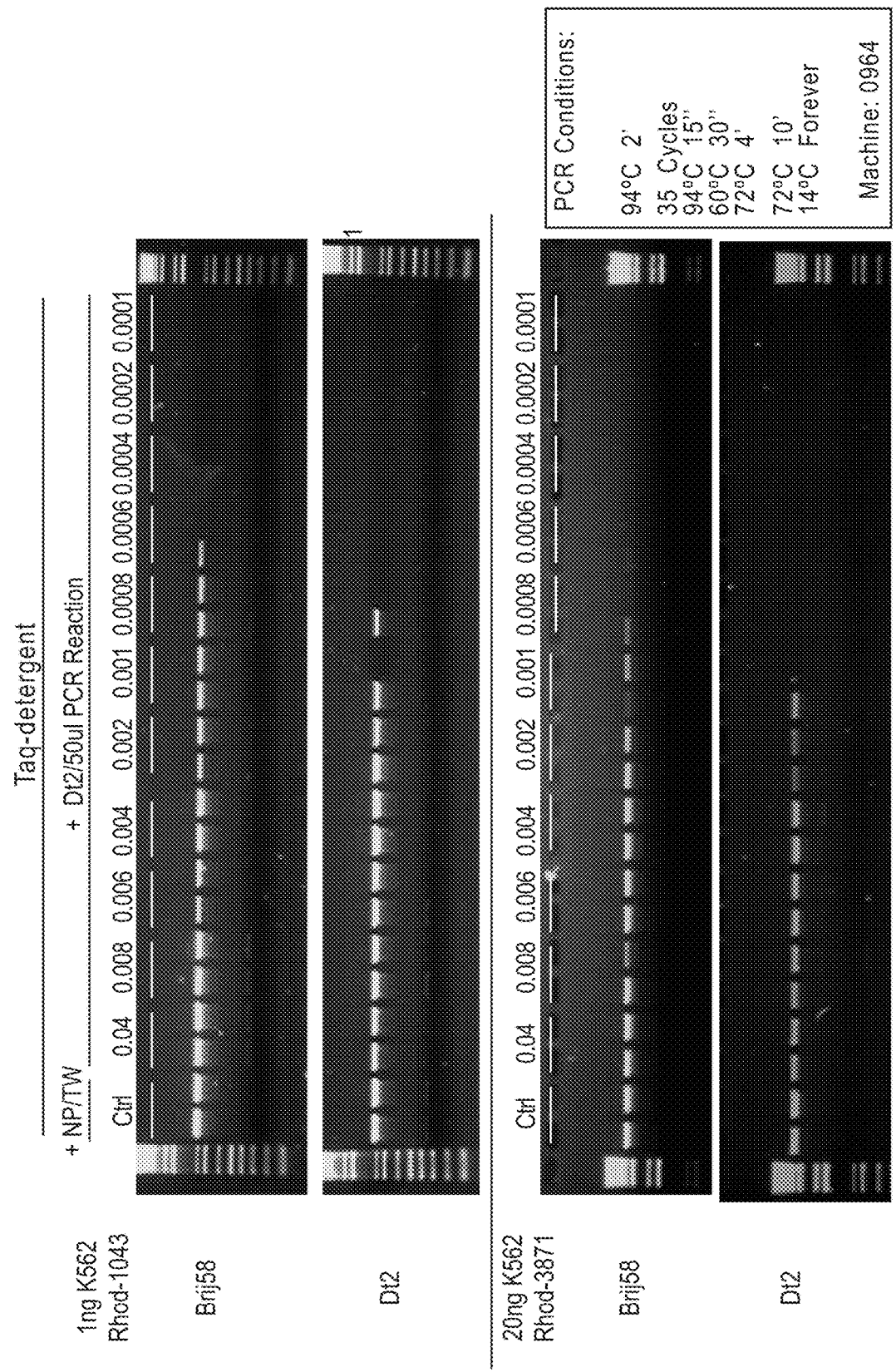
FIG. 5. PCR Activity: Comparison of novel compound Dt2 to Brij-58 alone for rhodopsin gene products amplified according to certain exemplary embodiments of the methods and compositions disclosed herein.

FIG. 5 provides a comparison between Brij-58 and Dt1. As shown therein, Dt1 (0.04% to 0.006%) supports amplification in a comparable manner to Brij-58 (0.04% to 0.0004%) or NP40/Tween® 20 (0.002%). The data indicates that this was not due to contamination of the Brij-58 starting material used for modification.

Figure 6:
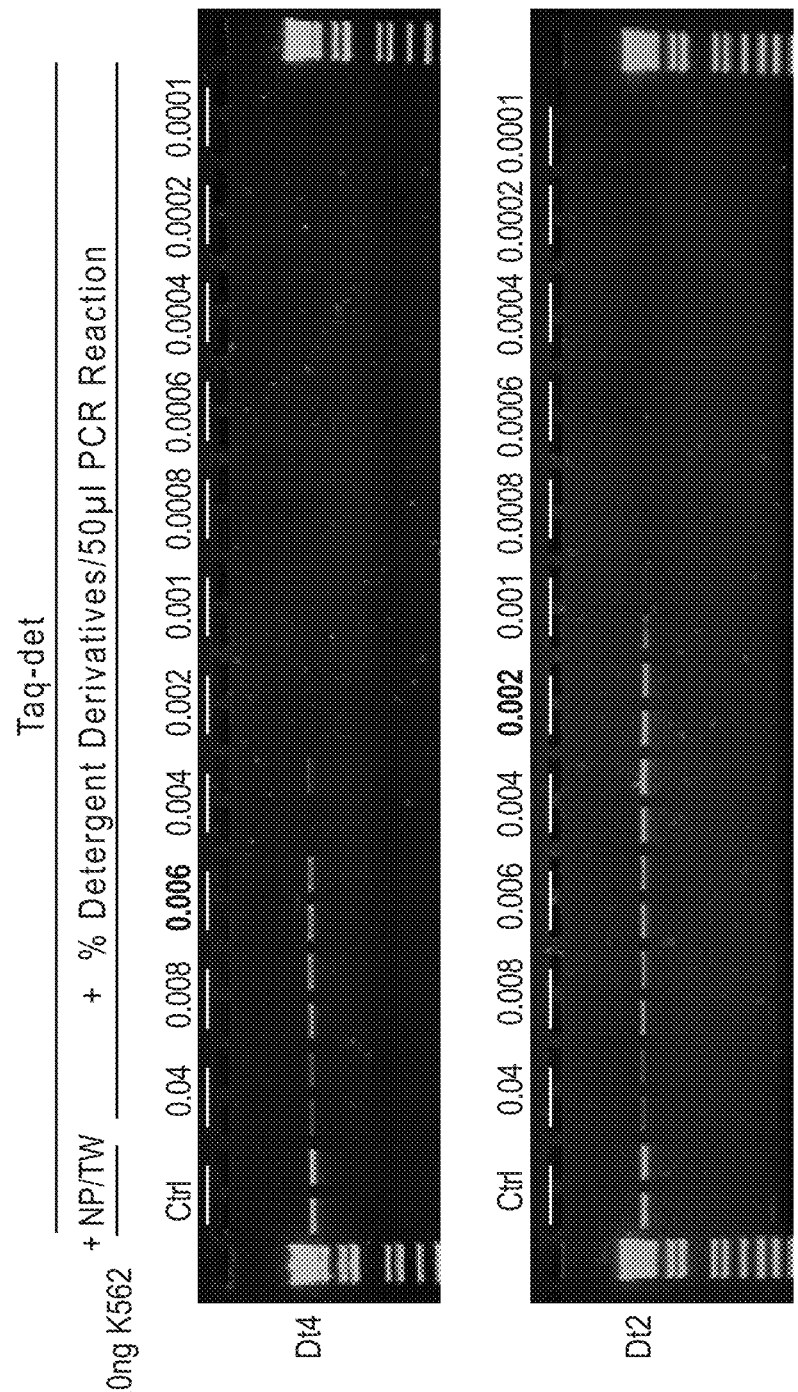
FIG. 6. Titration of novel compounds Dt2 and Dt4 using the Rhod-1043 target sequence amplified according to certain exemplary embodiments of the methods and compositions disclosed herein.
Figure 7A:
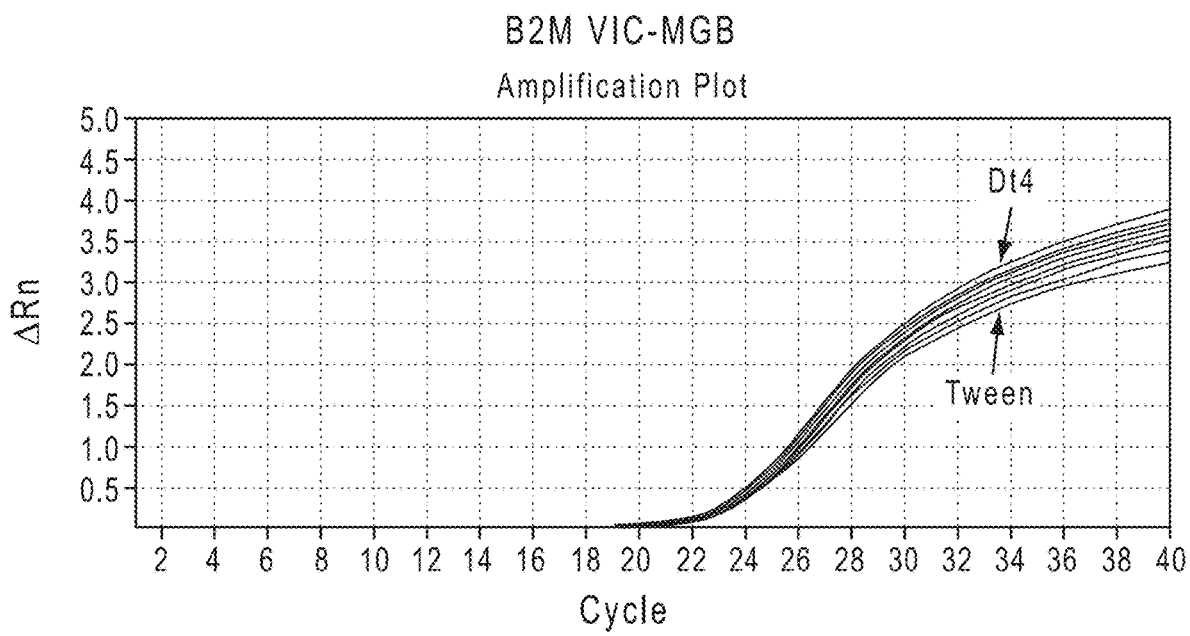
FIGS. 7A through 7D. Comparison of Dt4 to Tween® 20: amplification of beta-2 microglobulin (B2M) (FIG. 7A), glyceraldehyde 3-phosphate dehydrogenase (GAPDH) (FIG. 7B), large ribosomal protein (RPLPO) (FIG. 7C), and glucuronidase beta (GUSB) (FIG. 7D) according to certain exemplary embodiments of the methods and compositions disclosed herein.
Figure 7B:
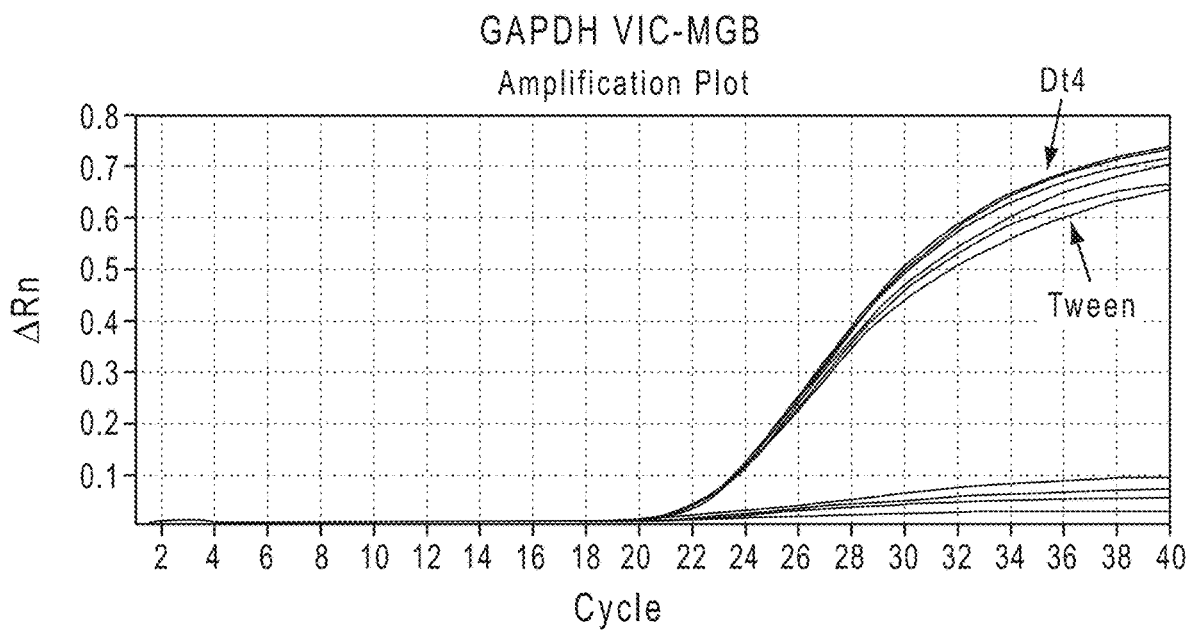
Figure 7C:
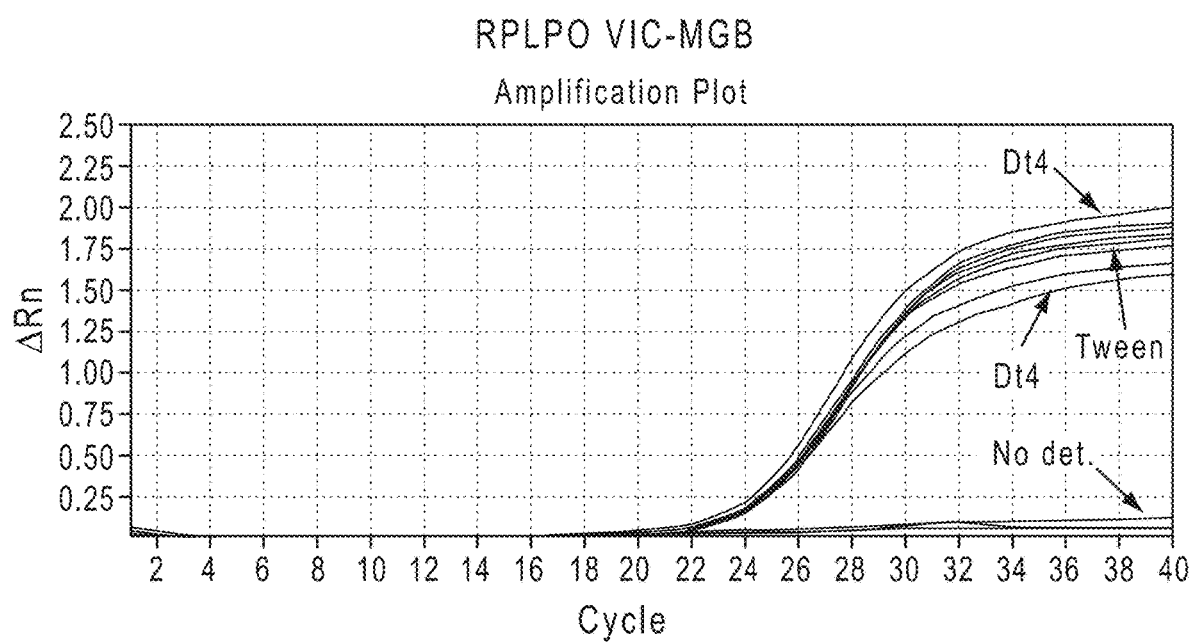
Figure 7D:
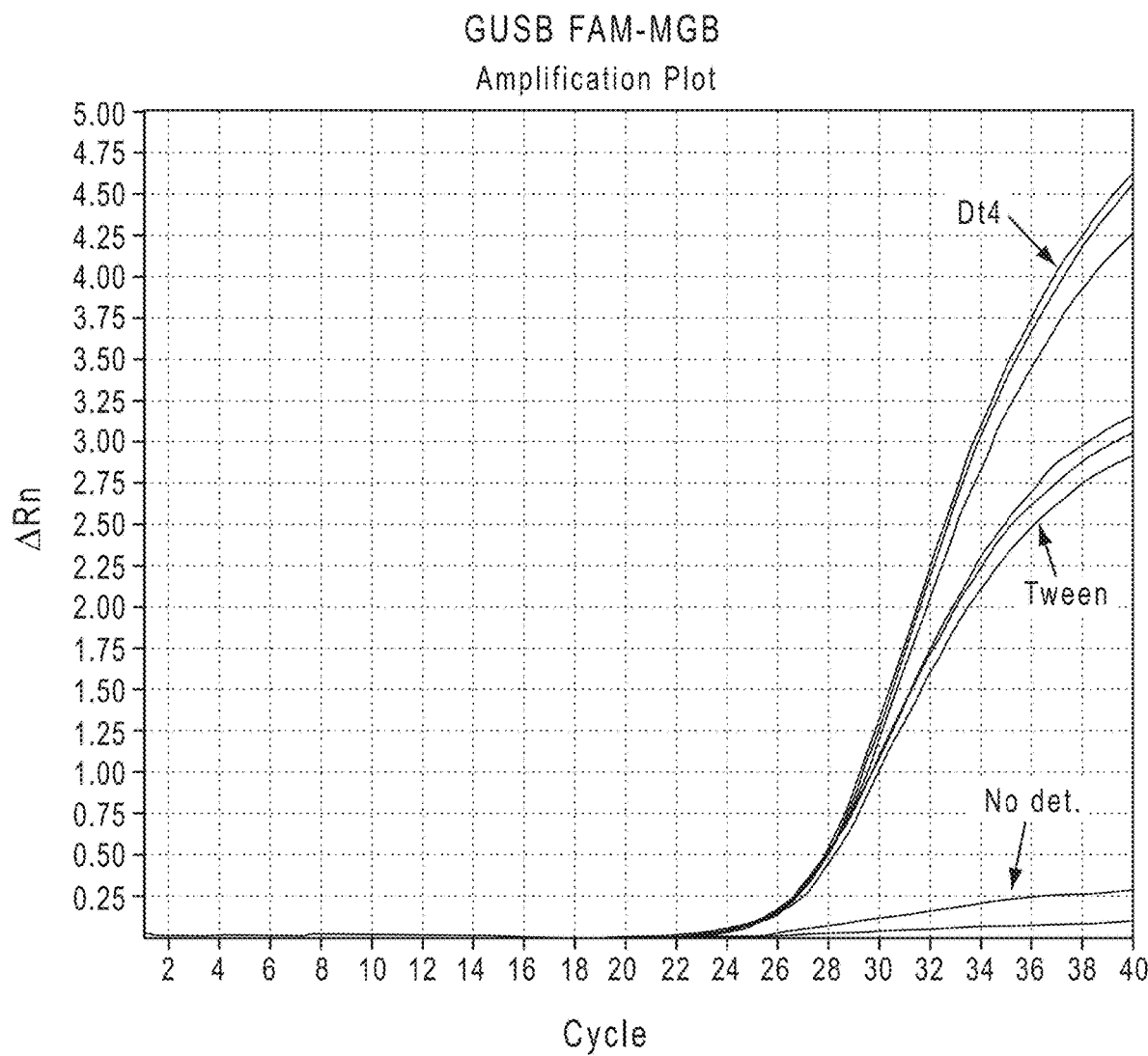
Figure 8A:
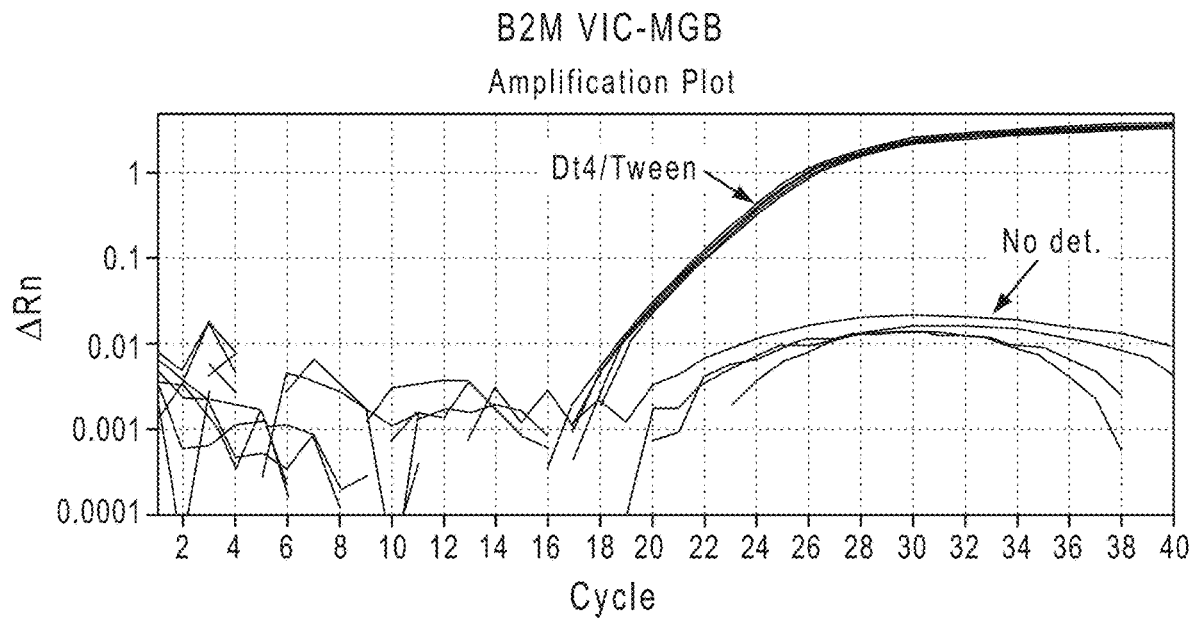
FIGS. 8A through 8D. Comparison of Dt4 to Tween® 20 (log scale): amplification of B2M (FIG. 8A), GAPDH (FIG. 8B), RPLPO (FIG. 8C), and GUSB (FIG. 8D) according to certain exemplary embodiments of the methods and compositions disclosed herein.
Figure 8B:
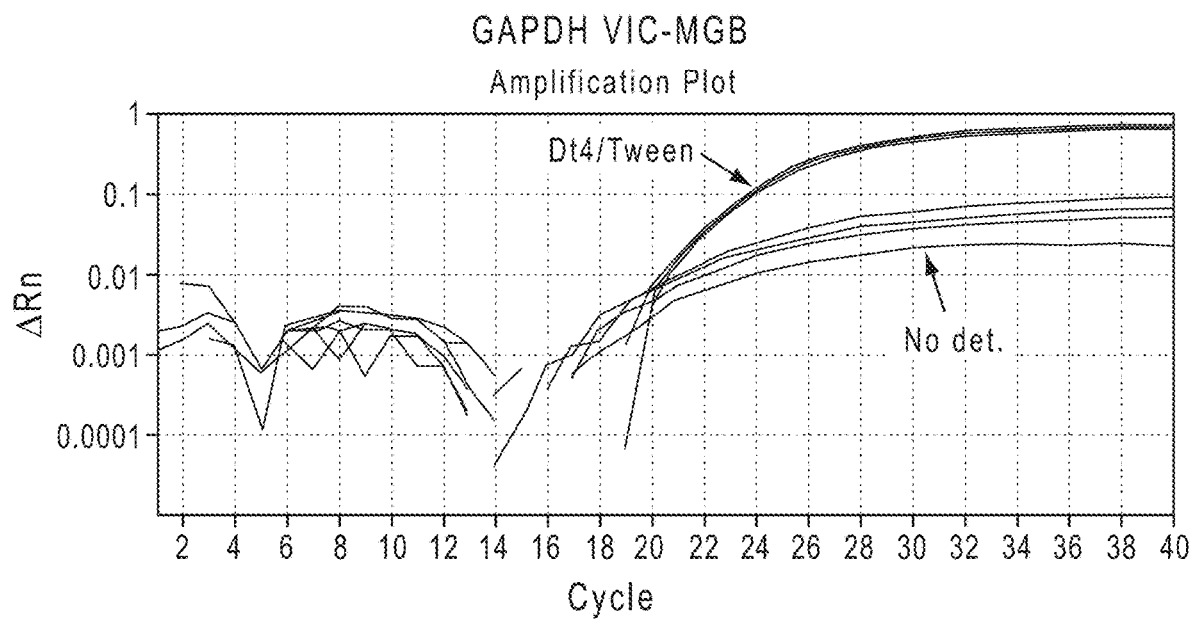
Figure 8C:
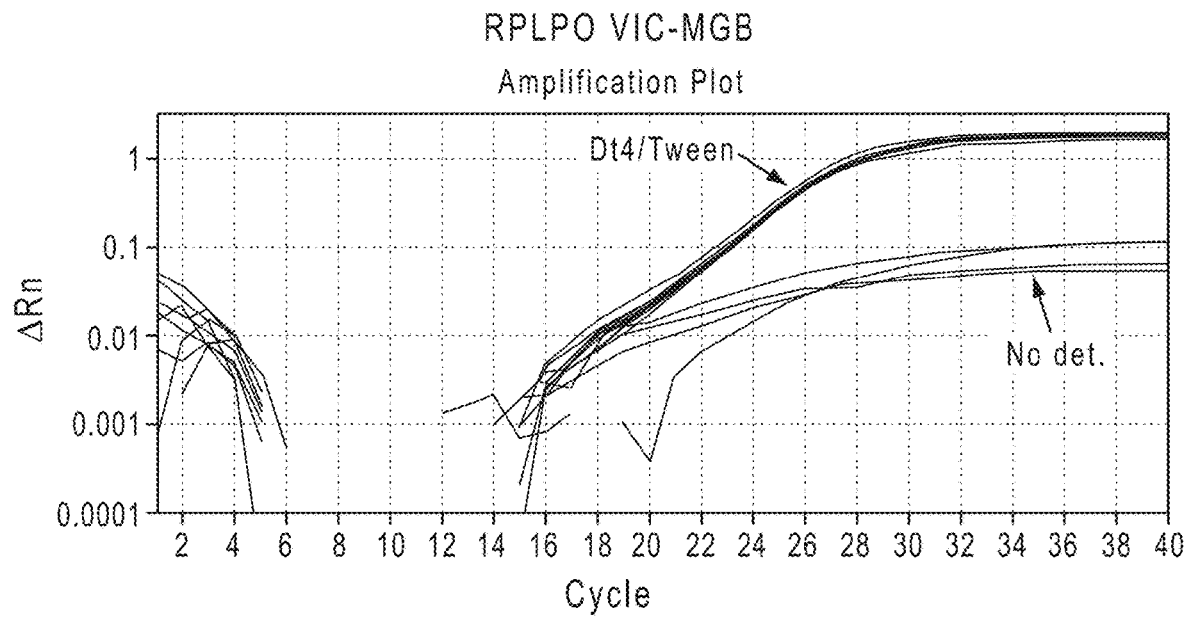
Figure 8D:
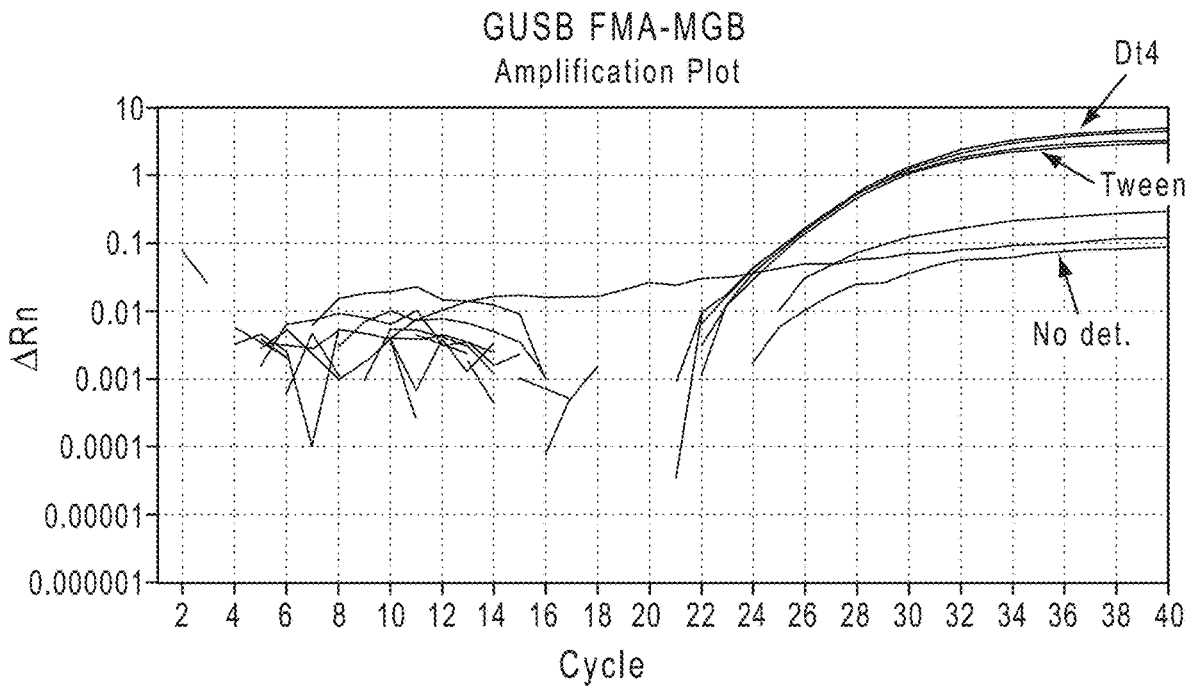

FIG. 6 compares the activity of Dt1 and Dt2. As shown therein, both modified compounds support amplification. Dt1 is shown to support amplification when included in the reaction mixture at a concentration of between 0.04% to 0.001%. Dt2 is shown to support amplification when included in the reaction mixture at a concentration of between 0.04 to 0.006%.

FIGS. 7A through 7D and FIGS. 8A through 8D provide a comparison between Dt4 and Tween® 20 in amplifying four different targets (B2M, GAPDH, RPLPO, and GUSB). As shown therein, amplification in the presence of 0.01% Dt4 or 0.01% Tween® 20 provided similar results.

Figure 9:
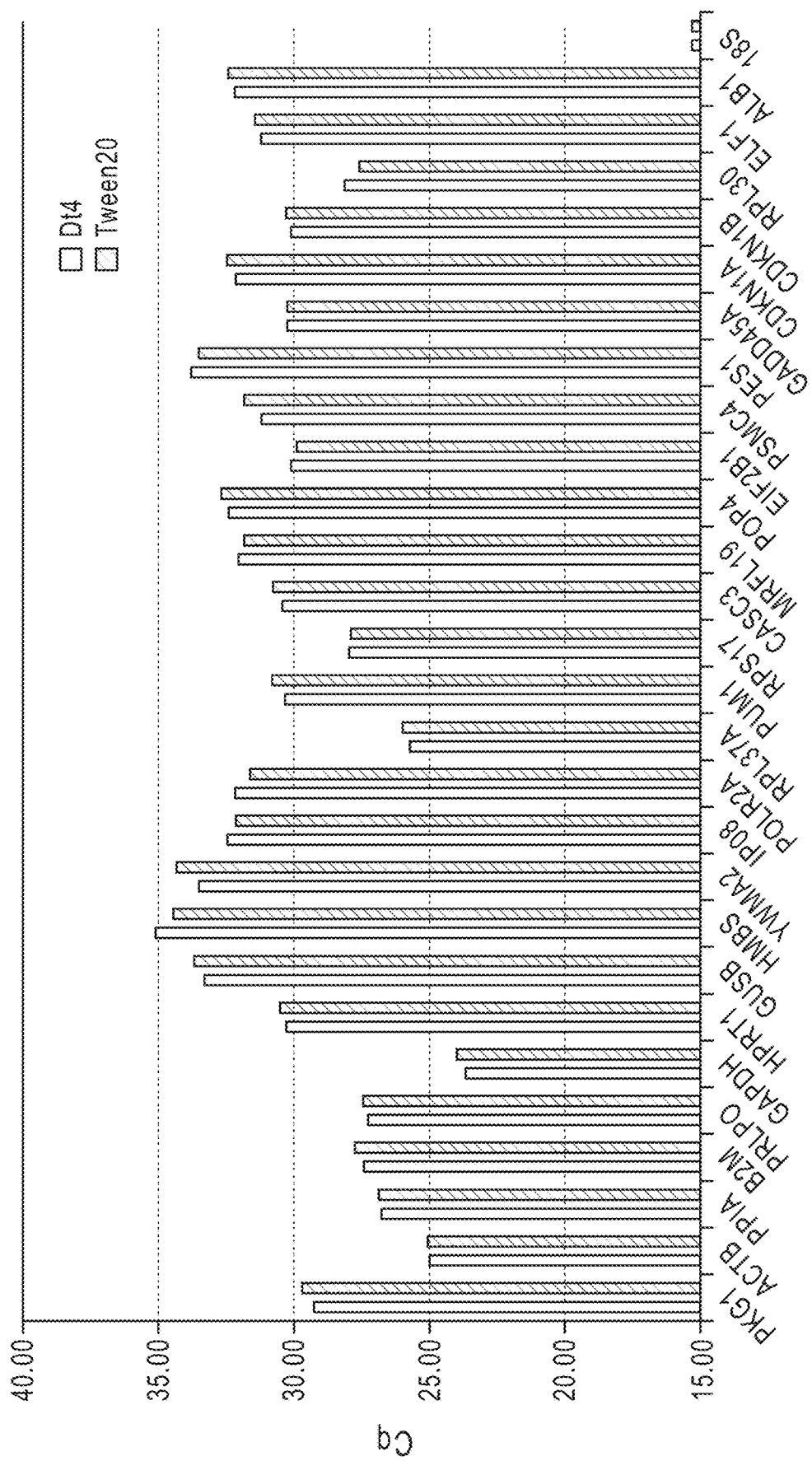
FIG. 9. Comparison of Dt4 to Tween® 20: amplification efficiency of various PCR products as represented by Cq according to certain exemplary embodiments of the methods and compositions disclosed herein.

FIG. 9 provides a comparison between Dt4 and Tween® 20 in amplifying various different targets. As shown therein, amplification in the presence of Dt4 or Tween® 20 provided similar results.

Figure 10:
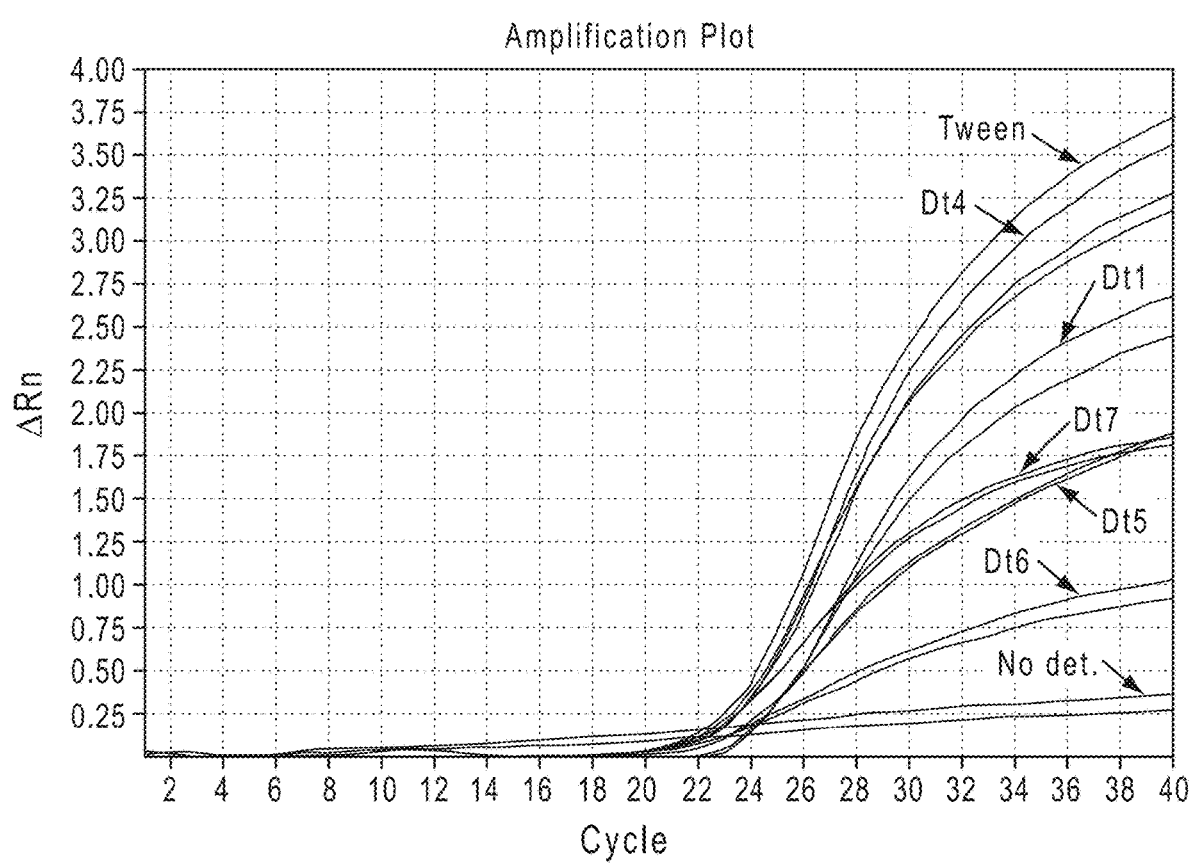
FIG. 10. Comparison of Dt1, Dt3, Dt5, Dt6, and Dt7 to Tween® 20; amplification performed according to certain exemplary embodiments of the methods and compositions disclosed herein.
Figure 11A:
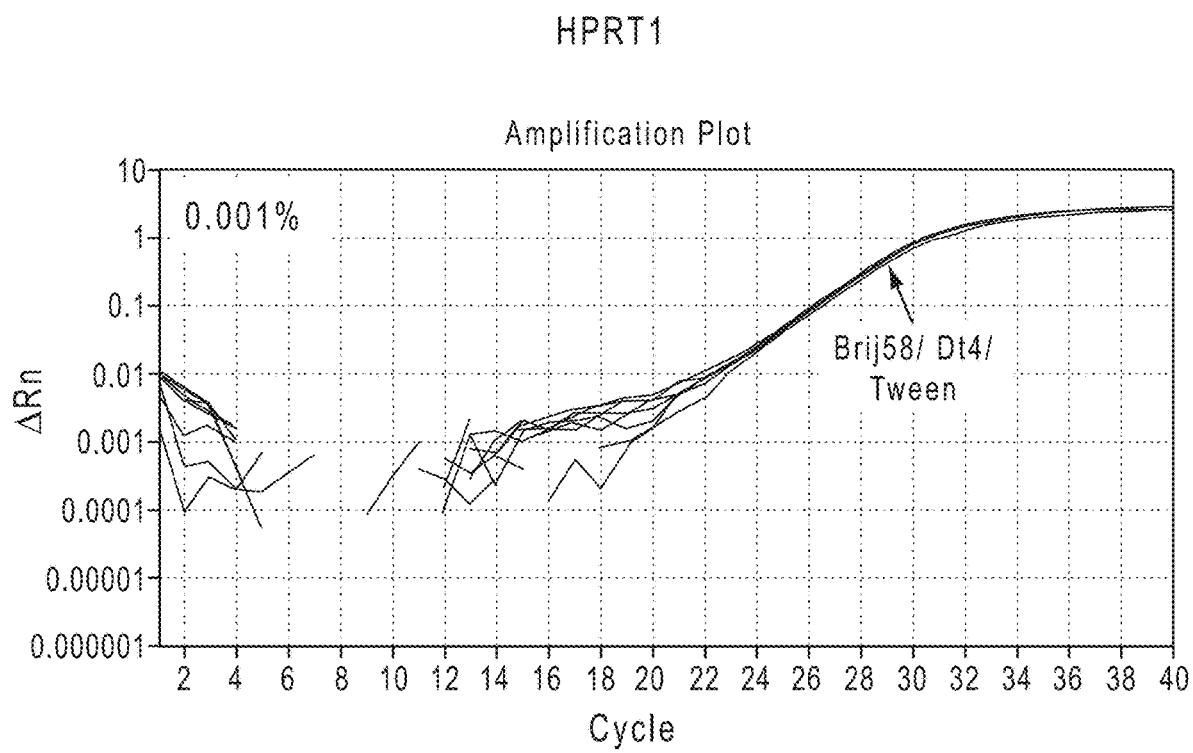
FIGS. 11A and 11B. Amplification plot of amplification reactions of hypoxanthine phosphoriboxyltransferase (HPRT1) comparing the activity of Dt4 to Brij-58 and Tween® 20 at (0.001% (FIG. 11A) and 0.0008% (FIG. 11B) of each) according to certain exemplary embodiments of the methods and compositions disclosed herein.
Figure 11B:
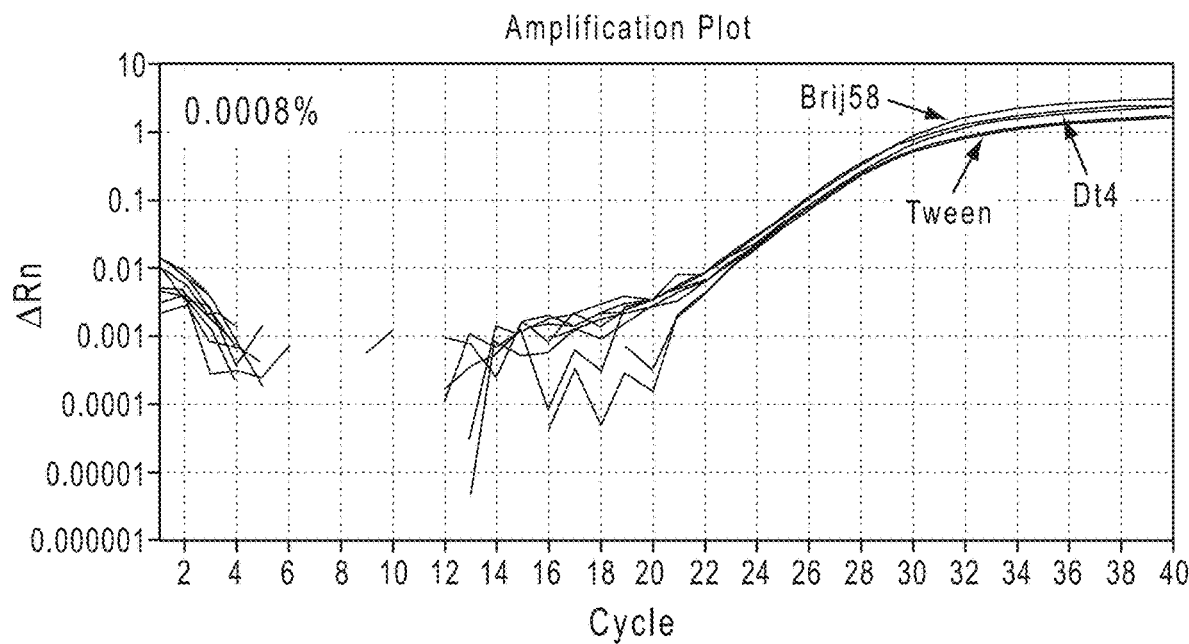
Figure 12A:
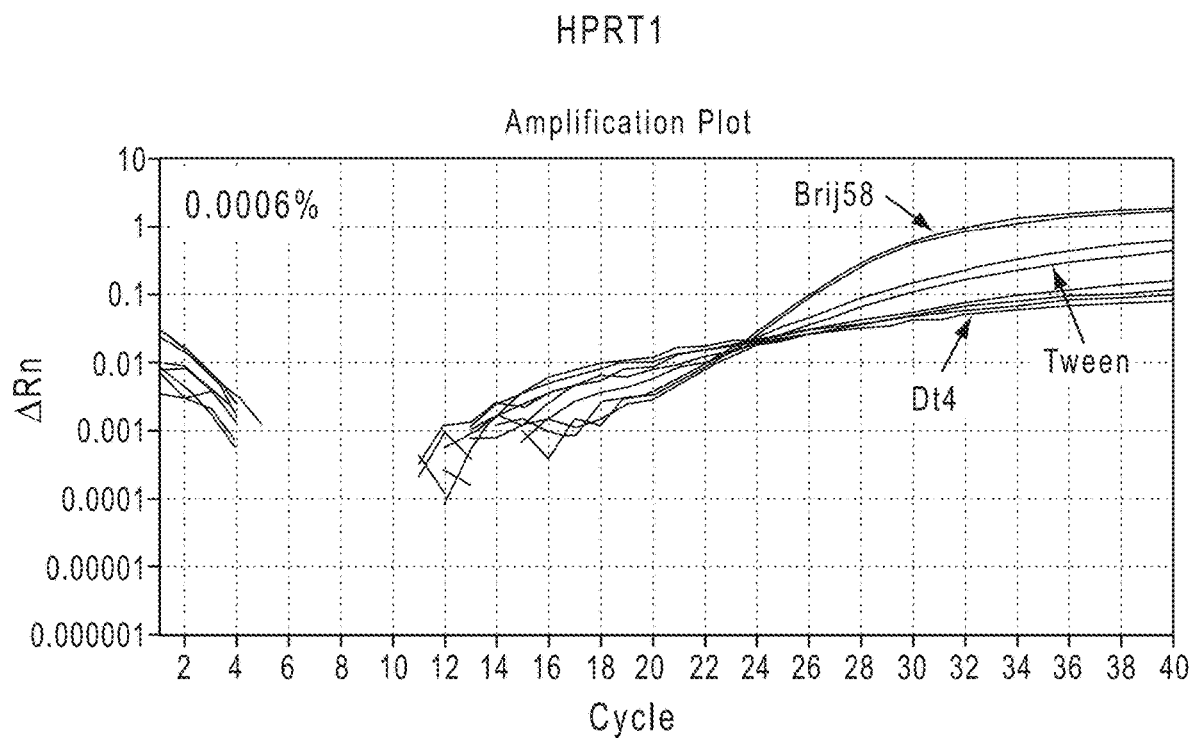
FIGS. 12A and 12B. Amplification plot of amplification reactions of HPRT1 comparing the activity of Dt4 to Brij-58 and Tween® 20 at (0.0006% (FIG. 12A) and 0.0004% (FIG. 12B) of each) according to certain exemplary embodiments of the methods and compositions disclosed herein.
Figure 12B:
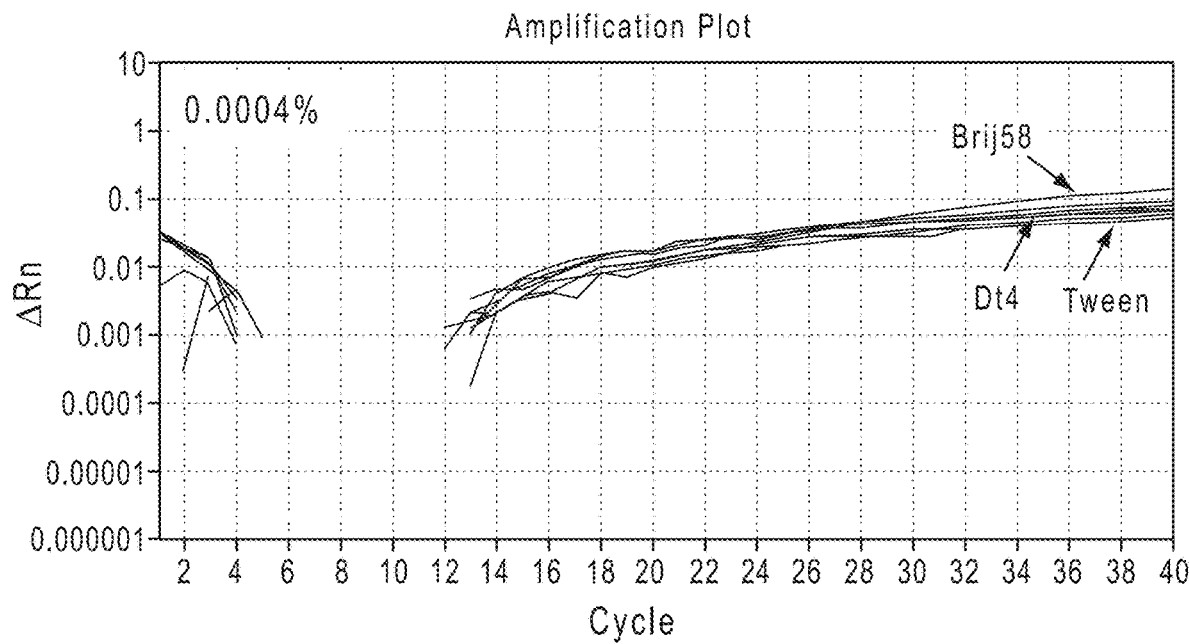
Figure 13A:
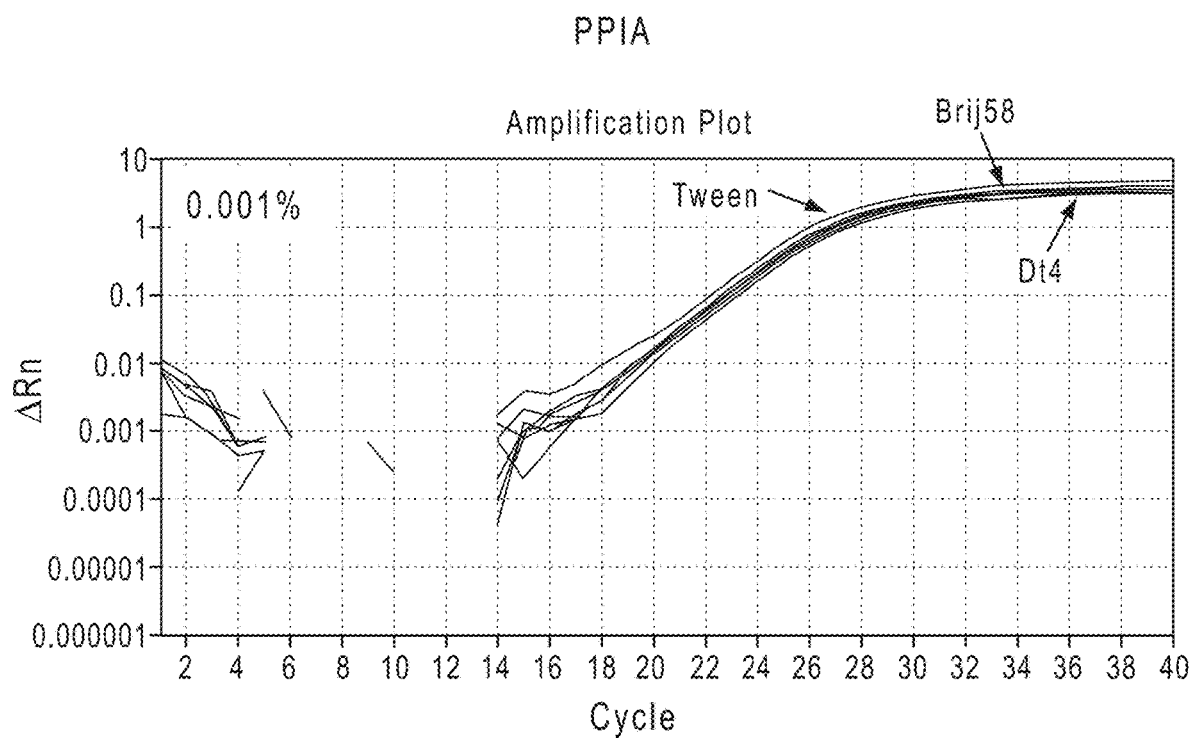
FIGS. 13A and 13B. Amplification plot of amplification reactions of peptidyl prolyl isomerase A (PPIA) comparing the activity of Dt4 to Brij-58 and Tween® 20 at (0.001% (FIG. 13A) and 0.0008% (FIG. 13B) of each) according to certain exemplary embodiments of the methods and compositions disclosed herein.
Figure 13B:
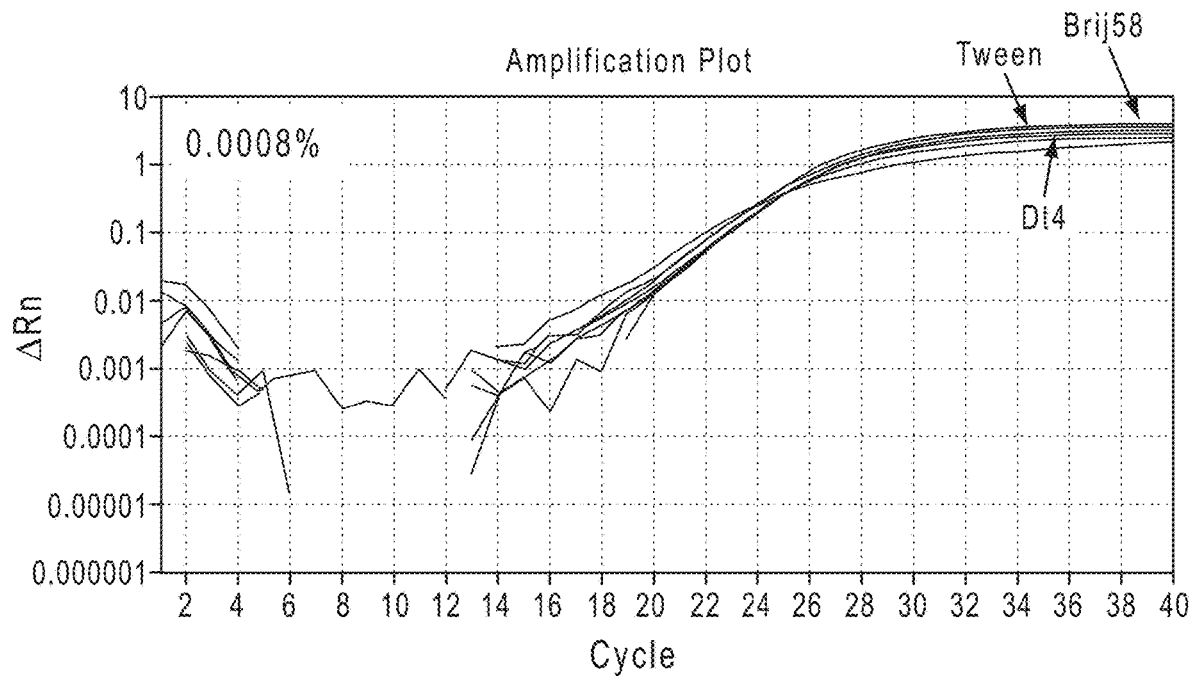
Figure 14A:
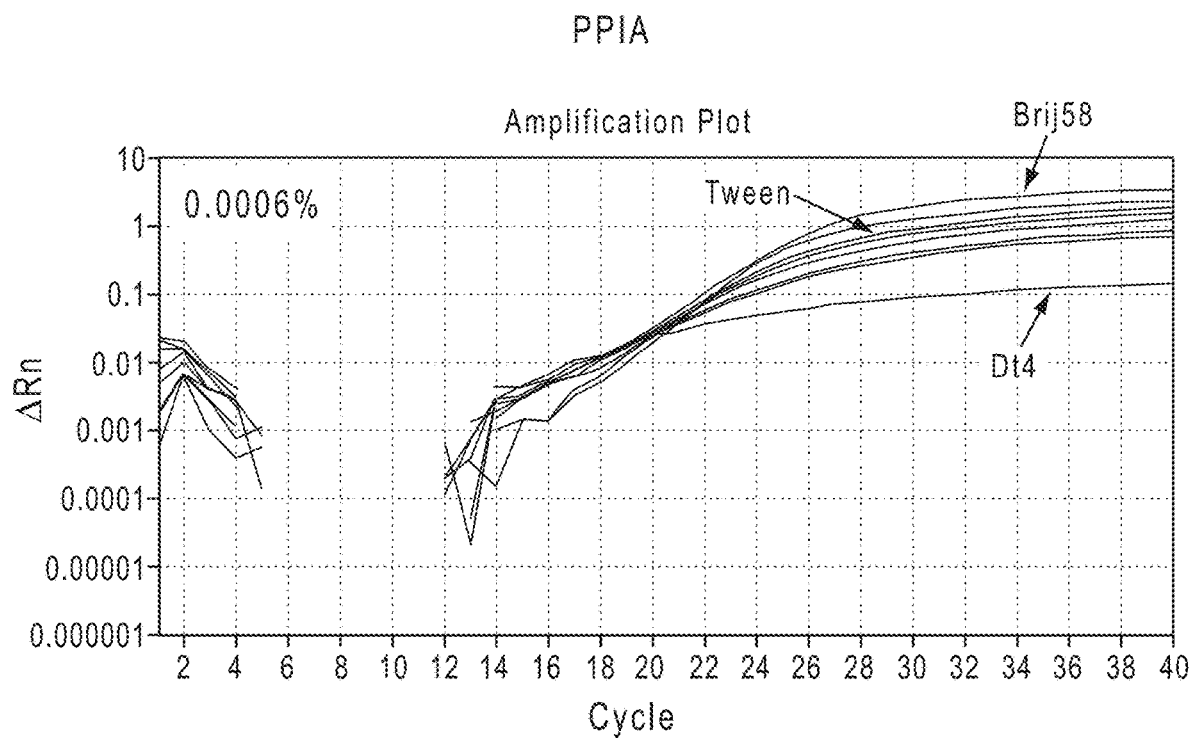
FIGS. 14A and 14B. Amplification plot of amplification reactions of PPIA comparing the activity of Dt4 to Brij-58 and Tween® 20 at (0.0006% (FIG. 14A) and 0.0004% (FIG. 14B) of each) according to certain exemplary embodiments of the methods and compositions disclosed herein.
Figure 14B:
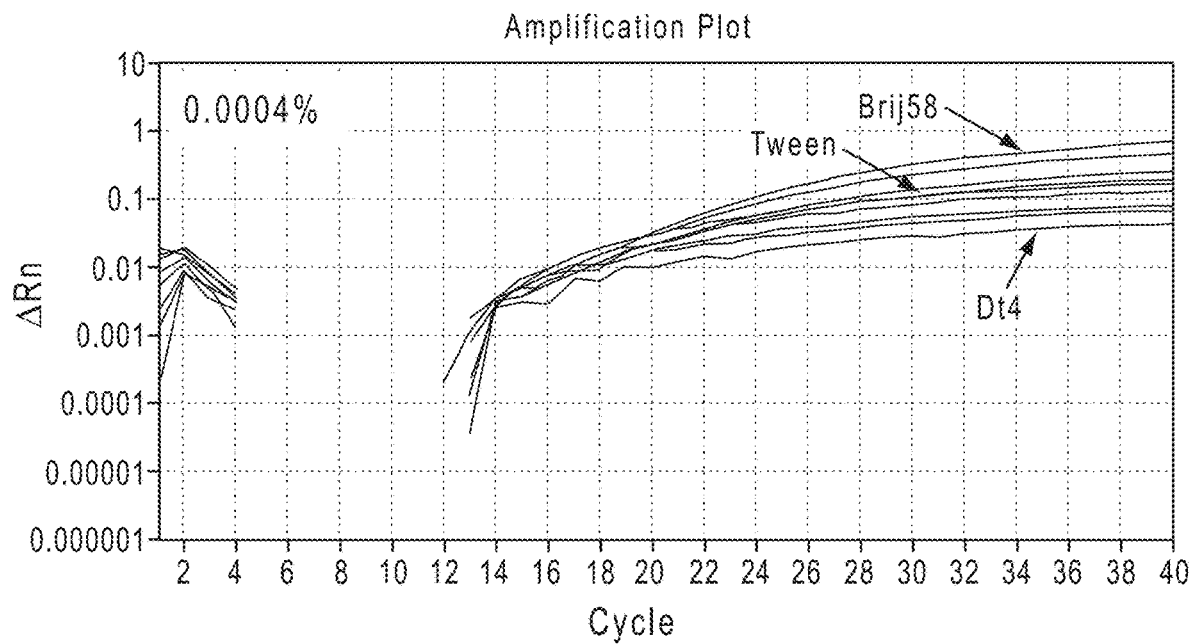
Figure 15A:
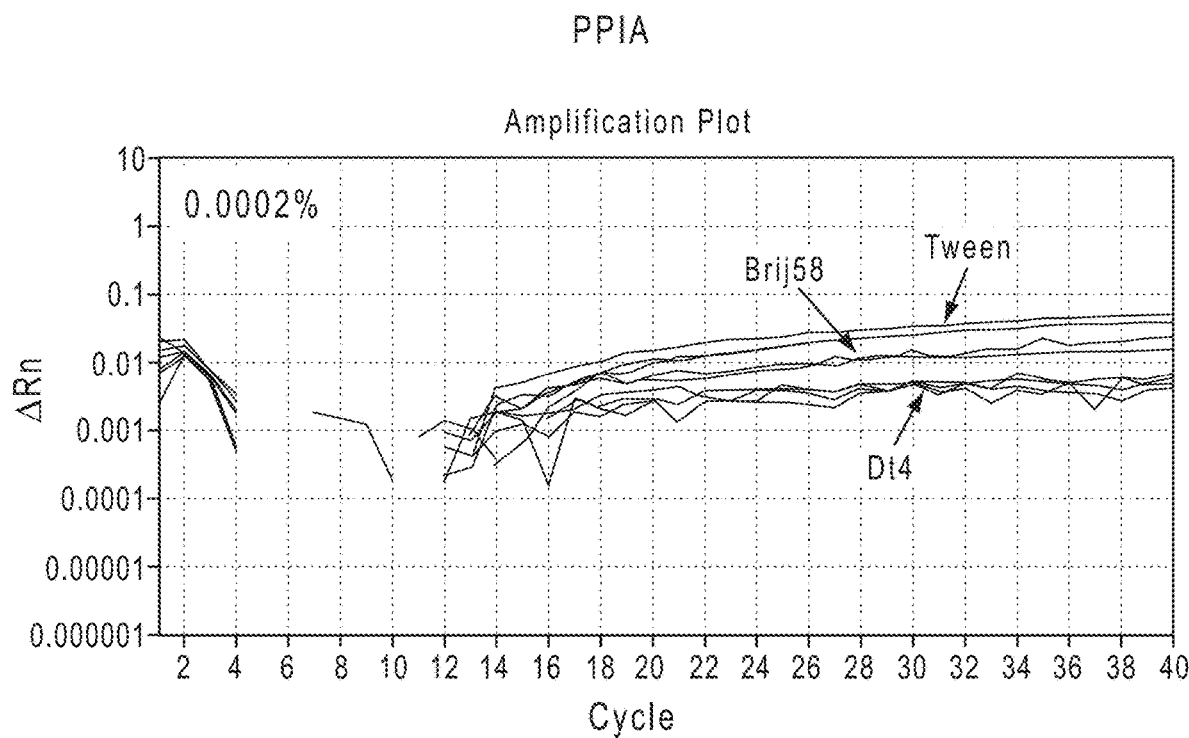
FIGS. 15A and 15B. Amplification plot of amplification reactions of PPIA comparing the activity of Dt4 to Brij-58 and Tween® 20 at (0.0002% (FIG. 15A) and 0.0001% (FIG. 15B) of each) according to certain exemplary embodiments of the methods and compositions disclosed herein.
Figure 15B:
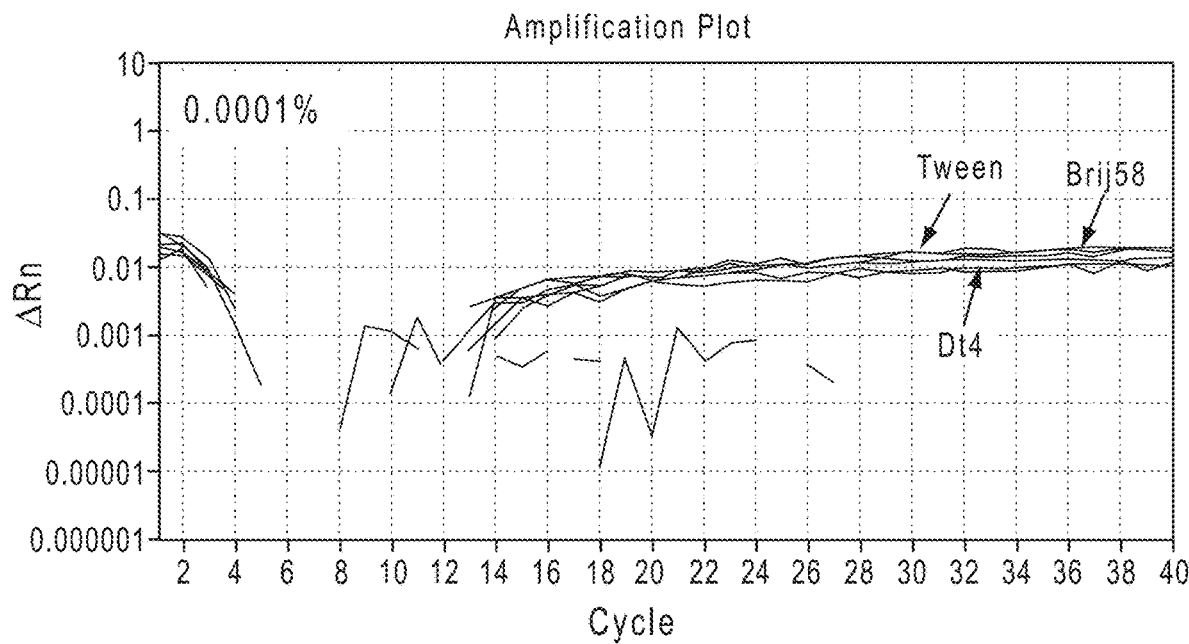

FIG. 10 illustrates the results of amplification in the presence of Dt1, Dt3, Dt5, Dt6 and Dt7. As shown therein, amplification was supported by each detergent at the highest level by Dt4 followed by Dt1, although, under the reaction conditions of these experiment. Dt5 and Dt7 exhibited similar activity, followed by Dt6.

FIGS. 11A and 11B, FIGS. 12A and 12B, FIGS. 13A and 13B, FIGS. 14A and 14B, FIGS. 15A and 15B show amplification plots comparing the activity of Dt4 to Brij-58 and Tween® 20 at various concentrations in amplifying HPRT1 or PPIA. As shown therein, Dt4 supports the amplification reaction in a comparable manner to both Brij-58 and Tween® 20 in all concentrations tested (0.001% to 0.0001%).

Figure 16:
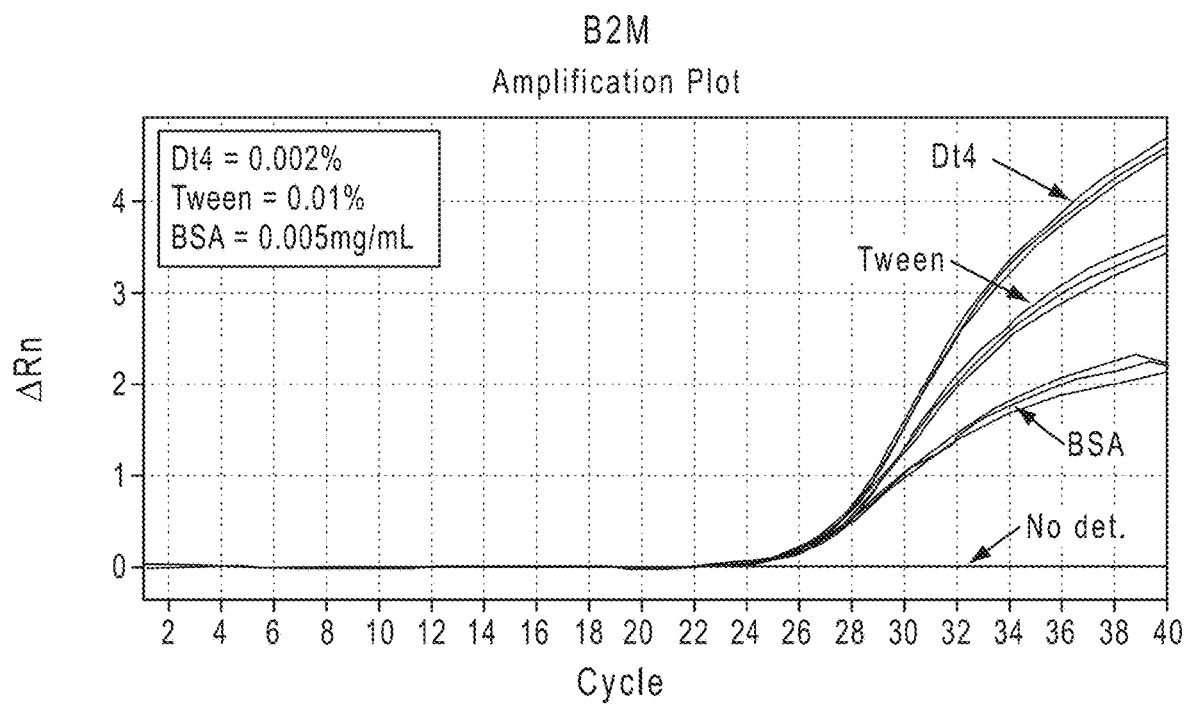
FIG. 16. Amplification plot of amplification reactions of B2M comparing the activity of 0.002% Dt4 to 0.01% and Tween® 20 according to certain exemplary embodiments of the methods and compositions disclosed herein.
Figure 17:
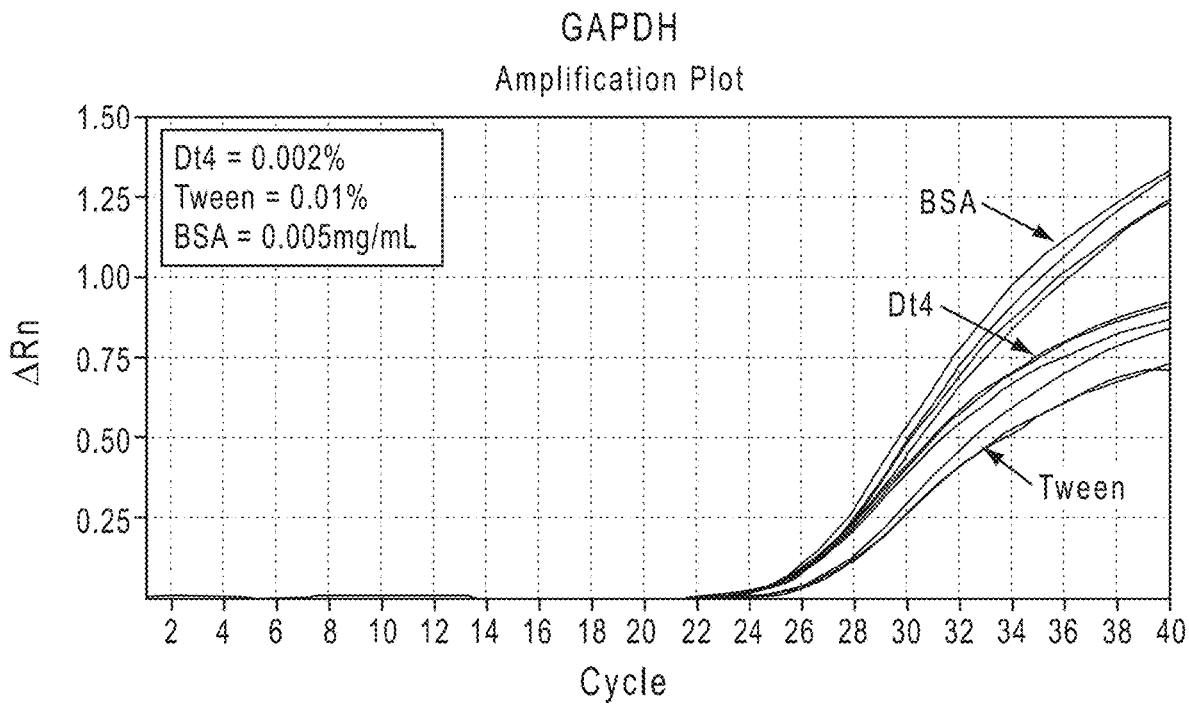
FIG. 17. Amplification plot of amplification reactions of GAPDH comparing the activity of 0.002% Dt4 to 0.01% and Tween® 20 according to certain exemplary embodiments of the methods and compositions disclosed herein.
Figure 18:
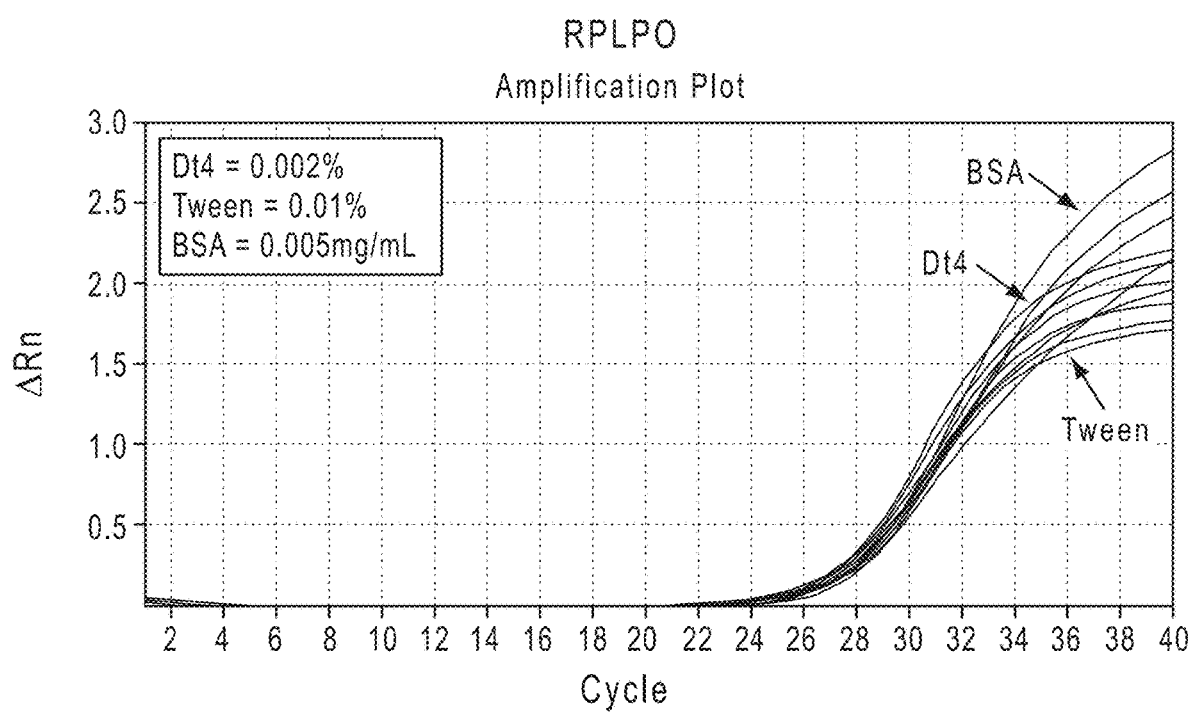
FIG. 18. Amplification plot of amplification reactions of RPLPO comparing the activity of 0.002% Dt4 to 0.01% and Tween® 20 according to certain exemplary embodiments of the methods and compositions disclosed herein.

FIGS. 16-18 illustrate that Dt4 may be used at a lower concentration than Tween® 20 in various reactions (e.g., 0.002% Dt4 compared to 0.01% Tween® 20).

Figure 19:
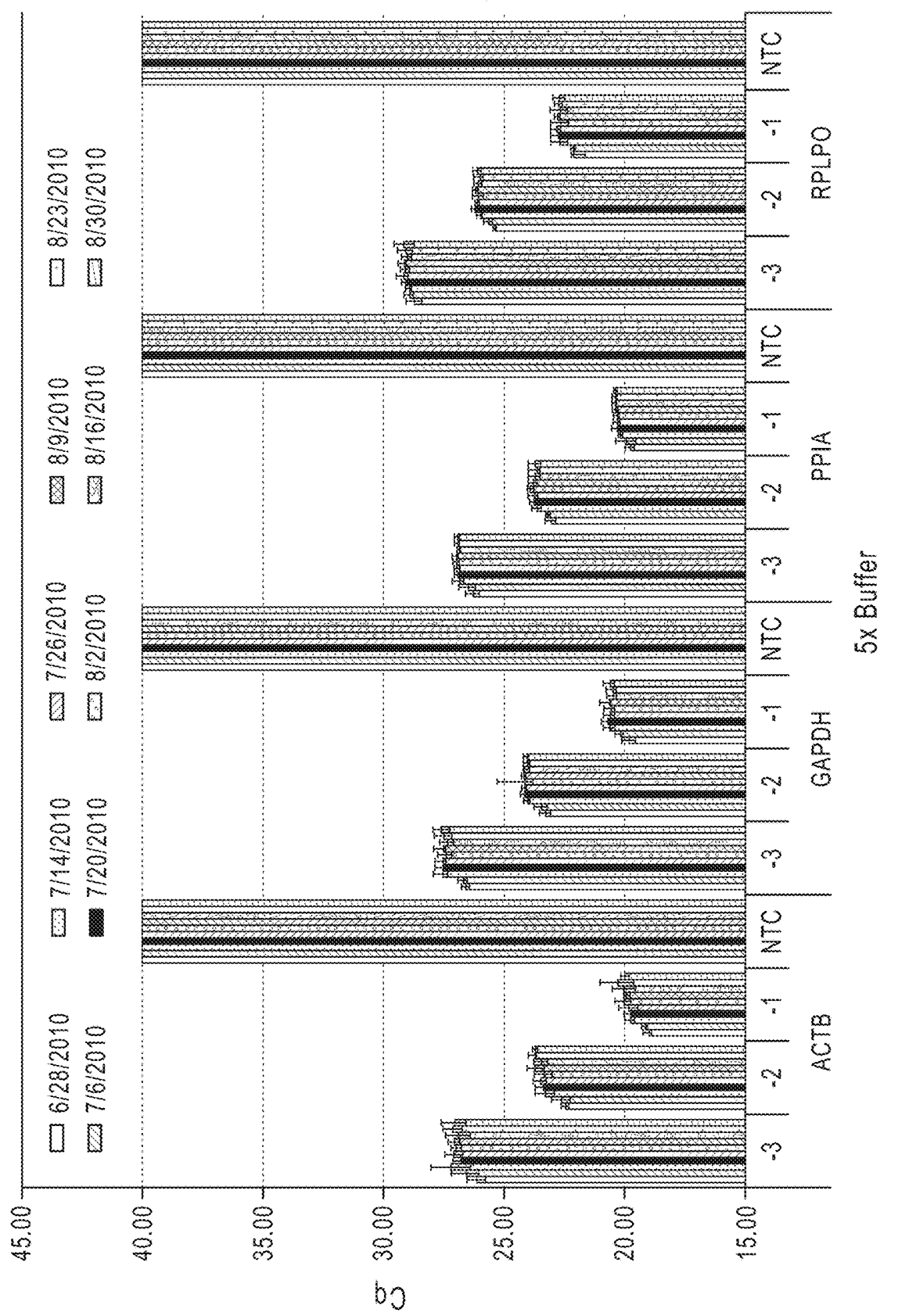
FIG. 19. Graphical representation of amplification reactions (Cq) taken at approximately one week intervals over two months demonstrating the stability of the polymerase in a 5× buffer (amplification reactions of ACTB (actin-beta), GAPDH, PPIA, and RPLPO) according to certain exemplary embodiments of the methods and compositions disclosed herein.
Figure 20:
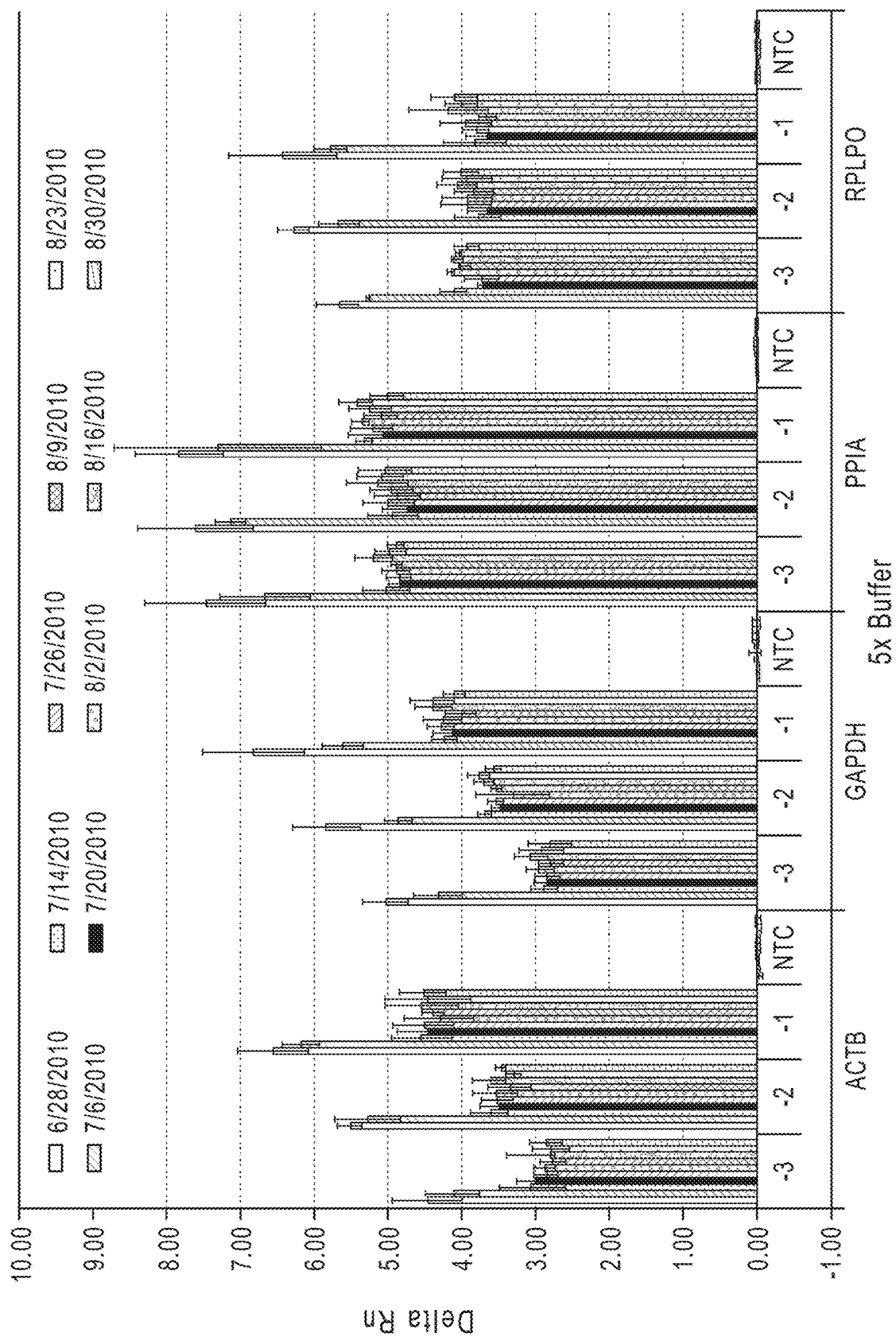
FIG. 20. Graphical representation of amplification reactions (delta Rn) taken at approximately one week intervals over two months demonstrating the stability of the polymerase in a 5× buffer (amplification reactions of ACTB (actin-beta), GAPDH, PPIA, and RPLPO) according to certain exemplary embodiments of the methods and compositions disclosed herein.

FIGS. 19 and 20 demonstrate that Dt4 is stable (e.g., it retains its ability to support amplification) in "5×" buffer (Tris (pH 8.0), KCl, and BSA) for at least two months.

Figure 21:
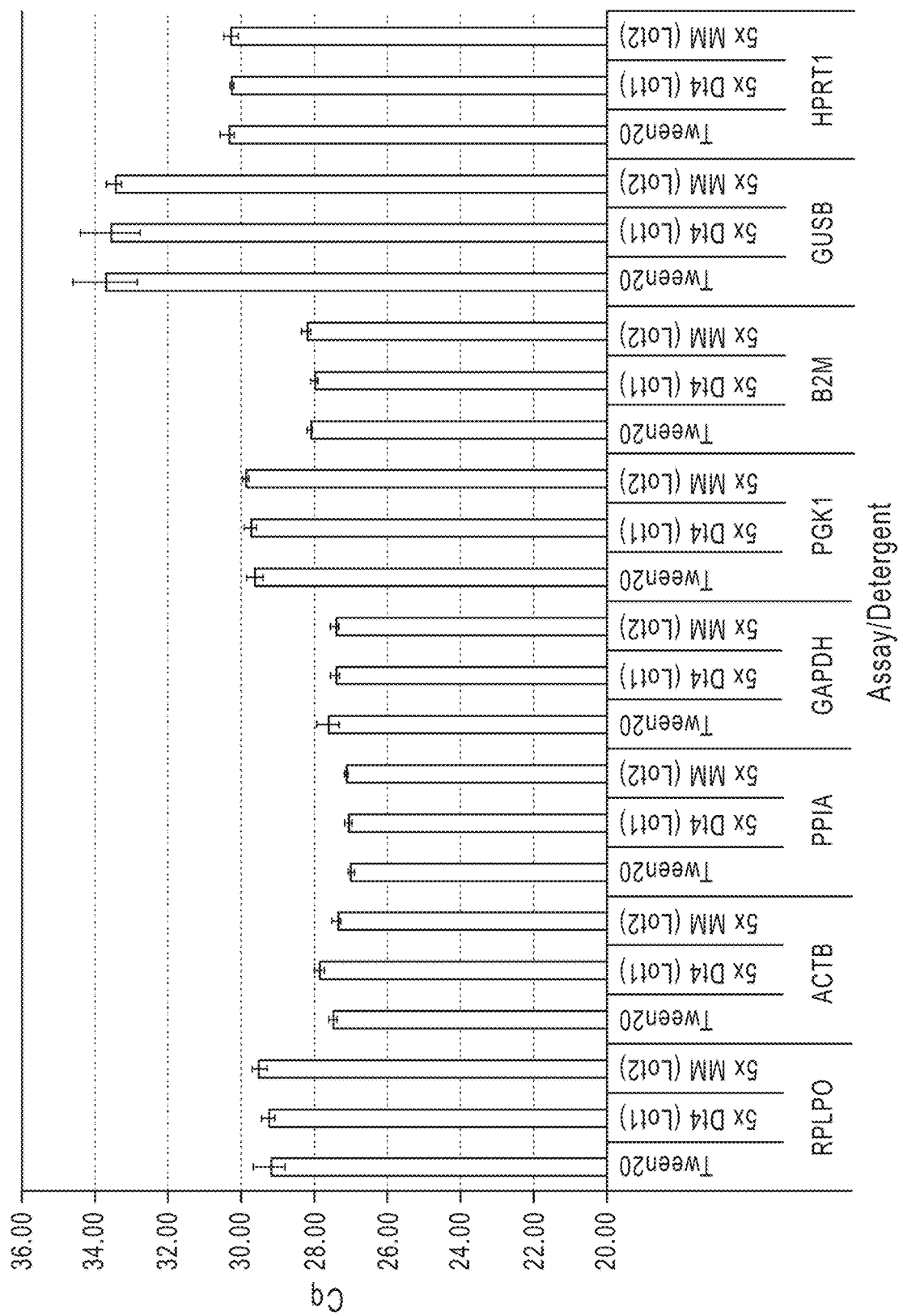
FIG. 21. Comparison of two different Dt4 lots with Tween® 20 (Cq, amplification reactions of RPLPO, ACTB, PPIA, GAPDH, PGK1 (phosphoglycerate kinase 1), B2M, GUSB, and HPRT1) Graphical representation of amplification reactions (Cq) taken at approximately one week intervals over two months demonstrating the stability of the polymerase in a 5× buffer (amplification reactions of ACTB (actin-beta), GAPDH, PPIA, and RPLPO) according to certain exemplary embodiments of the methods and compositions disclosed herein.
Figure 22:
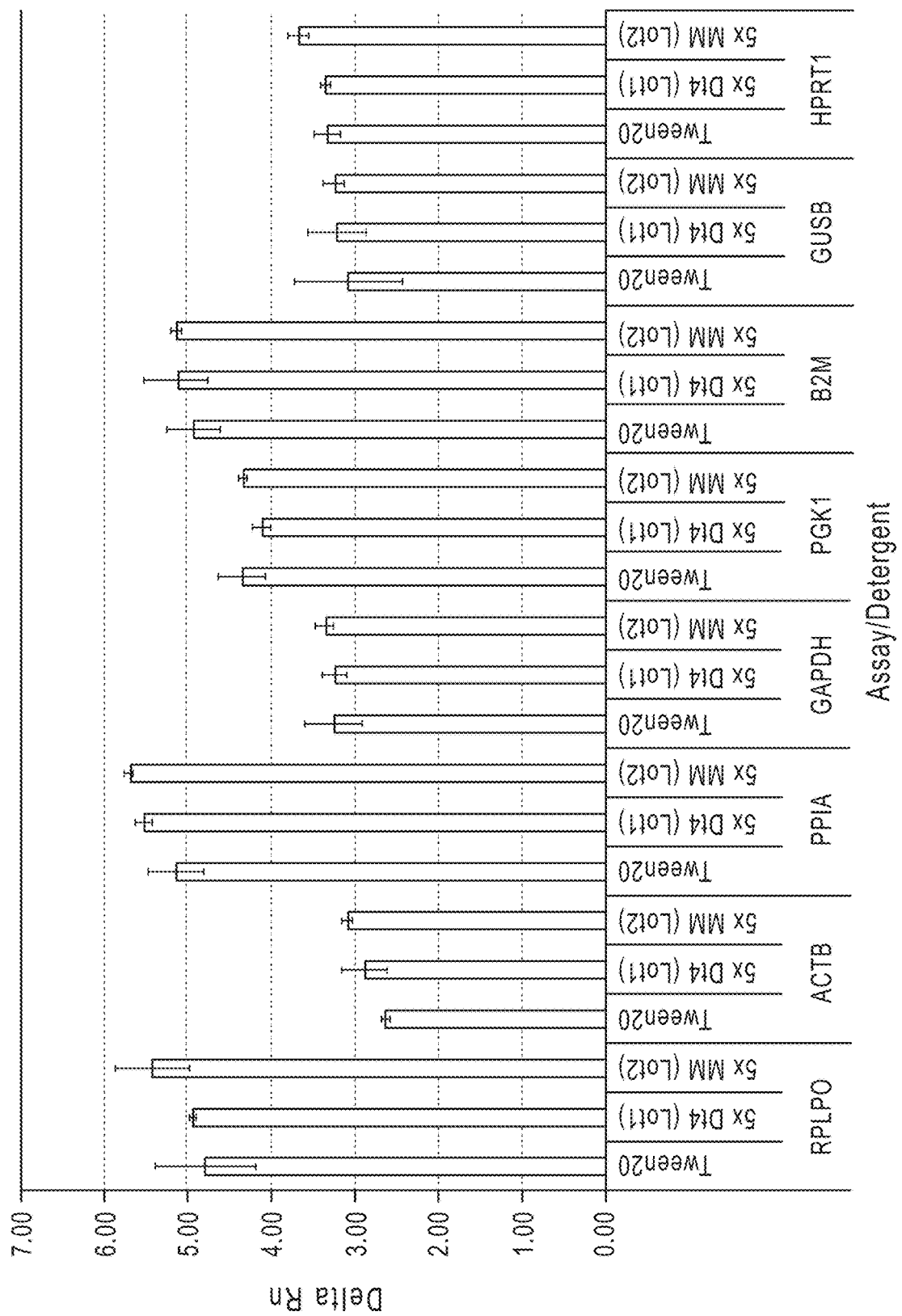
FIG. 22. Comparison of two different Dt4 lots with Tween® 20 (Delta Rn, amplification reactions of RPLPO, ACTB, PPIA, GAPDH, PGK1 (phosphoglycerate kinase 1), B2M, GUSB, and HPRT1) Graphical representation of amplification reactions (Cq) taken at approximately one week intervals over two months demonstrating the stability of the polymerase in a 5× buffer (amplification reactions of ACTB (actin-beta), GAPDH, PPIA, and RPLPO) according to certain exemplary embodiments of the methods and compositions disclosed herein.

FIGS. 21 and 22 provide a comparison of the ability of two Dt4 different lots to support amplification of various targets, as compared to Tween® 20.

Figure 23:
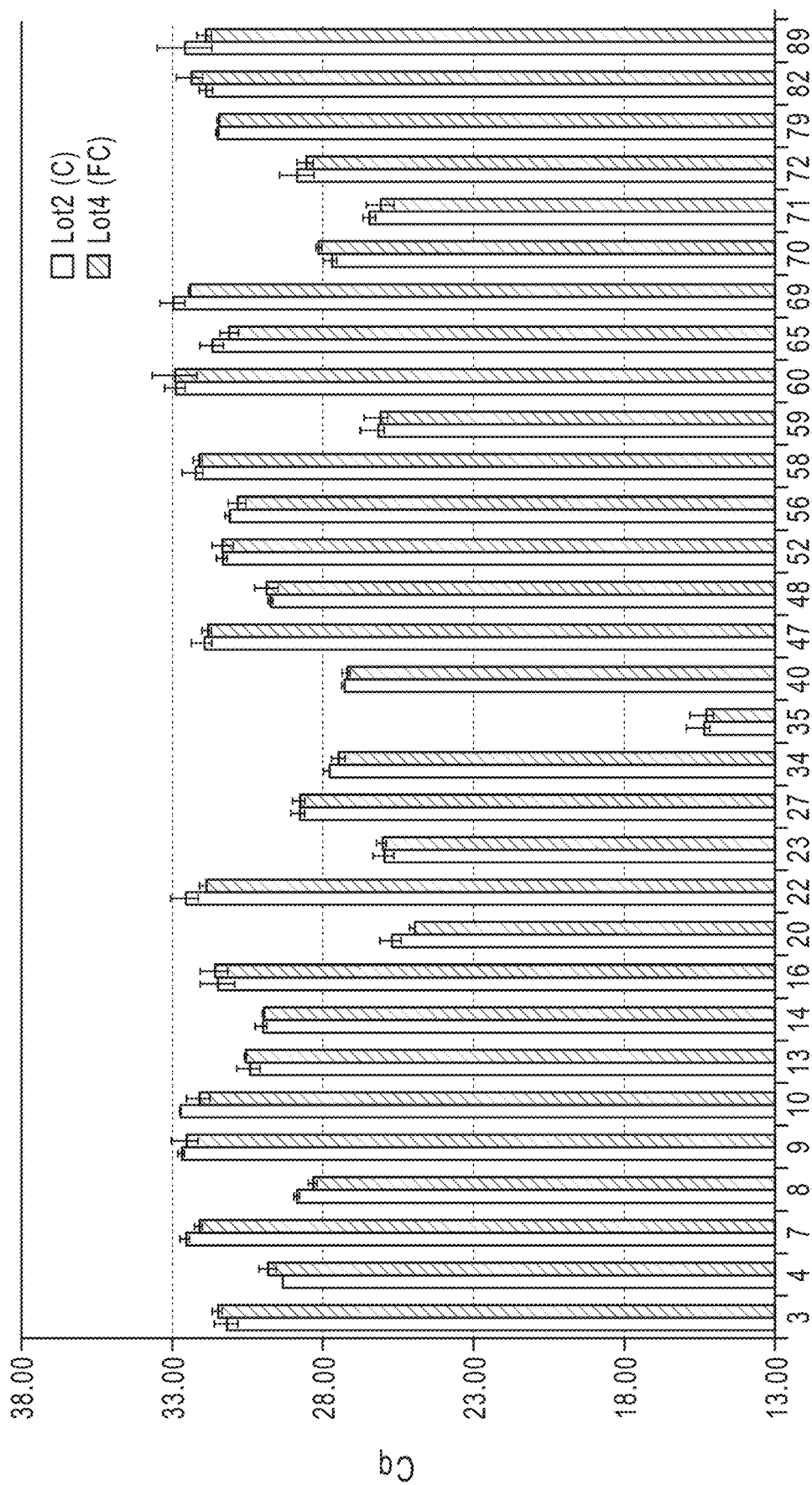
FIG. 23. Comparison of Dt4 amplification across a variety of TaqMan® assays, according to certain exemplary embodiments of the methods and compositions disclosed herein.

FIG. 23 illustrates that Dt4 supports amplification across a variety of TaqMan® assays.

Example 2

Development and Use of BrijL-23-Proline

Another compound of Formula I is shown below:

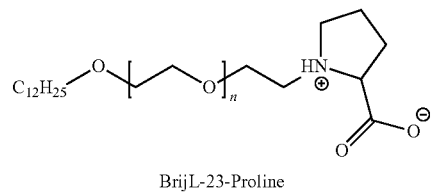

BrijL-23-Proline

BrijL-23-Proline may be prepared using Process 2 as shown below:

Process 2

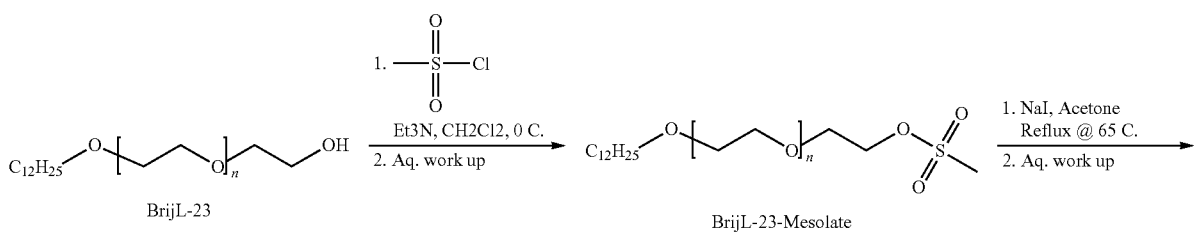

BrijL-23     BrijL-23-Mesolate

-continued

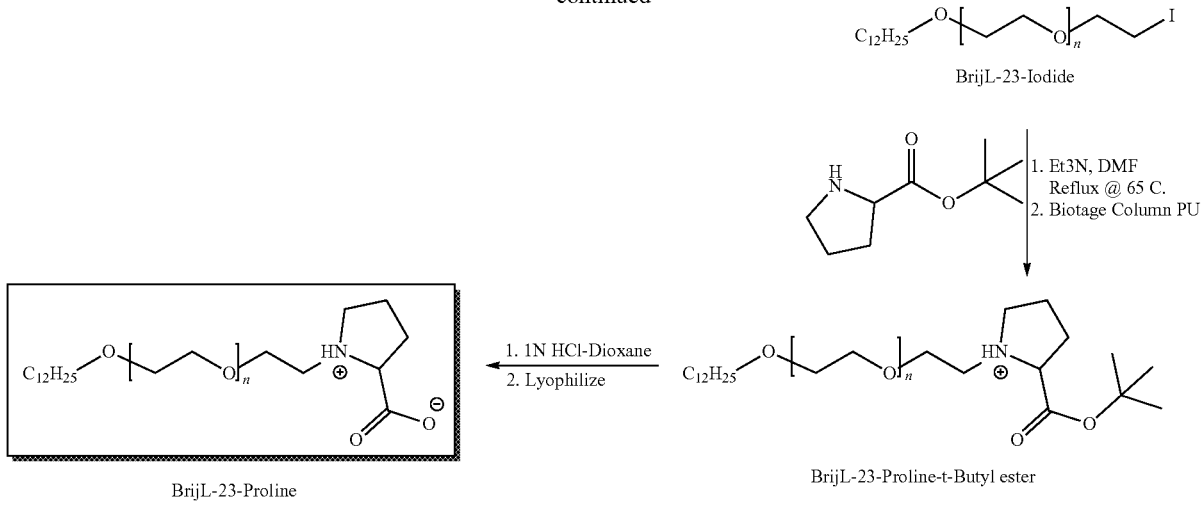

BrijL-23-Proline

Briefly, step one of Process 2 includes activating BrijL-23, working up the BrijL-23-Mesolate and drying it overnight. In step 2, BrijL-23-Iodide is formed, worked-up and dried overnight. Step 3 forms the amine in an overnight reaction followed by purification of the product, pooling of fractions containing the product, evaporation using a rotary evaporator and drying overnight. Hydrolysis of BrijL-23-Proline-t-Butyl ester with HCl is then carried out for about eight hours. Evaporation using a rotary evaporator and drying overnight leaves the final novel compound BrijL-23-Proline.

Accelerated and real-time stability tests on BrijL-23-Proline were performed. BrijL-23-Proline was stored at −20° C. Accelerated aging stability studies were conducted at 42° C. and 24° C. (ambient temperature). Accelerated aging time conversion results using the modified Arrhenius equations are shown Table 2:

TABLE 3

Accelerated Stability Testing**

| Lots | Scale | Method | Percentage in solution | Clarity of solution |
|---|---|---|---|---|
| 1 | 10 mg | LCMS, Lyoph | 5% | Clear |
| 2 | 227 mg | LCMS, Lyoph | 20% | Clear |
| 3 | 146 mg | LCMS, Lyoph | 20% | Clear |
| 4 | 1 g | LCMS, Lyoph | 20% | Clear |
| 5 | 629 mg | Biotage, Lyoph | 10% | Clear |
| 6 | 1 g | Biotage, pump-contact | 10% | Clear |

TABLE 2

| Temperature | $T_1$ | $T_2$ | $T_3$ | $T_4$ | $T_5$ | $T_6$ | $T_7$ | $T_8$ |
|---|---|---|---|---|---|---|---|---|
| −20° C. | 3 months | 6 months | 9 months | 12 months | 15 months | 18 months | 21 months | 24 months |
| 24° C. | 4.3 days | 8.5 days | 12.8 days | 17.1 days | 21.3 days | 25.6 days | 29.8 days | 34.1 days |
| 42° C. | 1 day | 2 days | 3 days | 4 days | 5 days | 6 days | 7 days | 8 days |

*$T_0$ = Sample from day 0 @ −20° C.

Different lots of BrijL-23-Proline (2 pilots) product were used for the accelerated aging stability testing. Materials were incubated at the designated temperatures (24° C. and 42° C.) in glass vials protected from light. For the 24° C. sampling point, one reagent vial from each pilot lot was removed from the incubators and tubes will be immediately stored in a −20° C. freezer. After collecting all sampling time points ($T_1$-$T_8$) from 24° C., all accelerated aging samples (24° C. and 42° C.) were checked by the LCMS QC method after conversion of samples to a liquid solution. The 24° C. study was carried out for seven weeks. The results are present in Table 3. Results of real-time stability testing are presented in Table 4.

TABLE 4

Real-Time PCR Stability Testing***

| Lots | PCR formulated with rTaq | PCR formulated with Platinum Taq | Maintains chemical identify after PCR | Storage Buffer |
|---|---|---|---|---|
| 1 | Yes | Yes | Yes | Clear |
| 2 | Yes | Yes | Yes | Clear |
| 3 | Yes | Yes | Yes | Clear |
| 4 | Yes | Yes | Yes | Clear |
| 5 | Yes | Yes | Yes | Clear |
| 6 | Yes | Yes | Yes | Clear |

***rTaq or Platinum Taq were formulated in novel detergent BrijL-23-Proline, stored for four months at −20° C. and tested for function and clarity of storage buffer.

Under both accelerated and real-time stability tests, BrijL-23-Proline was found not to precipitate and to maintain its chemical identity.

Figure 24A:
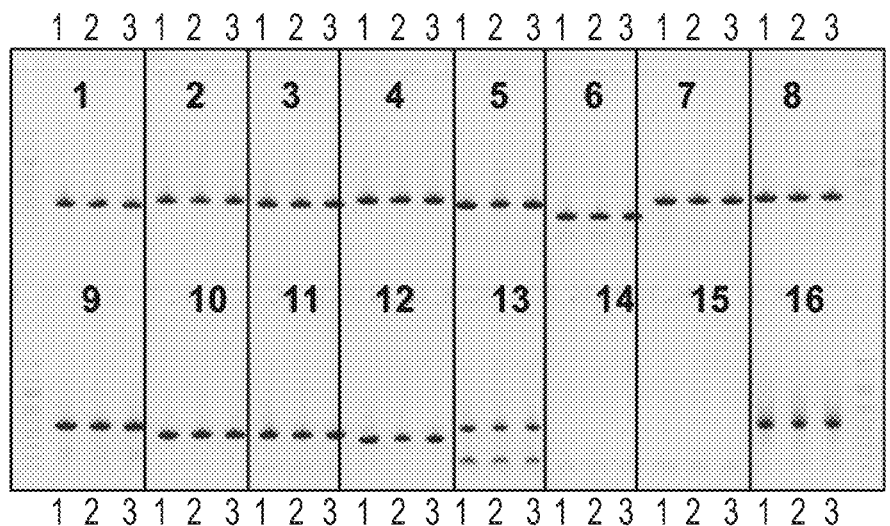
FIGS. 24A through 24C. Comparison of PCR amplification of various targets (panels 1-44) using commercially available Platinum Taq (1), Platinum Taq formulated to include the novel compound BrijL-23-Proline (2), and Platinum Taq formulated to include NP-40/Tween® 20 (3) according to certain exemplary embodiments of the methods and compositions disclosed herein. Each panel represents a specific target sequence (1 through 44) amplified using a reaction mixture comprising the various enzyme formulations described above (1, 2 or 3).
Figure 24B:
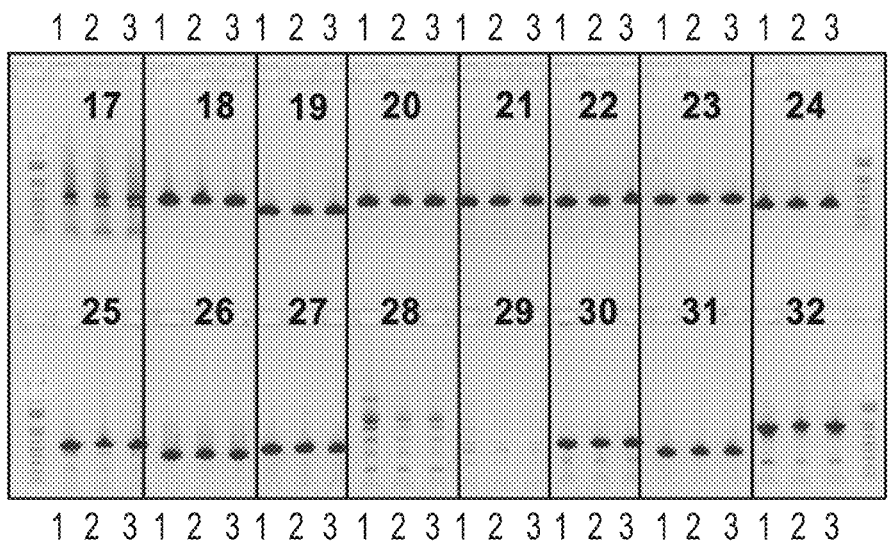
Figure 24C:
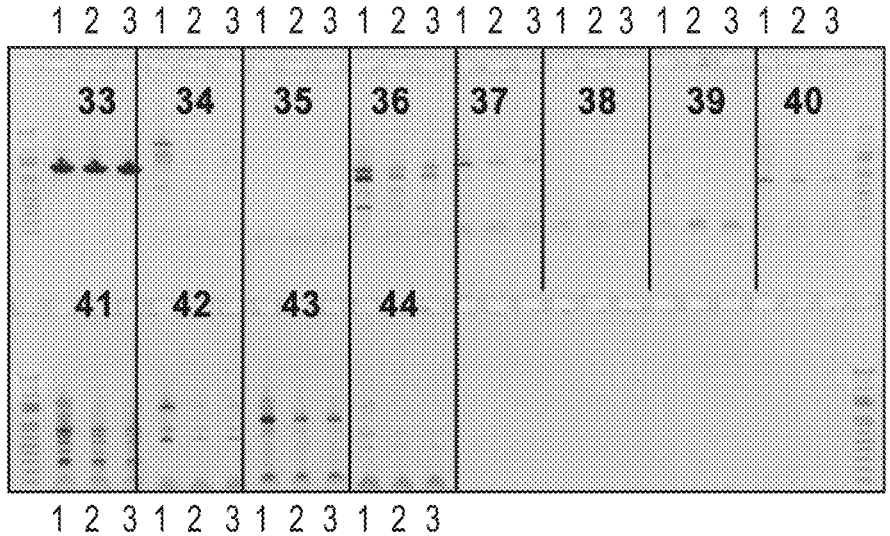

BrijL-23-Proline was tested for its ability to support nucleic acid amplification by a polymerase. Forty-four nucleic acid targets were amplified by PCR using Taq polymerase in the presence of 0.1% NP-40 and 0.1% Tween® 20 (control reactions), or BrijL-23-Proline (2 µl detergent/50 µl reaction, 35 cycles). As shown in FIGS. 24A through 24C, BrijL-23-Proline supported the 44 different amplification reactions in a comparable manner to commercially available Platinum Taq and Platinum Taq formulated in NP-40/Tween® 20.

Figure 25A:
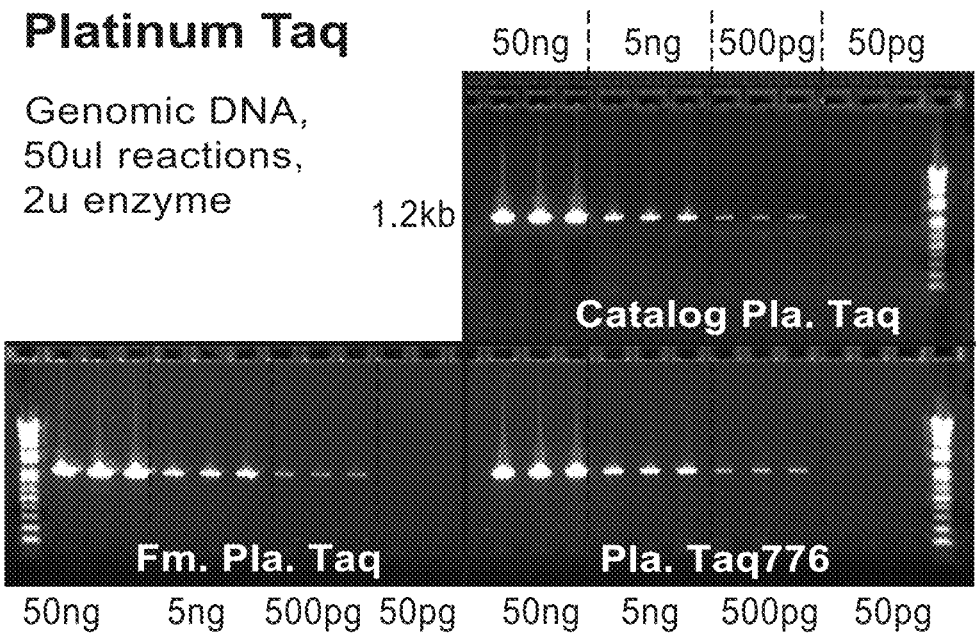
FIGS. 25A and 25B. Sensitivity of Platinum Taq (FIG. 25A) and rTaq (FIG. 25B) formulated to include BrijL-23-Proline or NP-40/Tween® 20 according to certain exemplary embodiments of the methods and compositions disclosed herein. Genomic DNA was amplified using reaction comprising 50 ng, 5 ng, 500 pg or 50 pg of DNA. Amplification reactions were performed using various formulations, such as those described. "Fm. Pla. Taq" is a formulation of Platinum Taq (10 u/µl) with NP-40/Tween® 20. "Catalog Pla. Taq is a formulation of commercially available Platinum Taq. "Pla. Taq776" is a formulation of Platinum Taq (10 u/µl) with BrijL-23-Proline. "Fm. Taq" is a formulation of rTaq (5 u/µl) with NP-40/Tween®. "Catalog Taq" is a formulation of commercially available rTaq. "Taq776" is a formulation of rTaq (5 u/µl) with BrijL-23-Proline.
Figure 25B:
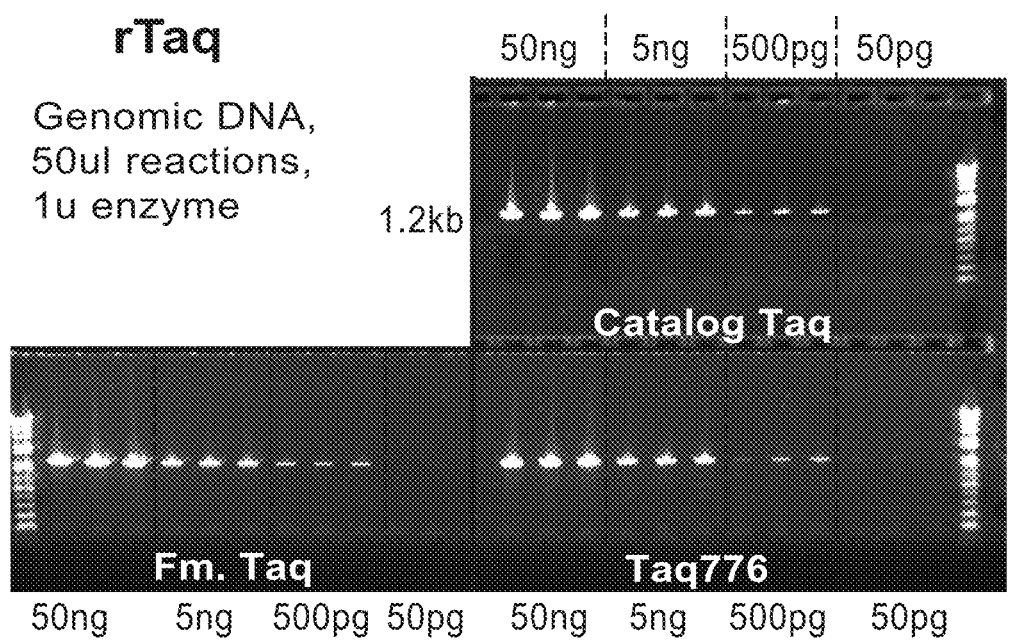
Figure 26A:
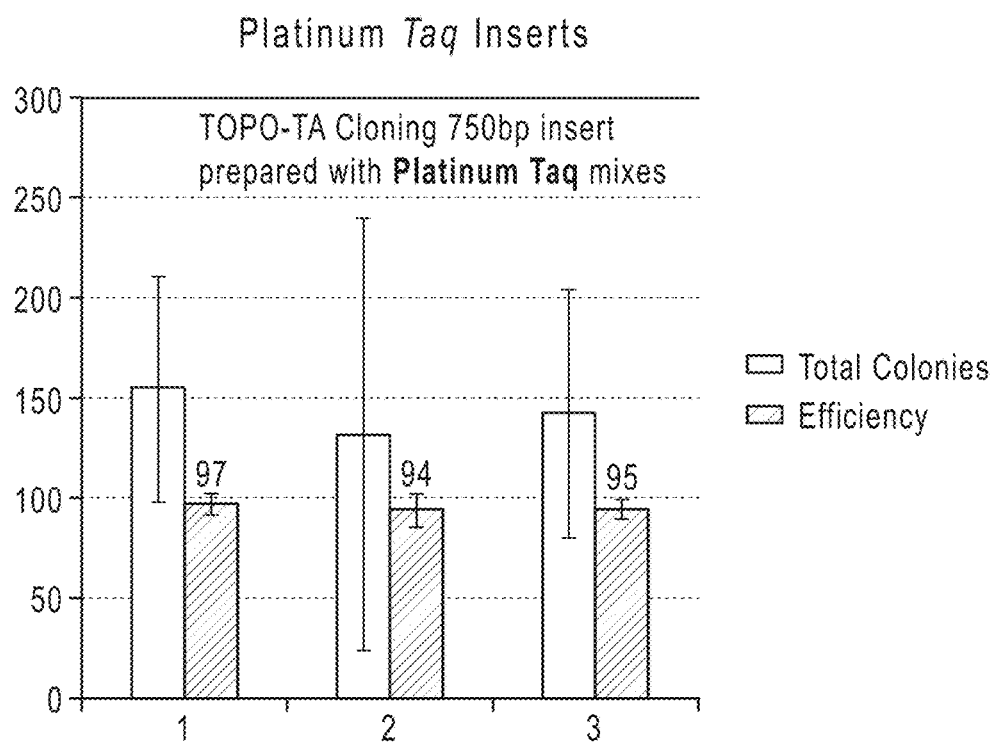
FIGS. 26A through 26D. Comparison of TOPO-TA cloning of PCR products amplified using either Platinum Taq (FIG. 26A and FIG. 26B) or rTaq (FIG. 26C and FIG. 26D) mixes. Mixes were prepared using commercially available Platinum Taq (1), commercially available rTaq (A), Platinum Taq formulated to include the novel compound BrijL-23-Proline (2), rTaq formulated to include the novel compound BrijL-23-Proline (B), Platinum Taq formulated to include NP-40/Tween® 20 (3), and rTaq formulated to include NP-40/Tween® 20 (C) according to certain exemplary embodiments of the methods and compositions disclosed herein.
Figure 26B:
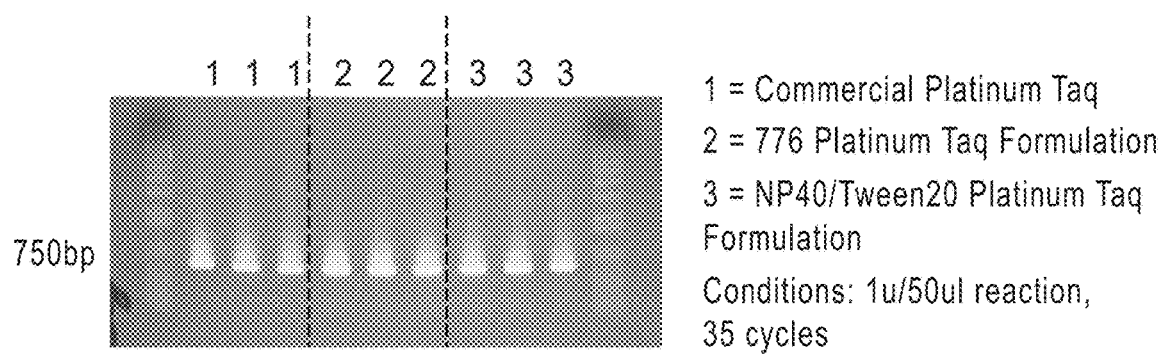
Figure 26C:
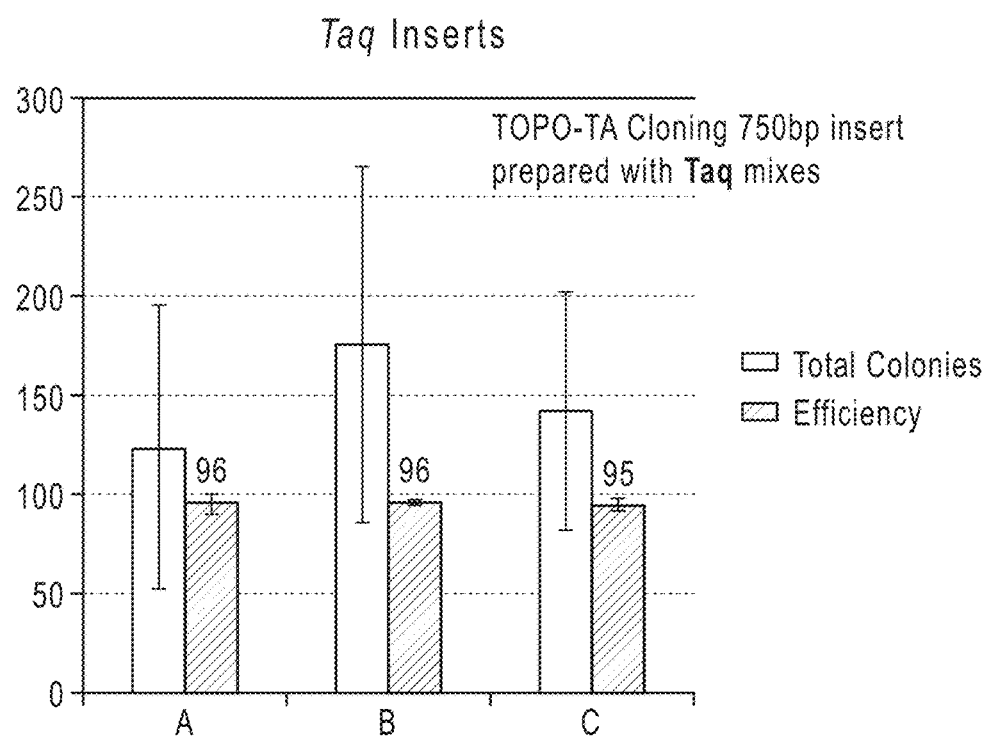
Figure 26D:
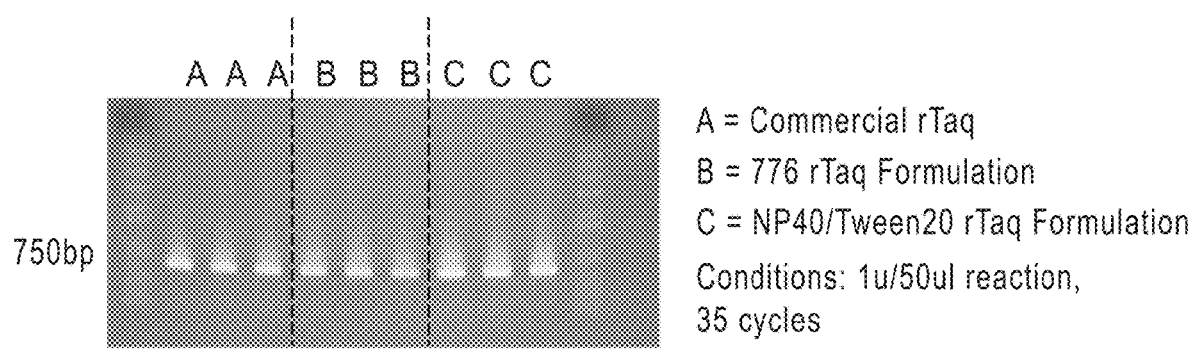

The sensitivity of Platinum Taq and rTaq formulated in BrijL-23-Proline or NP-40/Tween® 20 was also tested (50 ng, 5 ng, 500 pg, 50 pg of a 1.2 kb amplicon; 50 µl reactions using one µl polymerase). As shown in FIGS. 25A and 25B, the sensitivity of the formulations was equivalent for a 1.2 kb amplicon.

TOPO-TA cloning of a 750 bp PCR product amplified using commercially available Platinum Taq (1), commercially available rTaq (A), Platinum Taq formulated in the novel detergent BrijL-23-Proline (2), rTaq formulated in the novel detergent BrijL-23-Proline (B), Platinum Taq formulated in NP-40/Tween® 20 (3), or Taq formulated in NP-40/Tween® 20 (C) was also compared. As shown in FIGS. 26A through 26D, equivalent cloning performance among the different compositions was observed.

All references cited within this disclosure are hereby incorporated by reference in their entirety. While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A compound, having the structure:

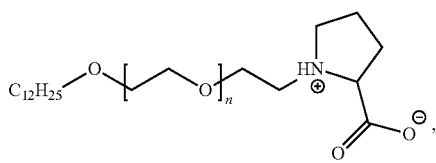

wherein each n is independently any positive integer, including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

2. A method for inhibiting inactivation of a polymerase in a thermal cycling process, said method comprising contacting said polymerase with the compound of claim 1 during the thermal cycling process.

3. The method of claim 2, wherein said inhibition of polymerase inactivation is the same as the inhibition of polymerase inactivation when the polymerase is in the presence of NP-40 and/or Tween® 20 instead of said compound.

4. The method of claim 2, wherein said inhibition of polymerase inactivation is greater than the inhibition of polymerase inactivation when the polymerase is in the presence of NP-40 or Tween® 20 instead of said compound.

5. The method of claim 2, wherein said polymerase is thermostable.

6. The method of claim 2, wherein said polymerase is selected from the group consisting of T7 DNA polymerase, eukaryotic mitochondrial DNA Polymerase γ, prokaryotic DNA polymerase I, prokaryotic DNA polymerase II, prokaryotic DNA polymerase III, prokaryotic DNA polymerase IV, prokaryotic DNA polymerase V, eukaryotic polymerase α, eukaryotic polymerase β, eukaryotic polymerase γ, eukaryotic polymerase δ, eukaryotic polymerase ε, eukaryotic polymerase η, eukaryotic polymerase ζ, eukaryotic polymerase ι, eukaryotic polymerase κ, E. coli DNA polymerase I, E. coli DNA polymerase III alpha subunit, E. coli DNA polymerase III epsilon subunits, E. coli polymerase IV, E. coli polymerase V, T. aquaticus DNA polymerase I, B. stearothermophilus DNA polymerase I, a Euryarchaeota polymerase, terminal deoxynucleotidyl transferase (TdT), S. cerevisiae polymerase 4, a translesion synthesis polymerase, reverse transcriptase, a thermostable polymerase, and telomerase.

7. The method of claim 5, wherein said thermostable polymerase is selected from the group consisting of Taq DNA polymerase, Tfi DNA polymerase, Tfl DNA polymerase, Pfu DNA polymerase, and Vent™ DNA polymerase, a polymerase having reduced 3'-to-5' exonuclease activity, SuperScript™ DNA polymerase, a genetically engineered DNA polymerase, a polymerase having the active site mutation F667Y, a polymerase having the equivalent of active site F667Y, Tth polymerase, AmpliTaq®FS, ThermoSequenase™, Therminator I, Therminator II, Therminator III, Therminator Gamma, a derivative thereof, and a fragment thereof.

8. The method of claim 7, wherein said thermostable polymerase is Taq DNA polymerase.

9. The method of claim 7, wherein said thermostable polymerase is Tfl DNA polymerase.

10. A method for producing a modified detergent comprising:
 a) activating BrijL-23 to produce BrijL-23-Mesolate;
 b) preparing BrijL-23-Iodide from BrijL-23-Mesolate;
 c) preparing BrijL-23-Proline-t-Butyl ester from BrijL-23-Iodide; and,
 d) hydrolyzing BrijL-23-Proline-t-Butyl ester to produce BrijL-23-Proline;
 wherein said modified detergent comprises the compound of claim 1.

11. The method of claim 10, further comprising neutralizing the product.

12. The method of claim 11, wherein said product is neutralized using Amberlite®.

* * * * *